(12) United States Patent
Smith et al.

(10) Patent No.: US 9,199,975 B2
(45) Date of Patent: Dec. 1, 2015

(54) BIARYL IMIDAZOLE DERIVATIVES FOR REGULATING CYP17

(71) Applicant: Asana Biosciences, LLC, Bridgewater, NJ (US)

(72) Inventors: Roger Astbury Smith, Chester Springs, PA (US); Nicholas James Laping, Malvern, PA (US); Scott Kevin Thompson, Phoenixville, PA (US); Raghava Reddy Kethiri, Noida (IN); Dhanalakshmi Sivanandhan, Noida (IN); Chandregowda Venkateshappa, Noida (IN); Bheemashankar Kulkarni, Noida (IN); Purushottam Dewang, Noida (IN); Rajendra Kristam, Noida (IN); Srinivas Kasibhatla, Noida (IN); Rajesh Devraj, Noida (IN)

(73) Assignee: Asana Biosciences, LLC, Bridgewater, NJ (US)

( * ) Notice: Subject to any disclaimer, the term of this patent is extended or adjusted under 35 U.S.C. 154(b) by 0 days.

(21) Appl. No.: 13/632,007

(22) Filed: Sep. 30, 2012

(65) Prior Publication Data

US 2013/0085164 A1    Apr. 4, 2013

Related U.S. Application Data

(63) Continuation-in-part of application No. PCT/US2012/057908, filed on Sep. 28, 2012.

(60) Provisional application No. 61/541,634, filed on Sep. 30, 2011.

(51) Int. Cl.

| | | |
|---|---|---|
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |
| C07D 419/00 | (2006.01) |
| C07D 421/00 | (2006.01) |
| C07D 403/02 | (2006.01) |
| C07D 233/00 | (2006.01) |
| A61K 31/44 | (2006.01) |
| A61K 31/415 | (2006.01) |
| C07D 405/14 | (2006.01) |
| C07D 401/06 | (2006.01) |
| C07D 409/06 | (2006.01) |
| C07D 409/14 | (2006.01) |
| C07D 417/06 | (2006.01) |
| C07D 417/14 | (2006.01) |
| C07D 405/06 | (2006.01) |

(52) U.S. Cl.
CPC ............ *C07D 405/14* (2013.01); *C07D 401/06* (2013.01); *C07D 405/06* (2013.01); *C07D 409/06* (2013.01); *C07D 409/14* (2013.01); *C07D 417/06* (2013.01); *C07D 417/14* (2013.01)

(58) Field of Classification Search
CPC ..... C07D 401/00; C07D 421/00; A61K 31/44
See application file for complete search history.

(56) References Cited

U.S. PATENT DOCUMENTS

| | | |
|---|---|---|
| 4,118,487 A | 10/1978 | Regel |
| 4,863,943 A | 9/1989 | DeBourge |
| 4,914,207 A | 4/1990 | Nagel |
| 5,128,327 A | 7/1992 | Chakravarty |
| 5,354,759 A | 10/1994 | Oku |
| 5,389,635 A | 2/1995 | Olson |
| 5,389,641 A | 2/1995 | Naka |
| 5,612,365 A | 3/1997 | Heitsch |
| 5,739,153 A | 4/1998 | Peignier |
| 5,808,064 A | 9/1998 | Chen |
| 5,854,264 A | 12/1998 | Anthony |
| 5,874,452 A | 2/1999 | Anthony |
| 5,877,329 A | 3/1999 | Chen |

(Continued)

FOREIGN PATENT DOCUMENTS

| | | |
|---|---|---|
| EP | 94167 | 11/1983 |
| EP | 180313 | 5/1986 |

(Continued)

OTHER PUBLICATIONS

Jagusch, C. et al. Synthesis, biological evaluation and molecular modeling studies of methyleneimidazole substituted biaryls as inhibitors of human 17α-hydroxylase-17,20-lyase (CYP17). Part I: Heterocyclic modifications of the core structure. Bioorganic & Medicinal Chemistry. 2008, vol. 16, p. 1994.*

(Continued)

*Primary Examiner* — Janet L Andres
*Assistant Examiner* — Ben S Michelson
(74) *Attorney, Agent, or Firm* — Lerner, David, Littenberg, Krumholz & Mentlik, LLP

(57) ABSTRACT

The present application provides novel imidazole compounds and pharmaceutically acceptable salts thereof. Also provided are methods for preparing these compounds. These compounds are useful in inhibiting CYP17 activity by administering a therapeutically effective amount of one or more of the compounds to a patient. By doing so, these compounds are effective in treating conditions associated with CPY17 activity. A variety of conditions can be treated using these compounds and include diseases which are characterized by abnormal cellular proliferation. In one embodiment, the disease is cancer, such as prostate cancer.

18 Claims, No Drawings

(56) References Cited

U.S. PATENT DOCUMENTS

| | | |
|---|---|---|
| 6,090,804 A | 7/2000 | Kimura |
| 6,090,807 A | 7/2000 | Hellendahl |
| 6,562,817 B1 | 5/2003 | Tanimoto |
| 6,653,306 B1 | 11/2003 | Alexander |
| 6,787,517 B1 | 9/2004 | Gil |
| 6,982,268 B2 | 1/2006 | Xie |
| 7,019,006 B2 | 3/2006 | Cirillo |
| 7,129,264 B2 | 10/2006 | Smallheer |
| 7,169,779 B2 | 1/2007 | Salituro |
| 7,312,235 B2 | 12/2007 | Zhu |
| 7,598,274 B2 | 10/2009 | Finsinger |
| 2001/0044545 A1 | 11/2001 | Dhanoa |
| 2002/0151715 A1 | 10/2002 | Alanine |
| 2003/0083269 A1 | 5/2003 | Brouillette |
| 2003/0220380 A1 | 11/2003 | Dhanoa |
| 2004/0006095 A1 | 1/2004 | Zhang |
| 2004/0054179 A1 | 3/2004 | Yura |
| 2004/0167224 A1 | 8/2004 | Ozaki |
| 2004/0248850 A1 | 12/2004 | Ernst |
| 2004/0267017 A1 | 12/2004 | Bierer |
| 2005/0070542 A1 | 3/2005 | Hodgetts |
| 2005/0176710 A1 | 8/2005 | Schwink |
| 2005/0203151 A1 | 9/2005 | Malecha |
| 2005/0272779 A1 | 12/2005 | Edwards |
| 2005/0272793 A1 | 12/2005 | Goto |
| 2006/0004021 A1 | 1/2006 | Johansson |
| 2006/0035893 A1 | 2/2006 | Jung |
| 2006/0211738 A1 | 9/2006 | Mitchell |
| 2006/0263411 A1 | 11/2006 | Tachdjian |
| 2006/0264426 A1 | 11/2006 | Zhou |
| 2007/0043057 A1 | 2/2007 | Matteucci |
| 2007/0082913 A1 | 4/2007 | Kim |
| 2007/0123516 A1 | 5/2007 | Jung |
| 2007/0155724 A1 | 7/2007 | Moss |
| 2007/0173504 A1 | 7/2007 | Pacofsky |
| 2007/0219181 A1 | 9/2007 | Kimura |
| 2007/0293507 A1 | 12/2007 | Baik |
| 2008/0255203 A1 | 10/2008 | Lee |
| 2008/0262028 A1 | 10/2008 | Kallus |
| 2009/0082370 A1 | 3/2009 | Thompson |
| 2009/0137592 A1 | 5/2009 | Scott |
| 2009/0203699 A1 | 8/2009 | Barth |
| 2009/0221586 A1 | 9/2009 | Okada |
| 2009/0270359 A1 | 10/2009 | Ito |
| 2010/0010001 A1 | 1/2010 | Roberts |
| 2010/0022564 A1 | 1/2010 | Davies |
| 2010/0075990 A1 | 3/2010 | Endres |
| 2010/0130464 A1 | 5/2010 | Davies |
| 2010/0130509 A1 | 5/2010 | Schuren |
| 2010/0166699 A1 | 7/2010 | Thompson |
| 2010/0179059 A1 | 7/2010 | Renner |
| 2010/0234591 A1 | 9/2010 | Zhou |
| 2010/0292258 A1 | 11/2010 | Ackermann |
| 2011/0003998 A1 | 1/2011 | Dumas |
| 2011/0065129 A1 | 3/2011 | Lowe |
| 2011/0068306 A1 | 3/2011 | Liao |
| 2011/0172186 A1 | 7/2011 | Behnke |
| 2011/0190343 A1 | 8/2011 | Gochin |
| 2011/0294836 A1 | 12/2011 | Song |
| 2012/0053180 A1 | 3/2012 | Kang |

FOREIGN PATENT DOCUMENTS

| | | |
|---|---|---|
| EP | 0260744 | 3/1988 |
| EP | 300688 | 1/1989 |
| EP | 0371564 | 6/1990 |
| EP | 2447261 | 5/2012 |
| GB | 2276161 | 9/1994 |
| GB | 2276162 | 9/1994 |
| GB | 2427406 | 12/2006 |
| JP | 06-092939 | 4/1994 |
| JP | 06-340658 | 12/1994 |
| WO | WO-93/18030 | 9/1993 |
| WO | WO-94/04153 | 3/1994 |
| WO | WO-97/27187 | 7/1997 |
| WO | WO-97/48676 | 12/1997 |
| WO | WO-98/57937 | 12/1998 |
| WO | WO-00/01676 | 1/2000 |
| WO | WO-02/00651 | 1/2002 |
| WO | WO-2004/094591 | 11/2004 |
| WO | WO-2005/054210 | 6/2005 |
| WO | WO-2005/108374 | 11/2005 |
| WO | WO-2006/084186 | 8/2006 |
| WO | WO-2007/011759 | 1/2007 |
| WO | WO-2007/038425 | 4/2007 |
| WO | WO-2008/030887 | 3/2008 |
| WO | WO-2009/117421 | 9/2009 |
| WO | WO-2010/139966 | 12/2010 |
| WO | WO-2011/082098 | 7/2011 |
| WO | WO-2011/153192 | 12/2011 |
| WO | WO-2012/010567 | 1/2012 |
| WO | WO-2012/058531 | 5/2012 |

OTHER PUBLICATIONS

Hu, Q. et al. Synthesis, biological evaluation and molecular modeling studies of methylene imidazole substituted biaryls as inhibitors of human 17α-hydroxylase-17,20-lyase (CYP17). Part II: Core rigidification and influence of substituents at the methylene bridge. Bioorganic & Medicinal Chemistry. 2008, vol. 16, p. 7718.*

Hu, Q. et al. The Role of Fluorine Substitution in Biphenyl Methylene Imidazole-Type CYP17 Inhibitors for the Treatment of Prostate Carcinoma. ChemMedChem. 2010, vol. 5, p. 902.*

Hille, "First Selective CYP11B1 Inhibitors for the Treatment of Cortisol-Dependent Diseases", ACS Med. Chemistry Letters, 2:2-6 (2011; e-publication: Oct. 22, 2010).

Jagusch, "Synthesis, biological evaluation and molecular modeling studies of methyleneimidazole substituted biaryls as inhibitors of human 17α-hydroxylase-17,20lyase (CYP17). Part I: Heterocyclic modifications of the core structure", Bioorganic & Medicinal Chemistry, 16:1992-2010 (2008: e-publication: Nov. 4, 2007).

Hu, "Synthesis, biological evaluation and molecular modeling studies of methyleneimidazole substituted biaryls as inhibitors of human 17α-hydroxylase-17,20-lyase (CYP17). Part II: Core rigidification and influence of substituents at the methylene bridge", Bioorganic & Medicinal Chemistry, 16:7715-7727 (2008; e-publication: Jul. 9, 2008).

Yap, "Targeting CYP17: established and novel approaches in prostate cancer", Current Opinion in Pharmacology, 8:449-457 (2008; e-publication: Jul. 28, 2008).

Vasaitis, "CYP17 inhibitors for prostate cancer therapy", Journal of Steroid Biochemistry & Molecular Biology, 125:23-31 (May 2011; e-publication: Nov. 17, 2010).

Reid, "CYP17 inhibition as a hormonal strategy for prostate cancer", Nature Clinical Practice Urology, 5(11):610 (Nov. 2008).

English-language abstract of Japanese Patent No. JP-06-340658, published Dec. 13, 1994.

English-language abstract of Japanese Patent No. JP-06-092939, published Apr. 5, 1994.

Smith, U.S. Appl. No. 13/632,006, filed Sep. 30, 2012.

Written Opinion of the International Searching Authority dated Apr. 1, 2014 issued in counterpart International Patent Application No. PCT/2012/057908.

Mendieta, "CYP17 Inhibitors. Annulations of Additional Rings in Methylene Imidazole Substituted Biphenyls: Synthesis, Biological Evaluation and Molecular Modelling", Arch. Pharm. Chem. Life Sci., vol. 341, No. 10, pp. 597-609, Oct. 1, 2008.

Hille, "Optimization of the First Selective Steroid-11β-hydroxylase (CYP11B1) Inhibitors for the Treatment of Cortisol Dependent Diseases", ACS Medicinal Chemistry Letters, vol. 2, No. 8, pp. 559-564, Aug. 11, 2011.

International Search Report dated Dec. 6, 2012 and issued in corresponding International Patent Application No. PCT/US2012/067908.

* cited by examiner

BIARYL IMIDAZOLE DERIVATIVES FOR REGULATING CYP17

BACKGROUND

Prostate cancer is the most common malignancy for older men and is a major cause of death for that population. Until recently, it was believed that reduction of testosterone was a key component in treating patients diagnosed with prostate cancer. However, a large number of patients having prostate cancer do not respond to reduction of testosterone levels instigated by luteinizing hormone releasing hormone (LHRH) agonists and were thereby dubbed as having "hormone resistant" cancer. Only half of these patients having "hormone-resistant" prostate cancer respond to hormonal treatments.

It is currently recognized that LHRH agonists or antagonists do not completely reduce circulating testosterone levels due to sources other than the testes that can synthesize testosterone, including the adrenal gland and the prostate tumors themselves. The cytochrome P450 (CYP) enzymes include a large family of highly conserved enzymes, including CYP17, that are involved in the synthesis of cholesterol and other bioactive steroids. The fact that these enzymes are involved in steroid hormone biosynthesis has led to recent findings that castration-resistant prostate cancer in men and certain breast cancers in women are responsive to CYP17 inhibition.

CYP17 is a key enzyme in the production of androgenic steroids in many tissues, including prostate tumors, and catalyzes the 17α-hydroxylase reaction and C17,20-lyase reaction of both progesterone and pregnenolone. Inhibition of CYP17 results in reducing the levels of dehydroepiandrostenedione (DHEA) and androstenedione, which are weak androgens and precursors that are subsequently converted to testosterone and dihydrotestosterone by other enzymes.

Designing inhibitors of CYP17 is problematic for several reasons. First, there is limited information regarding the structure of this enzyme. Second, human CYP17 is not available from natural sources, thereby requiring its recombinant generation.

Ketoconazole has been used to inhibit CYP17, but is not very potent and is non-selective since it inhibits other CYP enzymes. Other CYP17 inhibitors have been reported, and the steroidal CYP17 inhibitor Zytiga™ (abiraterone acetate) was recently approved by the U.S. Food and Drug Administration (FDA) for use in combination with prednisone for the treatment of patients with metastatic castration-resistant prostate cancer (CRPC) who have received prior chemotherapy containing docetaxel. Most CYP17 inhibitors, however, including both steroidal compounds such as abiraterone and non-steroidal compounds, have limited selectivity for CYP17, short in vivo half-lives, and/or poor bioavailability.

What is needed are alternative medications for treating prostate and other cancers that function by inhibiting CYP17.

SUMMARY OF THE INVENTION

In one aspect, the present invention provides a compound of formula (I), wherein A, B and $R^1$ are defined herein.

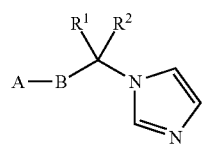

In another aspect, the invention provides a pharmaceutical composition containing a compound of formula (I) and a pharmaceutically acceptable carrier.

In a further aspect, the invention provides a method for regulating CYP17 by administering a therapeutically effective amount of a compound of formula (I) to a patient in need thereof.

In another aspect, the invention provides a method for inhibiting CYP17 activity by administering a therapeutically effective amount of a compound of formula (I) to a patient in need thereof.

In yet another aspect, methods for treating conditions treatable by inhibiting CYP17 activity are provided and include administering a compound of formula (I) to a patient in need thereof.

In a further aspect, methods for treating cancer, such as prostate cancer, are provided and include administering a compound of formula (I) to a patient in need thereof.

In a still further aspect, methods for reducing testosterone production in a patient by administering a therapeutically effective amount of a compound of formula (I) to a patient in need thereof.

Other aspects and advantages of the invention will be readily apparent from the following detailed description of the invention.

DETAILED DESCRIPTION OF THE INVENTION

The invention provides compounds and pharmaceutical composition thereof, which are useful for regulating CYP17 activity and are, therefore, capable of treating conditions associated with abnormal cell proliferation. Specifically, the inventors found that it was the linking of the imidazole ring to a phenyl-heteroaryl or bi-heteroaryl group via a methylene fragment which provided compounds that selectively inhibit CYP17.

The compounds discussed herein are encompassed by the following structure of formula (I):

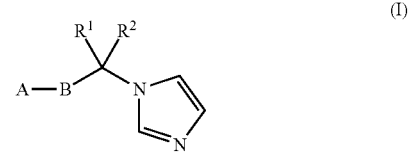

In this structure, A is an optionally substituted phenyl or optionally substituted heteroaryl.

i. In one embodiment, A is of the structure:

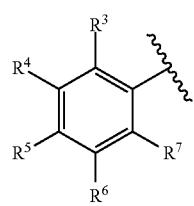

$R^3$, $R^4$, $R^5$, $R^6$ and $R^7$ are, independently, selected from among H, halogen, OH, CN, optionally substituted $C_1$ to $C_6$ alkyl, $C_1$ to $C_6$ alkoxy, amino, ($C_1$ to $C_4$ alkyl)-NH—, ($C_1$ to $C_4$ alkyl)$_2$N—, HCH$_2$NC(O)—, ($C_1$ to $C_4$ alkyl)-NHC(O)—, ($C_1$ to $C_4$ alkyl)$_2$ NC(O)—, HC(O)NH—, ($C_1$ to $C_4$ alkyl)-C(O)NH—COOH, $C_1$ to $C_6$ alkylsulfonyl and —C(O)O($C_1$ to $C_4$ alkyl), with the proviso that 3, 4 or 5 of $R^3$, $R^4$, $R^5$, $R^6$ and $R^7$ are hydrogen.

ii. In a further embodiment, A is the structure noted in i. and $R^3$-$R^7$ are independently selected from among H, OH, F, Cl, CN, $C_1$ to $C_4$ alkyl, $C_1$ to $C_4$ alkoxy, amino, methylamino, dimethylamino, H$_2$NC(O)—, CH$_3$NHC(O)—, (CH$_3$)$_2$NC(O)—, HC(O)NH—, CH$_3$C(O)NH—, COOH, methyl-sulfonyl and —C(O)O($C_1$ to $C_4$ alkyl); with the proviso that 3, 4 or 5 of $R^3$, $R^4$, $R^5$, $R^6$ and $R^7$ are hydrogen iii. In another embodiment, A is of the following structure and $R^5$ is defined above:

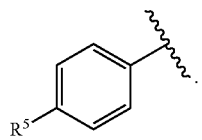

iv. In a further embodiment, A is of the following structure and $R^3$, $R^4$ and $R^5$ are defined above:

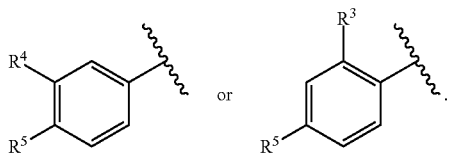

v. In still another embodiment, A is optionally substituted pyridine.

vi. In yet a further embodiment, wherein A is of the following structure:

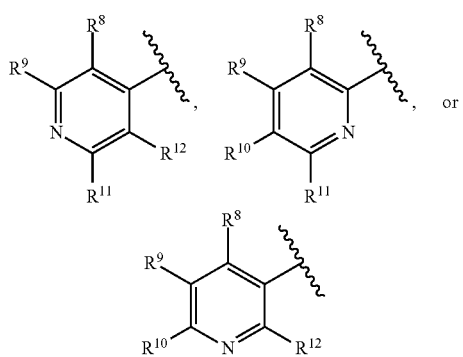

In these structures, $R^8$, $R^9$, $R^{10}$, $R^{11}$, and $R^{12}$ are, independently, selected from among H, halogen, OH, CN, optionally substituted $C_1$ to $C_6$ alkyl, $C_1$ to $C_6$ alkoxy, H$_2$NC(O)—, ($C_1$ to $C_4$ alkyl)-NHC(O)—, ($C_1$ to $C_4$ alkyl)$_2$ NC(O)—, HC(O)NH—, ($C_1$ to $C_4$ alkyl)-C(O)NH—, COOH, $C_1$ to $C_6$ alkylsulfonyl and —C(O)O($C_1$ to $C_4$ alkyl). 2, 3 or 4 of $R^8$, $R^9$, $R^{10}$, $R^{11}$, and $R^{12}$ are hydrogen.

vii. In another embodiment, A is of the following structure and $R^{10}$ is defined in option v:

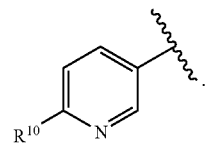

viii. In still a further embodiment, A is optionally substituted pyridone.

ix. In yet another embodiment, A is of the following structure:

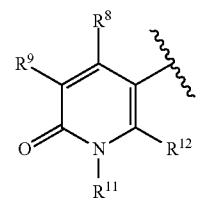

In this structure, $R^8$, $R^9$, $R^{11}$, and $R^{12}$ are, independently, selected from among H, halogen, OH, CN, optionally substituted $C_1$ to $C_6$ alkyl, $C_1$ to $C_6$ alkoxy, H$_2$NC(O)—, ($C_1$ to $C_4$ alkyl)-NHC(O)—, ($C_1$ to $C_4$ alkyl)$_2$ NC(O)—, HC(O)NH—, ($C_1$ to $C_4$ alkyl)-C(O)NH—, COOH, $C_1$ to $C_6$ alkylsulfonyl and —C(O)O($C_1$ to $C_4$ alkyl).

x. In still another embodiment, A is of the following structure and $R^{11}$ is defined above:

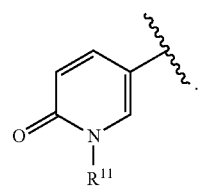

xi. In yet a further embodiment, A is of the structure in option xi and $R^{11}$ is $C_1$ to $C_6$ alkyl.

xii. In another embodiment, A is of the following structure:

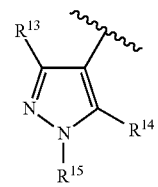

In this structure, $R^{13}$ and $R^{14}$ are, independently, selected from among H, halogen, OH, CN, optionally substituted $C_1$ to $C_6$ alkyl, $C_1$ to $C_6$ alkoxy, H$_2$NC(O)—, ($C_1$ to $C_4$ alkyl)-NHC(O)—, ($C_1$ to $C_4$ alkyl)$_2$ NC(O)—, HC(O)NH—, ($C_1$ to $C_4$ alkyl)-C(O)NH—, COOH, $C_1$ to $C_6$ alkylsulfonyl and —C(O)O($C_1$ to $C_4$ alkyl); and $R^{15}$ is H or $C_1$ to $C_6$ alkyl.

xiii. In still another embodiment, A is of the following structure and $R^{15}$ is defined above:

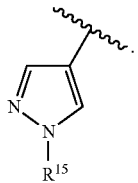

xiv. In a further embodiment, A is of the structure in option xii and $R^{15}$ is H.

xv. In yet another embodiment, A is pyridine, 2-pyridone, furan, or pyrazole, substituted on the ring carbon atoms with 0 to 2 groups independently selected from $CH_3$, $CH_3O$, $CF_3$, F, Cl, and CN; and substituted on the nitrogen atom in 2-pyridone and pyrazole with H or $C_1$ to $C_4$ alkyl.

xvi. In still a further embodiment, A is

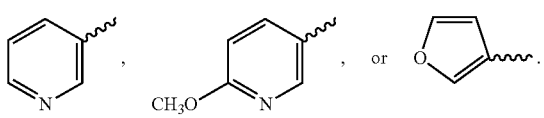

xvii. In another embodiment, A is 2-pyridone or pyrazole and is substituted on the nitrogen atom with H or $C_1$ to $C_4$ alkyl.

xviii. In yet another embodiment, A is

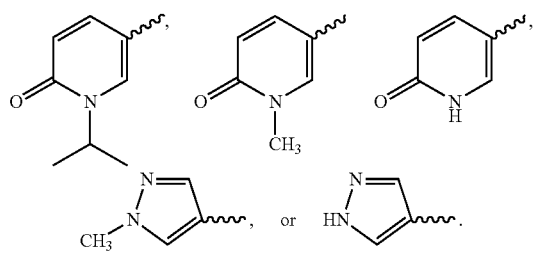

In the compound of formula (I), B is optionally substituted heteroaryl.

a. In one embodiment, B is thiazole, thiophene, pyridine, furan, or thiadiazole.

b. In another embodiment, B is

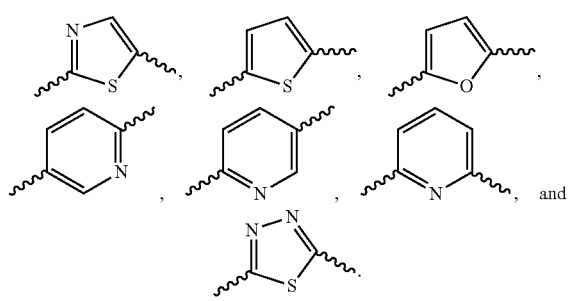

c. In a further embodiment, B is:

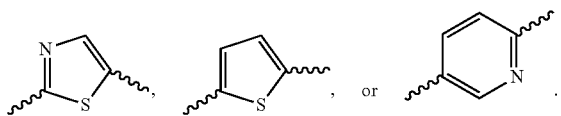

d. In yet another embodiment, $R^1$ is H or $C_1$ to $C_4$ alkyl; $R^2$ is $C_1$ to $C_4$ alkyl; and B is

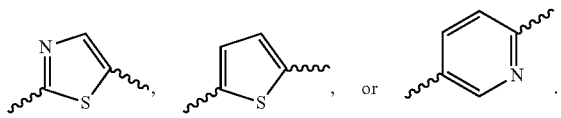

$R^1$ is H or optionally substituted $C_1$ to $C_6$ alkyl. $R^2$ is optionally substituted $C_1$ to $C_6$ alkyl. In one embodiment, $R^1$ is H or $C_1$ to $C_4$ alkyl; and $R^2$ is $C_1$ to $C_4$ alkyl.

In one aspect, A is of the structure:

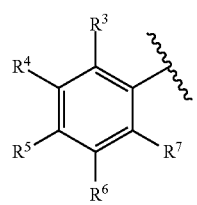

$R^3$, $R^4$, $R^5$, $R^6$ and $R^7$ are independently selected from among H, OH, F, Cl, CN, $C_1$ to $C_4$ alkyl, $C_1$ to $C_4$ alkoxy, amino, methylamino, dimethylamino, $H_2NC(O)$—, $CH_3NHC(O)$—, $(CH_3)_2NC(O)$—, $HC(O)NH$—, $CH_3C(O)NH$—, COOH, methyl-sulfonyl and —$C(O)O(C_1$ to $C_4$ alkyl); $R^1$ is H or $C_1$ to $C_4$ alkyl; and $R^2$ is $C_1$ to $C_4$ alkyl.

In another aspect, A is of the structure:

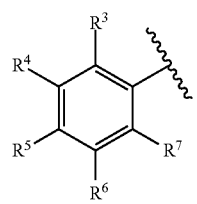

$R^3$, $R^4$, $R^5$, $R^6$ and $R^7$ are independently selected from among H, OH, F, Cl, CN, $C_1$ to $C_4$ alkyl, $C_1$ to $C_4$ alkoxy, amino, methylamino, dimethylamino, $H_2NC(O)$—, $CH_3NHC(O)$—, $(CH_3)_2NC(O)$—, $HC(O)NH$—, $CH_3C(O)NH$—, COOH, methyl-sulfonyl and —$C(O)O(C_1$ to $C_4$ alkyl); $R^1$ is H or $C_1$ to $C_4$ alkyl; $R^2$ is $C_1$ to $C_4$ alkyl; and B is

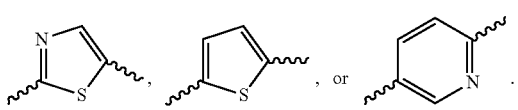

One of skill in the art would readily be able to select the A, B, $R^1$, and $R^2$ groups with the knowledge that stable chemical bonds must be formed. Specifically, one of skill in the art would readily understand which chemical bonds could/could not be formed and how to tailor the reactions in view thereof. The term "stable" as used in this context, refers to a resultant molecule that can be prepared and isolated without degradation.

Some compounds within the present invention possess one or more chiral centers, and the present invention includes each separate enantiomer of such compounds as well as mixtures of the enantiomers. Where multiple chiral centers exist in compounds of the present invention, the invention includes each possible combination of chiral centers within a compound, as well as all possible enantiomeric and diastereomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The following definitions are used in connection with the compounds of the present invention unless the context indicates otherwise. In general, the number of carbon atoms present in a given group is designated "$C_x$-$C_y$", where x and y are the lower and upper limits, respectively. For example, a group designated as "$C_1$-$C_6$" contains from 1 to 6 carbon atoms. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are arrived at by naming from left to right the terminal portion of the functionality followed by the adjacent functionality toward the point of attachment. The structures that are represented here are drawn without any stereochemical indication. It is implied that when a chiral center is present in a molecule, it represent both enantiomers. Terms not defined herein have the meaning commonly attributed to them by those skilled in the art.

"Alkyl" refers to a hydrocarbon chain that may be straight or branched, or to a hydrocarbon group that consists of or contains a cyclic alkyl radical. In one embodiment, an alkyl contains 1 to 8 (inclusive) carbon atoms or integers or ranges there between. In another embodiment, an alkyl contains 1 to 7 (inclusive) carbon atoms or ranges there between. In a further embodiment, an alkyl contains 1 to 6 (inclusive) carbon atoms. In yet another embodiment, an alkyl contains 1 to 5 (inclusive) carbon atoms. In still a further embodiment, an alkyl contains 1 to 4 (inclusive) carbon atoms. Examples of alkyl groups that are hydrocarbon chains include, but are not limited to, methyl, ethyl, propyl, butyl, pentyl, hexyl, and heptyl, where all isomers of these examples are contemplated. Examples of alkyl groups that consist of or contain a cyclic alkyl radical include, but are not limited to, cyclopropyl, cyclobutyl, cyclopentyl, 3,3-dimethylcyclobutyl, (cyclopropyl)methyl, and (cyclopentyl)methyl.

"Optionally substituted alkyl" refers to an alkyl group, as defined above, that is unsubstituted or substituted with one or more F, one or two Cl, one or two OH, one amino group, one (alkyl)amino group (i.e., alkyl-NH—), one (dialkyl)amino group (i.e., (alkyl)$_2$N—), one or two alkoxy groups, or one cyano group, or any combination of these substituents. "Substituted" means that one or more of the alkyl group's hydrogen atoms is replaced with a substituent group as listed above.

"Alkoxy" refers to the group R—O— where R is an alkyl group, as defined above. Exemplary $C_1$-$C_6$ alkoxy groups include but are not limited to methoxy, ethoxy, n-propoxy, i-propoxy, n-butoxy and t-butoxy.

"(Alkoxy)carbonyl-" refers to the group alkyl-O—C(O)—. Exemplary ($C_1$-$C_6$ alkoxy)carbonyl groups include, but are not limited to, methoxy, ethoxy, n-propoxy, 1-propoxy, n-butoxy and t-butoxy.

"(Alkyl)amido-" refers to the group —C(O)NH-alkyl. Representative examples of ($C_1$-$C_6$ alkyl)amido include, but are not limited to, —C(O)NHCH$_3$, —C(O)NHCH$_2$CH$_3$, —C(O)NHCH$_2$CH$_2$CH$_3$, —C(O)NHCH$_2$CH$_2$CH$_2$CH$_3$, —C(O)NHCH$_2$CH$_2$CH$_2$CH$_2$CH$_3$, —C(O)NHCH(CH$_3$)$_2$, —C(O)NHCH$_2$CH(CH$_3$)$_2$, —C(O)NHCH(CH$_3$)CH$_2$CH$_3$, —C(O)NH—C(CH$_3$)$_3$ and —C(O)NHCH$_2$C(CH$_3$)$_3$.

"Di(alkyl)amido-" refers to a —C(O)—N group in which the nitrogen atom of the group is attached, independently, to alkyl groups, as defined above. Each alkyl group can be independently selected. Representative examples of ($C_1$-$C_6$ alkyl)$_2$ amido include, but are not limited to, —C(O)N(CH$_3$)$_2$, —C(O)N(CH$_2$CH$_3$)$_2$, —C(O)N(CH$_2$CH$_2$CH$_3$)$_2$, —C(O)N(CH$_2$CH$_2$CH$_2$CH$_3$)$_2$, —C(O)N(CH$_2$CH$_2$CH$_2$CH$_2$CH$_3$)$_2$, —C(O)N(CH$_3$)(CH$_2$CH$_3$), and —C(O)N(CH$_2$CH$_3$)(CH$_2$CH$_2$CH$_3$).

"Alkylsulfonyl" refers to an alkyl-S(O)$_2$— group. Representative examples of ($C_1$-$C_6$ alkyl)sulfonyl group are, but are not limited to, CH$_3$S(O)$_2$— and CH$_3$CH$_2$S(O)$_2$—.

"(Alkyl)amino-" refers to an alkyl-NH— group. Representative examples of ($C_1$-$C_6$ alkyl)amino group are, but are not limited to, CH$_3$NH—, CH$_3$CH$_2$NH—, CH$_3$CH$_2$CH$_2$NH—, CH$_3$CH$_2$CH$_2$CH$_2$NH—, (CH$_3$)$_2$CHNH—, (CH$_3$)$_2$CHCH$_2$NH—, CH$_3$CH$_2$CH(CH$_3$)NH— and (CH$_3$)$_3$CNH—.

"(Dialkyl)amino-" refers to an (alkyl)$_2$N— group, wherein the two alkyl groups are independently selected. Representative examples of di($C_1$-$C_6$ alkyl)amino include, but are not limited to (CH$_3$)$_2$N—, (CH$_3$CH$_2$)$_2$N—, (CH$_3$CH$_2$CH$_2$)$_2$N—, (CH$_3$)(CH$_2$CH$_3$)$_2$N—, (CH$_3$)(CH$_2$CH$_2$CH$_3$)N—, and (CH$_3$CH$_2$)(CH$_2$CH$_2$CH$_3$)N—.

"Alkylcarboxy-" refers to an alkyl group, defined above that is attached to the parent structure through the carbon atom of a carboxy (C(O)—O—) functionality. Examples of ($C_1$-$C_6$ alkyl)carboxy include acetoxy, propionoxy, propylcarboxy, and isopentylcarboxy.

"(Alkyl)carboxamido-" refers to a —NHC(O)-alkyl-group in which the carbonyl carbon atoms of the group is attached to an alkyl group. Representative examples of ($C_1$-$C_6$ alkyl)carboxamido include, but are not limited to, —NHC(O)CH$_3$, N(CH$_3$)C(O)CH$_3$, —N(CH$_3$)C(O)CH$_2$CH$_3$, —N(CH$_3$)C(O)CH$_2$CH$_2$CH$_3$, —N(CH$_3$)C(O)CH$_2$CH$_2$CH$_2$CH$_3$, —N(CH$_2$CH$_3$)C(O)CH$_2$CH$_2$CH$_2$CH$_3$, —N(CH$_2$CH$_3$)C(O)CH(CH$_3$)$_2$, —N(CH$_2$CH$_3$)C(O)CH$_2$CH(CH$_3$)$_2$, —N(CH$_2$CH$_3$)C(O)CH(CH$_3$)CH$_2$CH$_3$, and —N(CH$_2$CH$_3$)C(O)C(CH$_3$)$_3$.

"Optionally substituted phenyl" refers to a phenyl group that can be unsubstituted or substituted with one or more of optionally substituted alkyl, halogen, OH, NH$_2$, alkylamino-, di(alkyl)amino-, cyano, COOH, (alkoxy)carbonyl-, alkylcarboxy-, (alkyl)carboxamido-, alkylsulfonyl, —C(O)NH$_2$, (alkyl)amido-, di(alkyl)amido-, NO$_2$, or alkoxy.

"Halo" or "halogen" refers to F, Cl, Br and I.

"Heteroaryl" refers to a monocyclic 5-membered or 6-membered aromatic ring system containing at least one ring atom selected from the heteroatoms oxygen, sulfur and nitrogen. Examples of heteroaryl groups include furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3,4-oxadiazole, 1,2,4-triazole, 1-methyl-1,2,4-triazole, 1H-tetrazole, 1-methyltetrazole, and pyridone, including 2-pyridone.

"Optionally substituted heteroaryl" refers to a heteroaryl group, as defined above, that is unsubstituted or substituted with one or more of optionally substituted alkyl, F, Cl, OH, $NH_2$, alkylamino-, di(alkyl)amino-, cyano, COOH, (alkoxy) carbonyl-, alkylcarboxy-, (alkyl)carboxamido-, alkylsulfonyl, —$C(O)NH_2$, (alkyl)amido-, di(alkyl)amido-, $NO_2$, or alkoxy.

A "subject" is a mammal, e.g., a human, mouse, rat, guinea pig, dog, cat, horse, cow, pig, or non-human primate, such as a monkey, chimpanzee, baboon or gorilla.

Representative "pharmaceutically acceptable salts" include but are not limited to, e.g., water-soluble and water-insoluble salts, including salts of acids. Examples of acids which can form salts with the compounds discussed herein include, without limitation, acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, trifluoroacetic, and camphorsulfonic.

In a further embodiment, a compound of the invention may be a solvate. As used herein, a solvate does not significantly alter the physiological activity or toxicity of the compounds, and as such may function as pharmacological equivalents to non-solvate compounds of the invention. The term "solvate" as used herein is a combination, physical association and/or solvation of a compound of the present invention with a solvent molecule. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates.

Some compounds within the present invention possess one or more chiral centers, and the present invention includes each separate enantiomer of such compounds as well as mixtures of the enantiomers. Where multiple chiral centers exist in compounds of the present invention, the invention includes each possible combination of chiral centers within a compound, as well as all possible enantiomeric mixtures thereof. All chiral, diastereomeric, and racemic forms of a structure are intended, unless the specific stereochemistry or isomeric form is specifically indicated. It is well known in the art how to prepare optically active forms, such as by resolution of racemic forms or by synthesis from optically active starting materials.

The words "comprise", "comprises", and "comprising" are to be interpreted inclusively rather than exclusively. The works "consist", "consisting", and its variants, are to be interpreted exclusively, rather than inclusively.

As used herein, the term "about" means a variability of 10% from the reference given, unless otherwise specified.

Processes for Preparing the Compounds

Methods useful for making the compounds of formula (I) are set forth in the Examples below and generalized in the schemes. One of skill in the art will recognize that the schemes can be adapted to produce the other compounds of formula (I) and pharmaceutically acceptable salts of compounds of formula (I).

In the following reactions described to prepare compounds described herein, it can be necessary to protect reactive functional groups, for example OH, amino, imino, thio or carboxy groups, where these are desired in the final product, to avoid their unwanted participation in the reactions. Conventional protecting groups can be used in accordance with standard practices, for example, see T. W. Green and P. G. M. Wuts in "Protective Groups in Organic Chemistry", John Wiley & Sons, 1991.

The following methods outline the synthesis of the compounds of formula (I). The following examples are presented to illustrate certain embodiments of the present invention, but should not be construed as limiting the scope of the invention.

In the following reactions described to prepare compounds of this invention, it can be necessary to protect reactive functional groups, for example hydroxyl, amino, imino, thio or carboxy groups, where these are desired in the final product, to avoid their unwanted participation in the reactions. Conventional protecting groups can be used in accordance with standard practices, for example, see T. W. Green and P. G. M. Wuts in "Protective Groups in Organic Chemistry", John Wiley & Sons, 1991.

The following methods outline the synthesis of the compounds of Formula I. The following examples are presented to illustrate certain embodiments of the present invention, but should not be construed as limiting the scope of the invention.

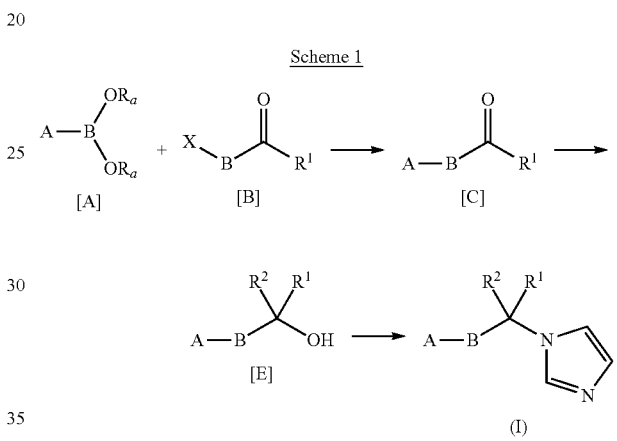

Scheme 1

Scheme 1 depicts one synthesis method to prepare compounds of formula (I). Specifically, a boronic acid or boronate ester is first coupled to a heteroaryl halide. In one embodiment, the boronic acid is compound [A] when $R_a$=H. In another embodiment, the boronate ester is compound [A] when $R_a$=alkyl. In still another embodiment, the boronate ester is a boronic acid pinacol ester. In a further embodiment, the heteroaryl halide is compound [B]. This reaction may be performed in the presence of a weak base, a palladium catalyst, in a solvent. One of skill in the art would be able to select a suitable weak base, palladium catalyst, and solvent for use in this reaction. In one embodiment, the weak base is KOAc or $Na_2CO_3$. In another embodiment, the palladium catalyst is $Pd(PPh_3)_4$, $Pd(dppf)Cl_2$ DCM or $Pd(dppf)Cl_2$. In a further embodiment, the solvent is toluene/ethanol, 1,4-dioxane, DMF, or mixtures thereof. The reaction may be performed or at elevated temperatures up to the reflux temperature of the solvent. The intermediate [C] is then reduced to form the corresponding alcohol compound [E]. In one embodiment, the reduction is performed with an alkyl metal reagent or an alkyl lithium reagent. In one embodiment, the alkyl metal reagent is compound [D]. In another embodiment, the alkyl metal reagent is a Grignard reagent $R^2$-MX, where M is Mg and X is halide such as Cl or Br. In a further embodiment, the reduction is performed using an alkyl lithium reagent $R^2$-M, wherein M is Li. Intermediate [E] is then substituted with an imidazole group. In one embodiment, intermediate E is reacted with carbonyl diimidazole [F] to produce the compound of formula (I).

Scheme 1A

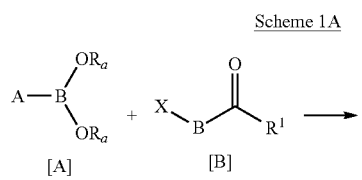

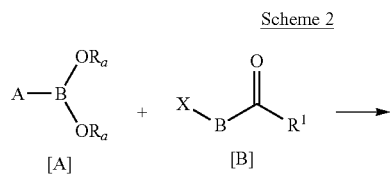

Scheme 1A describes another embodiment for preparing compounds of formula (I). In these scheme, a boronic acid A when ($R_a$=H) or boronate ester A (when $R_a$=alkyl) is reacted with heteroaryl halide compound B in the presence of weak base, a palladium catalyst, in a solvent to provide intermediate C. The intermediate [C] is then reacted with alkyl metal reagent compound D. Intermediate [E] is then substituted with an imidazole group using carbonyl diimidazole [F] produce the compound of formula (I).

Scheme 2

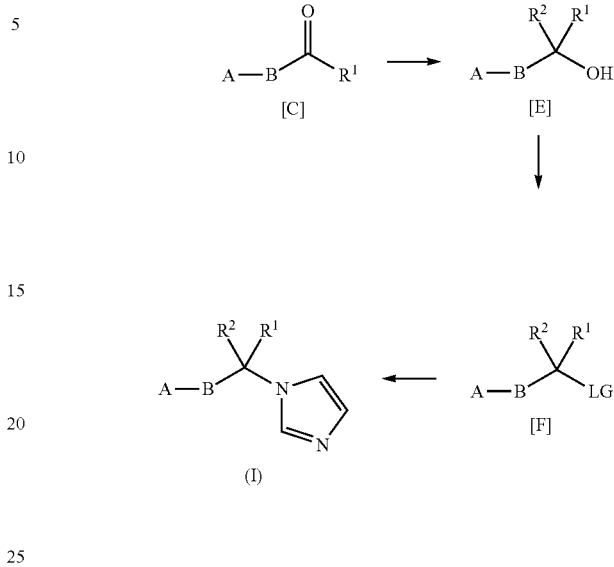

Scheme 2 provides a method wherein compounds of formula (I) are prepared via alcohol intermediate [E] prepared as described in Scheme 1. The hydroxy functionality in [E] is then converted into a suitable leaving group (LG) to provide intermediate [F]. In one embodiment, the leaving group is a bromide, chloride, tosylate, or mesylate. In a further embodiment, intermediate [E] is reacted with a brominating agent such as $PBr_3$ or $PBr_5$ to afford the corresponding bromide compound, namely intermediate [F] wherein LG is Br. In another embodiment, intermediate [E] is reacted with a sulfonyl chloride such as 4-toluenesulfonyl chloride or methanesulfonyl chloride to form the corresponding 4-toluenesulfonate (tosylate) or methanesulfonate (mesylate), respectively, namely intermediate [F] wherein LG is 4-$CH_3C_6H_4S(O)_2$— or $CH_3S(O)_2$—, respectively. Intermediate [F] is then reacted with imidazole [G] to produce compounds of formula (I).

Scheme 2A

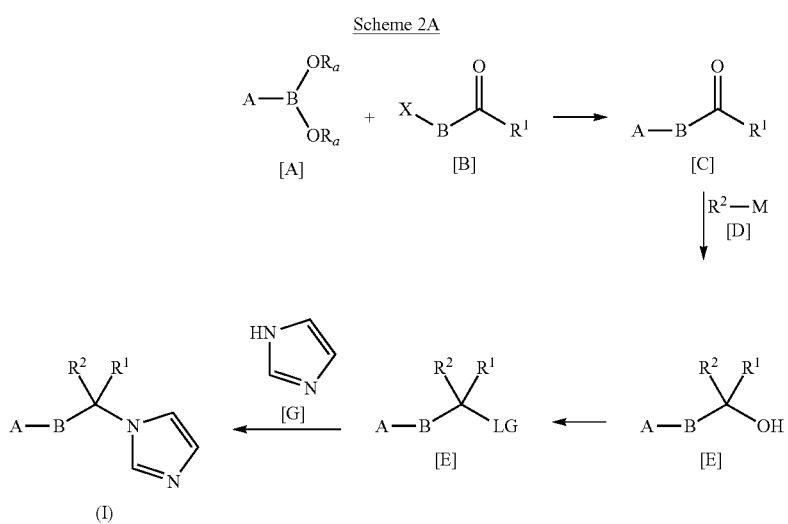

Scheme 2A provides a method wherein compounds of formula (I) are prepared via alcohol intermediate [E] prepared as described in Scheme 1. The hydroxy functionality in [E] is converted into a suitable leaving group (LG) to provide intermediate [F]. In one embodiment, the leaving group is a bromide, chloride, tosylate, or mesylate. In a further embodiment, intermediate [E] is reacted with $PBr_3$, or $PBr_5$, 4-toluenesulfonyl chloride or methanesulfonyl chloride to form intermediate [F]. Intermediate [F] is then reacted with imidazole [G] to produce compounds of formula (I).

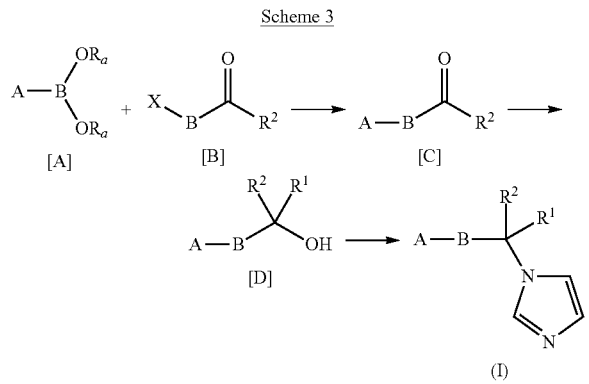

Scheme 3

Scheme 3 provides a method wherein compounds of formula (I) are prepared, by first preparing alkyl ketone intermediate [C] by the methods described in Scheme 1. These compounds C are then reduced to provide alcohol intermediate [D] wherein $R^1$ is hydrogen. The reduction can be performed by one skilled in the art using any number of various suitable reducing agents. In one embodiment, the reducing agent is $NaBH_4$ or $LiAlH_4$. Alcohol intermediate [D] is then converted to compounds of formula (I) by the method described in Scheme 1.

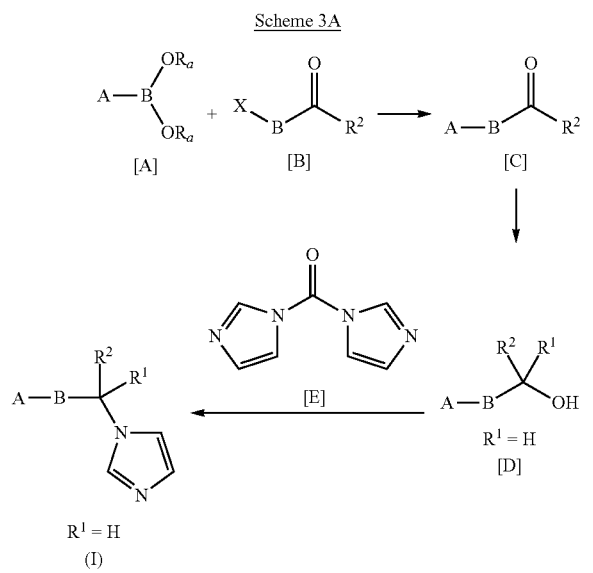

Scheme 3A

Scheme 3A provides a method wherein compounds of formula (I) are prepared via alkyl ketone intermediate [C]. In this scheme, ketone intermediate [C] is reduced using $NaBH_4$ or $LiAlH_4$ to provide alcohol intermediate [D] wherein $R^1$ is hydrogen. Alcohol intermediate [D] is then converted to compounds of Formula I by the method described in Scheme 1.

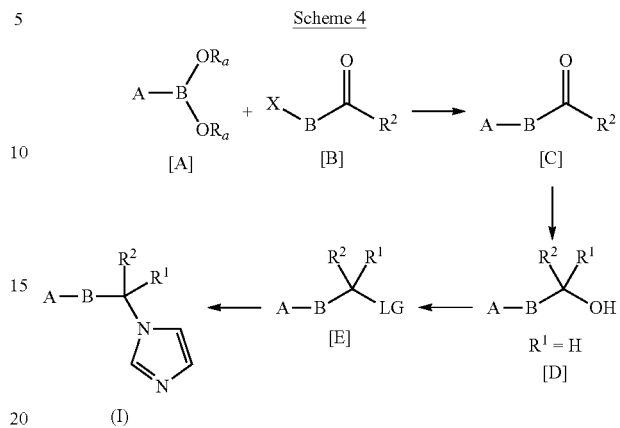

Scheme 4

Scheme 4 provides another method for preparing compounds of formula (I). In this route, alkyl ketone intermediate [C] are first prepared using the methods of Scheme 1. Alkyl ketone intermediate [C] is then reduced to provide alcohol intermediate [D] wherein $R^1$ is hydrogen using the description provided in Scheme 3. The hydroxy functionality in compound [D] is then converted into a suitable leaving group (LG) to provide intermediate [E] using by the route in Scheme 3. Finally, intermediate [E] is converted to the compounds of formula (I). In one embodiment, compound [E] is converted to the compound of formula (I) using imidazole.

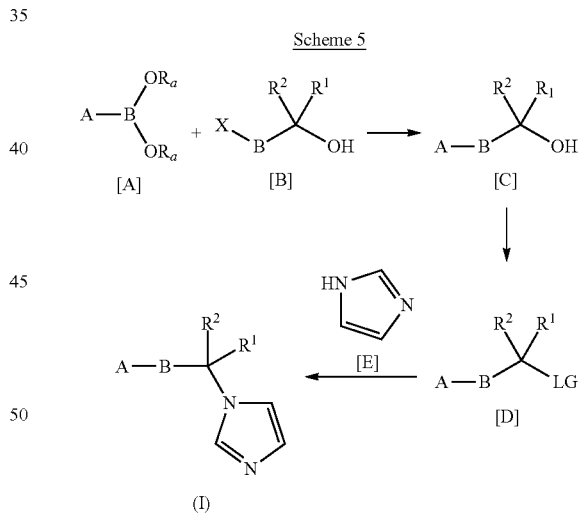

Scheme 5

Scheme 5 depicts another method for preparing compounds of formula (I) prepared. In this route, a boronic acid ($R_a$=H) or boronate ester ($R_a$=alkyl) derivative [A] is first coupled to a heteroaryl halide. In embodiment, the heteroaryl halide is compound [B]. In another embodiment, the heteroaryl halide compound [B] contains a hydroxy alkyl substituent. This coupling reaction may be performed as described for Scheme 1, using a boronic acid pinacol ester derivative [A], for example. The reaction may be performed in the presence of a weak base, palladium catalyst, or solvent as described in Scheme 1. The hydroxy functional group in compound [C] is then converted to a suitable leaving group by the methods described for Scheme 2 to provide intermediate [D]. Intermediate [D] is then converted to the compound of formula (I) by the methods described for Scheme 2.

be replaced with a coupling reaction as depicted in Scheme 7. In this case, a phenyl or heteroaryl halide [A] is reacted with a boronic acid ($R_a$=H) or boronate ester ($R_a$=alkyl) derivative

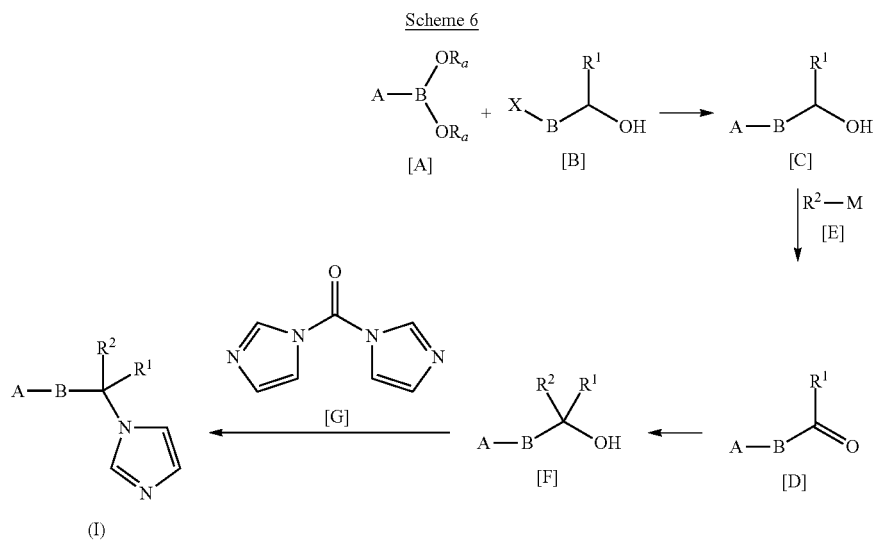

Scheme 6 depicts another method for the synthesis of compounds of formula (I). In this example, alcohol intermediate [C] is prepared as described in Scheme 5. Intermediate [C] is then oxidized. In one embodiment, the oxidation is performed using an oxidizing agent which may be selected by one skilled in the art. In another embodiment, the oxidizing agent is the Dess-Martin periodinane. By doing so, the oxidation results in the preparation of ketone or aldehyde intermediate [D]. Compound [D] is $R^2$-substituted to form compound [F]. The $R^2$-substitution is performed using an alkylating agent. In one embodiment, the alkylating agent is alkyl metal reagent [E] as described for Scheme 1. Intermediate [F] may be converted to compounds of formula (I) by the methods described for Scheme 1.

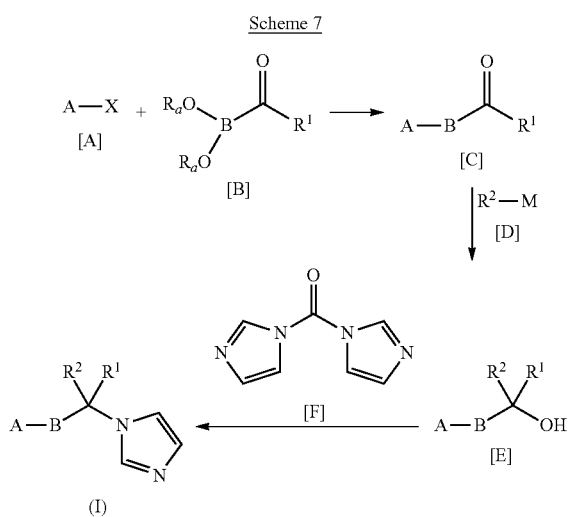

It will be recognized by those skilled in the art that the coupling methods used to form a bond between fragment A and B, as described in the Schemes 1 to 6, can in some cases

[B]. The coupling reaction is carried out by using the methods as described for Scheme 1. The intermediate [C] that is formed can be converted to compounds of formula (I) by the methods described for Scheme 1 (as also depicted in Scheme 7), or by the methods described for Schemes 2 to 4.

It will also be recognized by those skilled in the art that in certain cases the substituents on fragments A, B, $R^1$ and $R^2$ can be converted into different substituents, during the course of the synthetic sequences as depicted in Schemes 1 to 7. Likewise, in certain cases the substituents on fragments A, B, $R^1$ and $R^2$ can be modified after the preparation of compounds of the invention of Formula I, to produce additional compounds of formula (I). Likewise, some substituents can be converted into hydrogen, to afford the corresponding derivative that is unsubstituted at that atom position. Examples of such reactions to convert one substituent into a different substituent include, but are not limited to: the demethylation of a methoxy substituent by treatment with $BBr_3$ to produce a hydroxy substituent; the reduction of a nitro substituent by hydrogenation over Pd/C catalyst to produce an amino substituent; the acylation of an amino substituent to produce N-acylated amino substituent; the N-alkylation of a pyridone or pyrazole nitrogen atom by reaction with an alkyl iodide; the hydrolysis of a carboxylate ester substituent by treatment with lithium hydroxide to produce the carboxylic acid; the alkylation of a hydroxy substituent by reaction with an alkyl halide to produce the related alkoxy substituent; the conversion of a halide substituent into an alkoxy substituent by reaction with a metal alkoxide; and the hydrolysis of an N-tert-butoxycarbonyl group on a nitrogen atom to produce the corresponding compound wherein the nitrogen atom is substituted with hydrogen or is considered to be unsubstituted.

It will also be recognized by those skilled in the art that a wide variety of synthetic methods are known in the art that can be used for the preparation of the starting material derivatives of fragments A and B that are depicted in Schemes 1 to 7.

Pharmaceutical compositions useful herein contain a compound of formula (I) in a pharmaceutically acceptable carrier optionally with other pharmaceutically inert or inactive ingredients. In another embodiment, a compound of formula (I) is present in a single composition. In a further embodiment, a compound of formula (I) is combined with one or more excipients and/or other therapeutic agents as described below.

The pharmaceutical compositions of the invention comprise an amount of a compound of formula (I) or a pharmaceutically acceptable salt thereof that is effective for regulating CYP17 activity in a subject. Specifically, the dosage of the compound of formula (I) to achieve a therapeutic effect will depend on the formulation, age, weight and sex of the patient and route of delivery. it is also contemplated that the treatment and dosage of the compound of formula (I) may be administered in unit dosage form and that one skilled in the art would adjust the unit dosage form accordingly to reflect the relative level of activity. The decision as to the particular dosage to be employed (and the number of times to be administered per day) is within the discretion of the ordinarily-skilled physician, and may be varied by titration of the dosage to the particular circumstances to produce the desired therapeutic effect. In one embodiment, the therapeutically effective amount is about 0.01 mg/kg to 10 mg/kg body weight. In another embodiment, the therapeutically effective amount is less than about 5 g/kg, about 500 mg/kg, about 400 mg/kg, about 300 mg/kg, about 200 mg/kg, about 100 mg/kg, about 50 mg/kg, about 25 mg/kg, about 10 mg/kg, about 1 mg/kg, about 0.5 mg/kg, about 0.25 mg/kg, about 0.1 mg/kg, about 100 µg/kg, about 75 µg/kg, about 50 µg/kg, about 25 µg/kg, about 10 µg/kg, or about 1 µg/kg. However, the therapeutically effective amount of the compound of formula (I) can be determined by the attending physician and depends on the condition treated, the compound administered, the route of delivery, the age, weight, severity of the patient's symptoms and response pattern of the patient.

The therapeutically effective amounts may be provided on regular schedule, i.e., daily, weekly, monthly, or yearly basis or on an irregular schedule with varying administration days, weeks, months, etc. Alternatively, the therapeutically effective amount to be administered may vary. In one embodiment, the therapeutically effective amount for the first dose is higher than the therapeutically effective amount for one or more of the subsequent doses. In another embodiment, the therapeutically effective amount for the first dose is lower than the therapeutically effective amount for one or more of the subsequent doses. Equivalent dosages may be administered over various time periods including, but not limited to, about every 2 hours, about every 6 hours, about every 8 hours, about every 12 hours, about every 24 hours, about every 36 hours, about every 48 hours, about every 72 hours, about every week, about every two weeks, about every three weeks, about every month, and about every two months. The number and frequency of dosages corresponding to a completed course of therapy will be determined according to the judgment of a health-care practitioner. The therapeutically effective amounts described herein refer to total amounts administered for a given time period; that is, if more than one compound of formula (I) or a pharmaceutically acceptable salt thereof is administered, the therapeutically effective amounts correspond to the total amount administered.

The pharmaceutical compositions containing a compound of formula (I) may be formulated neat or with one or more pharmaceutical carriers for administration. The amount of the pharmaceutical carrier(s) is determined by the solubility and chemical nature of the compound of formula (I), chosen route of administration and standard pharmacological practice. The pharmaceutical carrier(s) may be solid or liquid and may incorporate both solid and liquid carriers. A variety of suitable liquid carriers is known and may be readily selected by one of skill in the art. Such carriers may include, e.g., dimethylsulfoxide (DMSO), saline, buffered saline, hydroxypropylcyclodextrin, and mixtures thereof. Similarly, a variety of solid carriers and excipients are known to those of skill in the art. The compounds of formula (I) may be administered by any route, taking into consideration the specific condition for which it has been selected. The compounds of formula (I) may, be delivered orally, by injection, inhalation (including orally, intranasally and intratracheally), ocularly, transdermally, intravascularly, subcutaneously, intramuscularly, sublingually, intracranially, epidurally, intravesically, rectally, and vaginally, among others.

Although the compound of formula (I) may be administered alone, it may also be administered in the presence of one or more pharmaceutical carriers that are physiologically compatible. The carriers may be in dry or liquid form and must be pharmaceutically acceptable. Liquid pharmaceutical compositions are typically sterile solutions or suspensions. When liquid carriers are utilized for parenteral administration, they are desirably sterile liquids. Liquid carriers are typically utilized in preparing solutions, suspensions, emulsions, syrups and elixirs. In one embodiment, the compound of formula (I) is dissolved a liquid carrier. In another embodiment, the compound of formula (I) is suspended in a liquid carrier. One of skill in the art of formulations would be able to select a suitable liquid carrier, depending on the route of administration. The compound of formula (I) may alternatively be formulated in a solid carrier. In one embodiment, the composition may be compacted into a unit dose form, e.g., tablet or caplet. In another embodiment, the composition may be added to unit dose form, e.g., a capsule. In a further embodiment, the composition may be formulated for administration as a powder. The solid carrier may perform a variety of functions, e.g., may perform the functions of two or more of the excipients described below. For example, solid carrier may also act as a flavoring agent, lubricant, solubilizer, suspending agent, filler, glidant, compression aid, binder, disintegrant, or encapsulating material.

The composition may also be sub-divided to contain appropriate quantities of the compound of formula (I). For example, the unit dosage can be packaged compositions, e.g., packeted powders, vials, ampoules, prefilled syringes or sachets containing liquids.

Examples of excipients which may be combined with one or more compound of formula (I) include, without limitation, adjuvants, antioxidants, binders, buffers, coatings, coloring agents, compression aids, diluents, disintegrants, emulsifiers, emollients, encapsulating materials, fillers, flavoring agents, glidants, granulating agents, lubricants, metal chelators, osmo-regulators, pH adjustors, preservatives, solubilizers, sorbents, stabilizers, sweeteners, surfactants, suspending agents, syrups, thickening agents, or viscosity regulators. See, for example, the excipients described in the "Handbook of Pharmaceutical Excipients", 5$^{th}$ Edition, Eds.: Rowe, Sheskey, and Owen, APhA Publications (Washington, D.C.), Dec. 14, 2005, which is incorporated herein by reference.

In one embodiment, the compositions may be utilized as inhalants. For this route of administration, compositions may be prepared as fluid unit doses using a compound of formula (I) and a vehicle for delivery by an atomizing spray pump or by dry powder for insufflation.

In another embodiment, the compositions may be utilized as aerosols, i.e., oral or intranasal. For this route of administration, the compositions are formulated for use in a pressurized aerosol container together with a gaseous or liquefied propellant, e.g., dichlorodifluoromethane, carbon dioxide, nitrogen, propane, and the like. Also provided is the delivery of a metered dose in one or more actuations.

In another embodiment, the compositions may be administered by a sustained delivery device. "Sustained delivery" as used herein refers to delivery of a compound of formula (I) which is delayed or otherwise controlled. Those of skill in the art know suitable sustained delivery devices. For use in such sustained delivery devices, the compound of formula (I) is formulated as described herein.

In addition to the components described above for use in the composition and the compound of formula (I), the compositions may contain one or more medications or therapeutic agents which are used to treat solid tumors. In one embodiment, the medication is a chemotherapeutic, including but not limited to cytotoxic/cytostatic agents and targeted agents such as include LHRH agonist/antagonists, androgen receptor antagonists, kinase or other enzyme inhibitors, and the like. Examples of chemotherapeutics include those recited in the "Physician's Desk Reference", 64$^{th}$ Edition, Thomson Reuters, 2010, which is hereby incorporated by reference. In one embodiment, the compounds of formula (I) can be administered with other inhibitors of CYP17, such as abiraterone acetate, or with compounds that suppress testosterone production, such as LHRH agonists/antagonists. Therapeutically effective amounts of the additional medication(s) or therapeutic agents are well known to those skilled in the art. However, it is well within the attending physician to determine the amount of other medication to be delivered.

The compounds of formula (I) and/or other medication(s) or therapeutic agent(s) may be administered in a single composition. However, the present invention is not so limited. In other embodiments, the compounds of formula (I) may be administered in one or more separate formulations from other compounds of formula (I), chemotherapeutic agents, or other agents as is desired.

Also provided herein are kits or packages of pharmaceutical formulations containing the compounds of formula (I) or compositions described herein. The kits may be organized to indicate a single formulation or combination of formulations to be taken at each desired time.

Suitably, the kit contains packaging or a container with the compound of formula (I) formulated for the desired delivery route. Suitably, the kit contains instructions on dosing and an insert regarding the active agent. Optionally, the kit may further contain instructions for monitoring circulating levels of product and materials for performing such assays including, e.g., reagents, well plates, containers, markers or labels, and the like. Such kits are readily packaged in a manner suitable for treatment of a desired indication. For example, the kit may also contain instructions for use of a spray pump or other delivery device. Other suitable components to include in such kits will be readily apparent to one of skill in the art, taking into consideration the desired indication and the delivery route.

The compounds of formula (I) or compositions described herein can be a single dose or for continuous or periodic discontinuous administration. For continuous administration, a package or kit can include the compound of formula (I) in each dosage unit (e.g., solution, lotion, tablet, pill, or other unit described above or utilized in drug delivery), and optionally instructions for administering the doses daily, weekly, or monthly, for a predetermined length of time or as prescribed. When the compound of formula (I) is to be delivered periodically in a discontinuous fashion, a package or kit can include placebos during periods when the compound of formula (I) is not delivered. When varying concentrations of a composition, of the components of the composition, or the relative ratios of the compounds of formula (I) or agents within a composition over time is desired, a package or kit may contain a sequence of dosage units which provide the desired variability.

A number of packages or kits are known in the art for dispensing pharmaceutical agents for periodic oral use. In one embodiment, the package has indicators for each period. In another embodiment, the package is a labeled blister package, dial dispenser package, or bottle.

The packaging means of a kit may itself be geared for administration, such as an inhaler, syringe, pipette, eye dropper, or other such apparatus, from which the formulation may be applied to an affected area of the body, such as the lungs, injected into a subject, or even applied to and mixed with the other components of the kit.

The compositions of these kits also may be provided in dried or lyophilized forms. When reagents or components are provided as a dried form, reconstitution generally is by the addition of a suitable solvent. It is envisioned that the solvent also may be provided in another package.

The kits of the present invention also will typically include a means for containing the vials in close confinement for commercial sale such as, e.g., injection or blow-molded plastic containers into which the desired vials are retained.

Irrespective of the number or type of packages and as discussed above, the kits also may include, or be packaged with a separate instrument for assisting with the injection/administration or placement of the composition within the body of an animal. Such an instrument may be an inhaler, syringe, pipette, forceps, measuring spoon, eye dropper or any such medically approved delivery means.

In one embodiment, a kit is provided and contains a compound of formula (I). The compound of formula (I) may be in the presence or absence of one or more of the carriers or excipients described above. The kit may optionally contain instructions for administering the medication and the compound of formula (I) to a subject having a disease associated with CPY17 activity.

In a further embodiment, a kit is provided and contains a compound of formula (I) in a second dosage unit, and one or more of the carriers or excipients described above in a third dosage unit. The kit may optionally contain instructions for administering the medication and the compound of formula (I) to a subject having a disease associated with CPY17 activity.

The compounds described herein are useful in treating conditions which are associated with CPY17 activity. In one embodiment, such a disease is associated with abnormal cellular proliferation, particularly the abnormal proliferation of cells which is sensitive to hormones such as testosterone or estrogen. The term "abnormal cellular proliferation" refers to the uncontrolled growth of cells which are naturally present in a mammalian body. In one embodiment, a disease which is characterized by abnormal cellular proliferation is cancer, including, without limitation, cancer of the prostate, head, neck, eye, mouth, throat, esophagus, bronchus, larynx, pharynx, chest, bone, lung, colon, rectum, stomach, bladder, uterus, cervix, breast, ovaries, vagina, testicles, skin, thyroid, blood, lymph nodes, kidney, liver, intestines, pancreas, brain, central nervous system, adrenal gland, or skin or a leukemia. In one embodiment, the disease characterized by abnormal cellular proliferation is cancer of the prostate.

The term "regulation" or variations thereof as used herein refers to the ability of a compound of formula (I) to inhibit one or more components of a biological pathway. In one embodiment, "regulation" refers to inhibition of CPY17 activity.

In one embodiment, methods for inhibiting CPY17 activity are provided which comprise administering a therapeutically effective amount of a compound of formula (I) to a patient in need thereof.

In another desirable embodiment, methods for treating a disease characterized by an abnormal cellular growth resulting from CPY17 activity are provided which comprise administering of a therapeutically effective amount of a compound of formula (I) to a patient in need thereof.

In a further desirable embodiment, methods for treating a condition treatable by inhibiting CPY17 activity are provided which comprise administering a therapeutically effective amount of a compound of formula (I) to a patient in need thereof.

In still another embodiment, methods for treating cancer are provided which comprise administering a therapeutically effective amount of a compound of formula (I) to a patient in need thereof.

In yet a further embodiment, methods for treating prostate cancer are provided which comprise administering a therapeutically effective amount of a compound of formula (I) to a patient in need thereof.

In a still further embodiment, methods of reducing testosterone production in a patient are provided which comprise administering a therapeutically effective amount of a compound of formula (I) in need thereof.

As described herein, a therapeutically effective amount of a compound when used for the treatment of cancer is an amount which may reduce the number of cancer cells (cytotoxic), allow the number of cancer cells to remain relatively constant (cytostatic), reduce tumor size, inhibit metastasis, inhibit tumor growth and/or ameliorate one or more of the symptoms of the cancer. For cancer therapy, efficacy can be measured for example, by assessing the time to disease progression, measuring tumor size and/or determining the patient response rate.

The following examples are illustrative only and are not intended to limit the present invention.

EXAMPLES

All reactions were carried out under nitrogen or argon atmosphere unless otherwise specified. Unless otherwise stated, all the raw starting materials, solvents and reagents were purchased from commercial sources (e.g., Avocado Research Chemicals, Apollo Scientific Limited, Bepharma Ltd., Combi-Blocks Inc., Sigma Aldrich Chemicals Pvt. Ltd., Ultra Labs, Toronto Research Chemicals Inc., Chemical House, RFCL Limited, Spectro Chem. Pvt. Ltd., Leonid Chemicals, Loba Chemie, Changzhou Yangyuan, NeoSynth., Rankem) and used as such without further purification or reagents can be synthesizes by procedures known in the art. Biotage Isolera One and Combi Flash Tele Dyne Isco Automated Flash Purification System were used for the purification of crude products using the eluent combination mentioned in the respective procedures. Flash Chromatography was performed using silica gel (60-100, 100-200 and 230-400 mesh) from Chemlabs, with Nitrogen and/or compressed air. Preparative thin-layer chromatography was carried out using silica gel GF 1500 µM 20×20 cm and GF 2000 µM 20×20 cm Prep-scored plates from Analtech, Inc. Delaware, USA) Thin-layer chromatography (TLC) was carried out using pre-coated silica gel sheets (Merck 60 F254). Visual detection was performed with ultraviolet light, p-anisaldehyde stain, ninhydrin stain, dinitrophenyl hydrazine stain, potassium permanganate stain, or iodine. Reactions at lower temperature were performed by using cold baths: $H_2O$/ice at 0° C., acetone/dry ice at −78° C. $^1$H NMR spectra were recorded at 400 MHz with a Varian V400 spectrometer, Bruker 400 (unless otherwise noted) at ambient temperature, using tetramethylsilane as internal reference. The chemical shift values are quoted in δ (parts per million). Mass spectra of all the intermediates and final compounds were recorded using Waters Acquity UPLC-SQD & Agilent 1290 with 6150 SQD machines. High Performance Liquid Chromatography (HPLC) spectra were recorded using Agilent UHPLC 1290 and Waters, Alliance. LC-MS spectra were recorded using Agilent 1200 LC-MS/Agilent 1290 UHPLC-SQD with DAD detection LC-MS instruments using a BEH C18 column and ZORBAX HD C18 column (50 mm×2.1 mm×1.7µ) & (50 mm×2.1 mm×1.8µ), a mobile phase of 0.01% of acetic acid with acetonitrile and 0.01% of acetic acid with methanol, a flow rate of 0.3 mL/min, a temperature of 70 and 50° C., and a run time of 3.0 and sometimes 5 min. The purity of each of the final compounds was detected using WATERS PDA with SQD and AGILENT DAD with 6150 SQD instruments and the following conditions:

Condition 1: Column: Waters BEH C18; mobile phase: 0.01% acetic acid with acetonitrile & 0.01% acetic acid with Methanol; gradient: (B/% T):0/0, 1.2/100, 2.5/100, 2.8/0, 3.0/0; flow: 0.3 mL/min; temperature: 70° C.; run time: 3.0 min.

Condition 2: Column: ZORBAX HD C18; mobile phase: 0.01% acetic acid with acetonitrile & 0.01% acetic acid with Methanol; gradient: (B/% T):0/0, 2.5/100, 4.5/100, 4.8/0, 5.0/0; flow: 0.3 mL/min; temperature: 50° C.; run time: 5.0 min.

The following abbreviations are used herein and have the indicated definitions ACN is acetonitrile; BCA is bicinchoninic acid; bid po means twice daily by mouth; CDI is 1,1-carbonyl diimidazole; conc is concentrated; DMSO is dimethylsulfoxide; DCC is dicyclohexylcarbodiimide; DCM is dichloromethane; DIPEA is diisopropyl-ethylamine; DMF is N,N-dimethylformamide; dppf is 1,1'-bis(diphenylphosphino)-ferrocene; DTT is dithiothreitol; EDC.HCl is 1-(3-dimethylaminopropyl)-3-ethyl-carbodiimide hydrochloride; EDTA is ethylenediamine tetraacetic acid; EGTA is ethylene glycol tetraacetic acid; ELISA is enzyme-linked immunosorbent assay; EtOH is ethanol; ESI is electrospray ionization; EI is electron impact ionization; HATU is 2-(1H-7-azabenzotriazol-1-yl)-1,1,3,3-tetramethyl uronium hexafluorophosphate methanaminium; HEPES is (4-(2-hydroxyethyl)-1-piperazineethane-sulfonic acid; HPCD is hydroxypropyl-β-cyclodextrin; HPLC is high performance liquid chromatography; Hz is hertz; HOAt is 1-hydroxy-7-azabenzotriazole; HOBt is 1-hydroxy benzotriazole; KOAc is potassium acetate; LC is liquid chromatography; LDA is lithium diisopropylamine; MS is mass spectroscopy; MeOH is methanol; MHz is megahertz; mM is millimolar; mL is milliliter; min is minutes; mol is moles; $M^+$ is molecular ion; $[M+H]^+$ is protonated molecular ion; N is normality; NMR is nuclear magnetic resonance; PBS is phosphate buffered saline; PMSF is phenyl-methanesulfonyl fluoride; $PPh_3$ is triphenylphosphine; PTSA is para-toluenesulphonic acid; psi is pound per square inch; PPM is parts per million; qd po means daily by mouth; rt is room temperature; RT is retention time; tetrakis is tetrakis(triphenyl-phosphine)palladium(0); TLC is thin layer chromatography; TFA is trifluoroacetic acid; TEA is triethylamine; THF is tetrahydrofuran; TMS is

Example 1

5-(1-(1H-imidazol-1-yl)propyl)-2-(3-fluorophenyl)thiazole

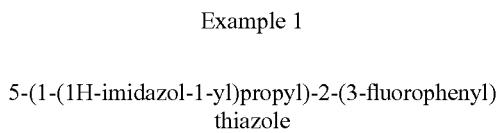

Step 1: 2-(3-fluorophenyl)thiazole-5-carbaldehyde

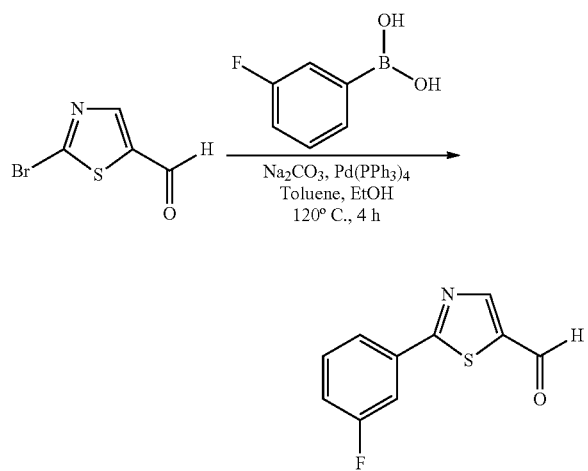

To a solution of 2-bromothiazole-5-carbaldehyde (0.6 g, 3.125 mmol) in toluene (2 mL) and ethanol (1 mL) was added 4-fluorophenyl boronic acid (0.524 g, 3.75 mmol), 2 M solution of aq. Na$_2$CO$_3$. The reaction mixture degassed with argon, tetrakis (0.180 g, 0.156 mmol) was added, the reaction mixture was again degassed with argon for 10 min, and heated to 120° C. for 4 h. The reaction mixture was evaporated under vacuum to remove ethanol, the reaction mixture was diluted with water (10 mL), extracted with ethyl acetate (50 mL) and dried over sodium sulphate, filtered and evaporated under reduced pressure to obtain crude product. The crude product was purified by Biotage Isolera® One chromatography (using 6% ethyl acetate and hexane) to give 2-(3-fluorophenyl)thiazole-5-carbaldehyde (0.350 g, 54% yield); $^1$H NMR (400 MHz, DMSO-d$_6$): δ 8.78 (s, 1H), 7.90 (dd, 2H), 7.61 (q, 1H); 7.44 (t, 1H); LC-MS m/z calcd for [M+H]$^+$ 208.02. found 208.0.

Step 2: 1-(2-(3-fluorophenyl)thiazol-5-yl)propan-1-ol

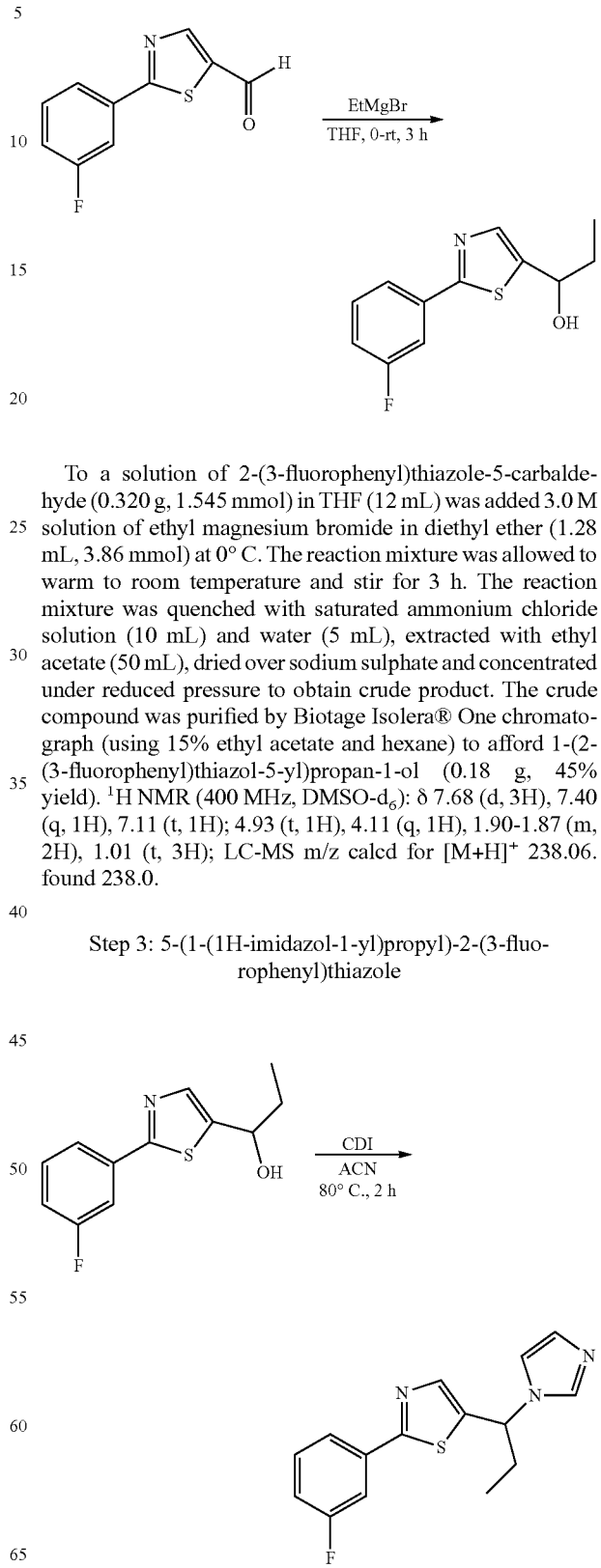

To a solution of 2-(3-fluorophenyl)thiazole-5-carbaldehyde (0.320 g, 1.545 mmol) in THF (12 mL) was added 3.0 M solution of ethyl magnesium bromide in diethyl ether (1.28 mL, 3.86 mmol) at 0° C. The reaction mixture was allowed to warm to room temperature and stir for 3 h. The reaction mixture was quenched with saturated ammonium chloride solution (10 mL) and water (5 mL), extracted with ethyl acetate (50 mL), dried over sodium sulphate and concentrated under reduced pressure to obtain crude product. The crude compound was purified by Biotage Isolera® One chromatograph (using 15% ethyl acetate and hexane) to afford 1-(2-(3-fluorophenyl)thiazol-5-yl)propan-1-ol (0.18 g, 45% yield). $^1$H NMR (400 MHz, DMSO-d$_6$): δ 7.68 (d, 3H), 7.40 (q, 1H), 7.11 (t, 1H); 4.93 (t, 1H), 4.11 (q, 1H), 1.90-1.87 (m, 2H), 1.01 (t, 3H); LC-MS m/z calcd for [M+H]$^+$ 238.06. found 238.0.

Step 3: 5-(1-(1H-imidazol-1-yl)propyl)-2-(3-fluorophenyl)thiazole

To a solution of 1-(2-(3-fluorophenyl)thiazol-5-yl)propan-1-ol (0.90 g, 0.379 mmol) in acetonitrile (2.5 mL) was added CDI (0.319 g, 1.97 mmol) at room temperature. The solution was heated to 80° C. for 2 hours, the reaction was diluted with ice cold water and extracted with ethyl acetate (50 mL), dried over sodium sulphate and filtered and concentrated under reduced pressure to obtain crude product. The crude product was purified by preparative TLC by using (5% MeOH/DCM) to give 5-(1-(1H-imidazol-1-yl)propyl)-2-(3-fluorophenyl)thiazole (0.014 g, 14% yield); $^1$H NMR (400 MHz, DMSO-$d_6$): δ 7.91 (s, 1H), 7.83 (s, 1H), 7.70 (t, 2H), 7.52 (q, 1H), 7.31 (t, 1H), 6.93 (s, 1H), 2.31-2.22 (m, 2H), 0.82 (t, 3H); LC-MS m/z calcd for [M+H]$^+$ 288.09. found 288.0.

Example 2

5-(1-(1H-imidazol-1-yl)propyl)-2-(1-methyl-1H-pyrazol-3-yl)thiazole

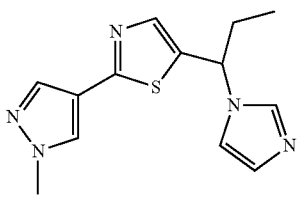 [SMILES: CCC(c1cnc(-c2cnn(C)c2)s1)n1ccnc1]

Step 1: 2-(1H-pyrazol-3-yl)thiazole-5-carbaldehyde

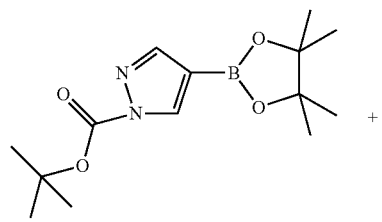

To a solution of 2-bromothiazole-5-carbaldehyde (0.8 g, 4.16 mmol) in toluene (6 mL) and EtOH (5 mL), tert-butyl 3-(4,4,5,5-tetramethyl-1,3,2-dioxaborolan-2-yl)-1H-pyrazole-1-carboxylate (1.8 g, 6.2 mmol), 2M Na$_2$CO$_3$ (6.2 mL, 12.4 mmol) and Pd(PPh$_3$)$_4$ (0.45 mg, 0.4 mmol) were added under argon. The mixture was degassed, heated to 100° C., stirred for 1 h. After completion of the reaction, by monitoring with TLC (5% MeOH\DCM), the resulting mixture was filtered with Celite® reagent and the filtrate was separated. This filtrate was concentrated, extracted with EtOAc (2×100 mL), washed with water (100 mL), dried over Na$_2$SO$_4$ and concentrated in vacuo. The resulting residue was purified by Biotage Isolera® One column purifier (silica gel 100-200 microns) using 3% methanol in dichloromethane and isolated as yellow color solid (0.25 g, 33% yield). $^1$H NMR (400 MHz, DMSO-$d_6$): δ 13.49 (brs, 1H), 10.03 (s, 1H), 8.60 (s, 1H), 8.55 (s, 1H), 8.09 (s, 1H); LC-MS m/z calcd for [M+H]$^+$, 180.02. found, 180.1.

Step 2: 2-(1-methyl-1H-pyrazol-3-yl)thiazole-5-carbaldehyde

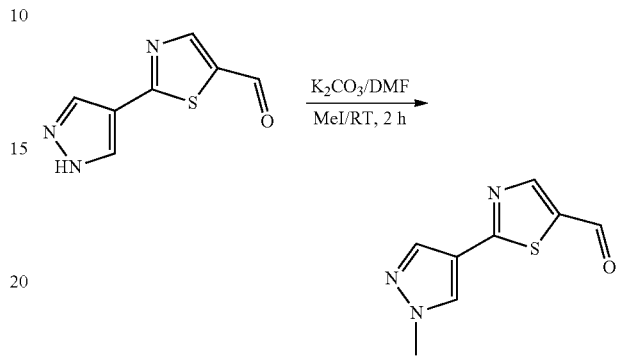

2-(1H-pyrazol-3-yl)thiazole-5-carbaldehyde (0.25 g, 1.3 mmol) was dissolved in DMF (5 mL) and iodomethane (0.26 mL, 4.1 mmol) and potassium carbonate (0.6 g, 4.1 mmol) were added. The reaction was stirred for 3 h at room temperature until the reaction was deemed complete by TLC (80% EtOAc\hexane). The reaction was poured into ice water (50 mL), and the aqueous layer was extracted with ethyl acetate (2×50 mL). The organic layers were combined, washed with brine, dried over sodium sulfate, and concentrated under vacuum to afford 2-(1-methyl-1H-pyrazol-3-yl)thiazole-5-carbaldehyde as a yellow solid (0.1 g, 38% yield). $^1$H-NMR (DMSO-$d_6$): δ 10.0 (s, 1H) 8.60 (s, 1H). 8.50 (s, 1H), 8.05 (s, 1H), 3.89 (s, 3H); LC-MS m/z calcd for [M+H]$^+$, 194.03. found, 194.1.

Step 3: 1-(2-(1-methyl-1H-pyrazol-3-yl)thiazol-5-yl)propan-1-ol

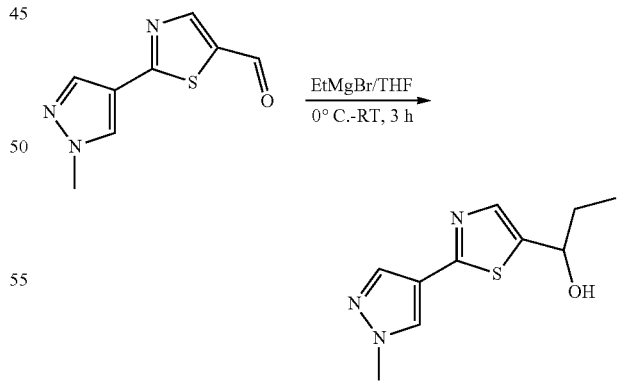

To a solution of 2-(1-methyl-1H-pyrazol-3-yl)thiazole-5-carbaldehyde (0.1 g, 0.51 mmol) in THF (10 mL) at 0° C. was slowly added 3.0 M ethyl magnesium bromide in diethyl ether (0.5 mL, 0.15 mmol), and the reaction mixture was stirred at 0° C. for 3 h. After completion of reaction by monitoring with TLC (5% MeOH\DCM), the reaction mixture was quenched with sat'd. NH$_4$Cl (50 mL) solution. The reaction mixture was then extracted with EtOAc (3×50 mL), washed with water (2×50 mL), dried over Na₂SO₄ and concentration in vacuo and to provide a yellow solid (0.09 g, 81% yield). ¹H NMR (400 MHz, DMSO-d₆): δ 8.21 (s, 1H), 7.82 (s, 1H), 7.50 (s, 1H), 5.60 (d, 1H), 4.70 (q, 1H), 3.86 (s, 3H), 1.69 (m, 2H), 0.844 (t, 3H).

Step 4: 5-(1-(1H-imidazol-1-yl)propyl)-2-(1-methyl-1H-pyrazol-3-yl)thiazole

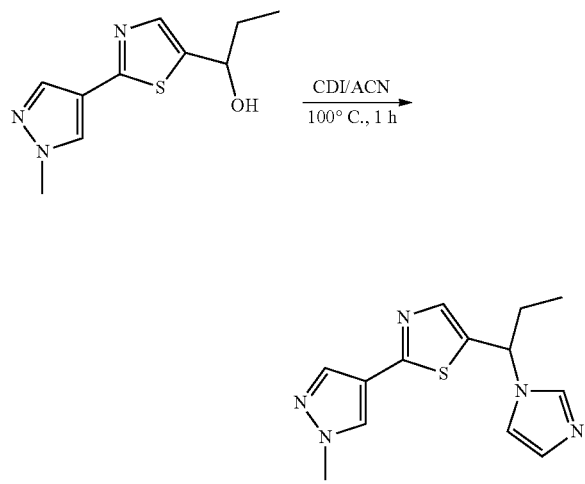 [SMILES: CCC(O)c1cnc(-c2cnn(C)c2)s1 ; CCC(c1cnc(-c2cnn(C)c2)s1)n1ccnc1]

To a solution of 1-(2-(1-methyl-1H-pyrazol-3-yl)thiazol-5-yl)propan-1-ol (0.09 g, 0.4 mmol) in acetonitrile (10.0 mL) was added CDI (0.34 g, 2.1 mmol) and the reaction was heated to 100° C. and stirred for 1 h. Completion of the reaction was monitored with TLC (10% MeOH\DCM). Then reaction mixture was concentrated in vacuo, diluted with ethyl acetate (2×100 mL), washed with water (100 mL), dried over Na₂SO₄ and concentrated in vacuo. The resulting residue was purified by preparative TLC using 5% methanol in dichloromethane. A light yellow color viscous liquid (0.015 g, 13% yield) was obtained. ¹H NMR (400 MHz, DMSO-d₆): δ 8.25 (s, 1H), 7.82 (d, 2H), 7.70 (s, 1H), 7.28 (s, 1H), 6.93 (s, 1H), 5.63 (t, 1H), 3.86 (s, 3H), 2.22 (m, 2H), 0.82 (t, 3H); LC-MS m/z calcd for [M+1]⁺, 274.10. found, 274.1.

Example 3

1-(1-(5-(4-methoxyphenyl)thiophen-2-yl)propyl)-1H-imidazole

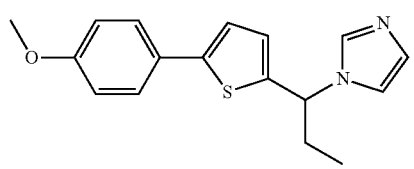 [SMILES: CCC(c1ccc(-c2ccc(OC)cc2)s1)n1ccnc1]

Step 1: 5-(4-methoxyphenyl)thiophene-2-carbaldehyde

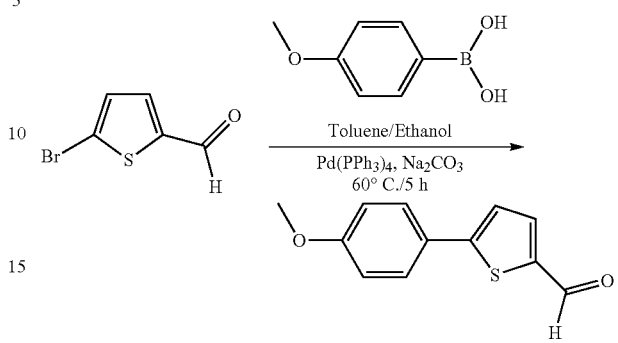

To a stirred solution of 5-bromothiophene-2-carbaldehyde (1 g, 5.2 mmol) in toluene (40 mL) and ethanol (20 mL) was added (4-methoxyphenyl)boronic acid (1.59 g, 10.4 mmol), 2M Na₂CO₃ (14.7 mL), and Pd(PPh₃)₄ (60 mg, 0.05 mmol). The reaction was purged with argon and heated at 60° C. for about 5 h. The reaction mixture was concentrated, diluted with water (100 mL), and extracted with ethyl acetate (2×200 mL). The combined organic extracts were washed with brine solution (20 mL), the organic layer was dried over Na₂SO₄ and concentrated under vacuum to obtain crude product. The crude product was purified by flash chromatography (silica gel, 60-120μ) using 10% ethyl acetate in hexane eluent to afford 5-(4-methoxyphenyl)thiophene-2-carbaldehyde as off white solid (1 g, 87.7% yield). ¹H NMR (400 MHz, DMSO-d₆): δ 9.85 (s, 1H), 7.97 (d, 1H), 7.73 (d, 2H), 7.61 (d, 1H), 7.02 (d, 2H), 3.98 (s, 3H); LC-MS m/z calcd for [M+H]⁺ 219.04. found 219.3.

Step 2: 1-(5-(4-methoxyphenyl)thiophen-2-yl)propan-1-ol

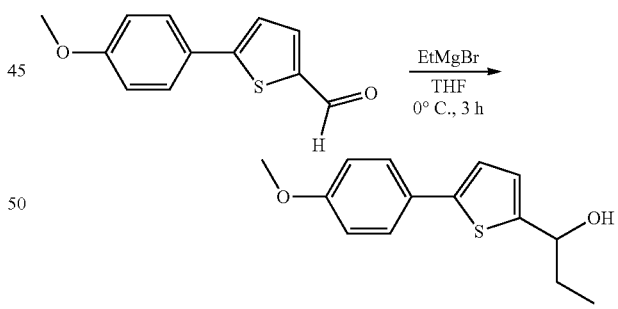

5-(4-methoxyphenyl)thiophene-2-carbaldehyde (300 mg, 1.3 mmol) in THF (6 mL) was cooled to 0° C. 3-M ethyl magnesium bromide in diethyl ether (0.8 mL, 2.7 mmol) was then slowly added at 0° C. and the reaction mixture was stirred for 3 h at 0° C., (reaction progress was monitored by TLC). The reaction mixture was quenched with saturated NH₄Cl solution (10 mL) and extracted with ethyl acetate (2×200 mL).

The combined organic extracts were washed with brine solution (10 mL), the organic layer was dried over Na₂SO₄ and the solution was concentrated under vacuum to obtain crude product. The crude product was purified by flash chromatography (silica gel, 60-120μ) using 10% ethyl acetate in hexane eluent afforded 1-(5-(4-methoxyphenyl)thiophen-2-yl)propan-1-ol as pale yellow liquid (150 mg, 43.9% yield). $^1$H NMR (400 MHz, DMSO-d$_6$): δ 7.51 (d, 2H), 7.15 (d, 1H), 6.94 (d, 2H), 6.84 (d, 1H), 5.45 (d, 1H), 4.64-4.60 (m, 1H), 3.79 (s, 3H), 1.72-1.65 (m, 2H), 0.88 (s, 3H); LC-MS m/z calcd for [M+H]$^+$ 249.09. found 249.4.

Step 3: 1-(1-(5-(4-methoxyphenyl)thiophen-2-yl) propyl)-1H-imidazole

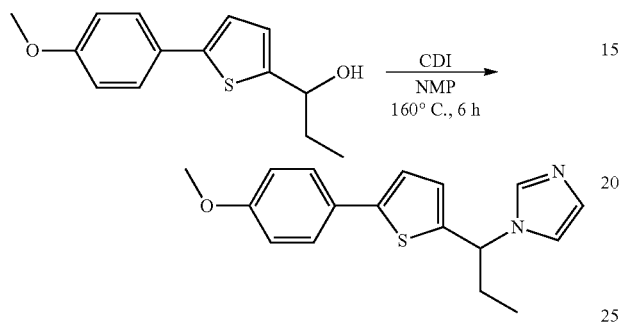

To a stirred solution of 1-(5-(4-methoxyphenyl)thiophen-2-yl)propan-1-ol (95 mg, 0.3 mmol) in NMP (4 mL) was added 1,1-carbonyl diimidazole (495 mg, 3 mmol). The reaction was refluxed at 160° C. for about 6 h. The reaction mixture was concentrated, diluted with water (100 mL) and extracted with ethyl acetate (2×100 mL). The combined organic extracts were washed with brine solution (10 mL), the organic layer was dried over Na$_2$SO$_4$ and then concentrated under vacuum to obtain crude product. The crude product was purified by flash chromatography (silica gel, 60-120 microns) using 2% methanol in DCM as an eluent to afford 1-(1-(5-(4-methoxyphenyl)thiophen-2-yl)propyl)-1H-imidazole as an off white solid (30 mg, 26.3% yield). $^1$H NMR (400 MHz, DMSO-d$_6$): δ 7.78 (s, 1H), 7.49 (d, 2H), 7.26 (s, 1H), 7.22 (d, 1H), 7.03 (d, 1H), 6.92 (t, 3H), 5.49 (t, 1H), 3.75 (s, 3H), 2.24-2.17 (m, 2H), 0.81 (t, 3H), LC-MS m/z calcd for [M+H]$^+$ 299.11. found 231.3 [M-imidazole]$^+$.

Example 4

4-(5-(1-(1H-imidazol-1-yl)propyl)thiophen-2-yl) phenol

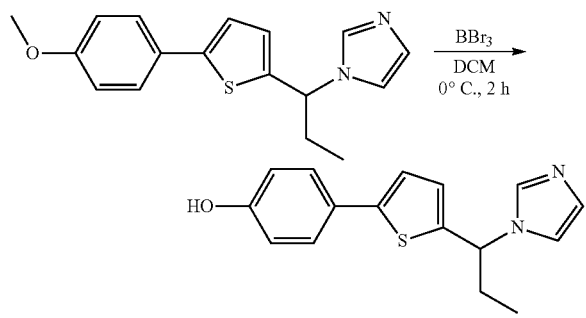

To a stirred solution of 1-(1-(5-(4-methoxyphenyl) thiophen-2-yl)propyl)-1H-imidazole (45 mg, 0.15 mmol; prepared as described in Example 3) in DCM (4 mL) was added BBr$_3$ (0.02 mL, 0.22 mmol) at 0° C. The reaction was stirred at 0° C. for about 2 h, quenched with saturated NaHCO$_3$ solution (10 mL), and extracted with DCM (2×100 mL). The combined organic extracts were washed with brine solution (10 mL), the organic layer was dried over Na$_2$SO$_4$ and concentrated under vacuum to obtain crude product. The crude product was washed with pentane (10 mL) afforded 4-(5-(1-(1H-imidazol-1-yl)propyl)thiophen-2-yl)phenol as off white solid (42 mg, 81.3% yield). $^1$H NMR (400 MHz, DMSO-d$_6$): δ 9.59 (s, 1H), 7.78 (s, 1H), 7.37 (d, 2H), 7.25 (s, 1H), 7.14 (d, 1H), 7.01 (d, 1H), 6.90 (s, 1H), 6.75 (d, 2H), 5.47 (t, 1H), 2.31-2.16 (m, 2H), 0.80 (t, 3H), LC-MS m/z calcd for [M–H]$^+$ 285.10. found 217.2 [M-imidazole]$^+$.

Example 5

Ethyl 4-(6-(1-(1H-imidazol-1-yl)propyl)pyridin-3-yl) benzoate

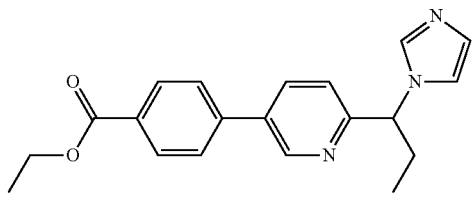 [SMILES: CCOC(=O)c1ccc(-c2ccc(C(CC)n3ccnc3)nc2)cc1]

Step 1: ethyl 4-(6-formylpyridin-3-yl)benzoate

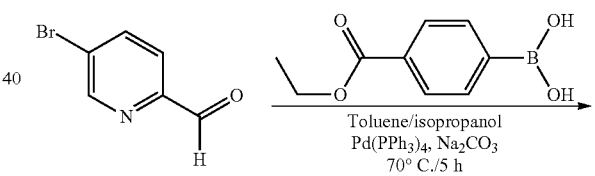

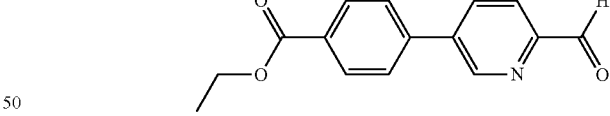

To a stirred solution of 5-bromopicolinaldehyde (2 g, 10.7 mmol) in toluene (80 mL) and isopropanol (40 mL) was added 4-(ethoxycarbonyl)phenyl)boronic acid (4.17 g, 21.5 mmol), 2M Na$_2$CO$_3$ (30 mL) and Pd(PPh$_3$)$_4$ (124 mg, 0.1 mmol). The reaction was purged with argon and heated at 70° C. for about 5 h. The reaction mixture was concentrated and diluted with water (200 mL), extracted with ethyl acetate (2×500 mL). The combined organic extracts were washed with brine solution (50 mL), the organic layer was dried over Na$_2$SO$_4$ and concentrated under vacuum to obtain crude product. The crude product was purified by flash chromatography (silica gel, 60-120μ) using 10% ethyl acetate in hexane eluent to afford ethyl 4-(6-formylpyridin-3-yl)benzoate as an off white solid (1.7 g, 62% yield). $^1$H NMR (400 MHz, DMSO-d$_6$): δ 10.03 (s, 1H), 9.20 (d, 1H), 8.39 (dd, 1H), 8.08

(d, 2H), 8.02 (d, 1H), 7.99 (d, 2H), 4.36-4.31 (m, 2H), 1.33 (t, 3H), LC-MS m/z calcd for [M+H]⁺ 256.09. found 256.2.

Step 2: ethyl 4-(6-(1-hydroxypropyl)pyridin-3-yl)benzoate

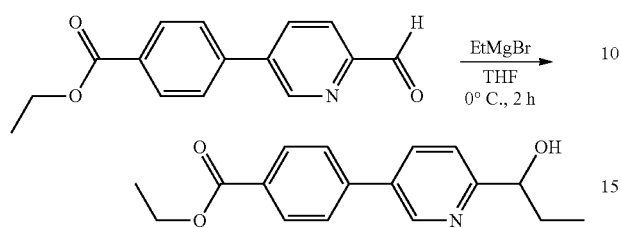

Ethyl 4-(6-formylpyridin-3-yl)benzoate (500 mg, 1.9 mmol) in THF (15 mL) was cooled to 0° C., 3M Ethyl magnesium bromide in diethyl ether (1.3 mL, 3.9 mmol) was slowly added at 0° C., and the reaction mixture was stirred for 2 h at 0° C., while monitoring reaction progress by TLC. The reaction mixture was quenched with saturated NH₄Cl solution (20 mL) and extracted with ethyl acetate (2×200 mL). The combined organic extracts were washed with brine solution (10 mL), the organic layer was dried over Na₂SO₄ and concentrated under vacuum to obtain crude product. The crude product was purified by flash chromatography (silica gel, 60-120 microns) using 15% ethyl acetate in hexane eluent to afford ethyl 4-(6-(1-hydroxypropyl)pyridin-3-yl)benzoate as a brown liquid (250 mg, 44.8% yield). ¹H NMR (400 MHz, DMSO-d₆): δ 8.84 (s, 1H), 8.13-8.11 (d, 1H), 8.04 (d, 2H), 7.87 (d, 2H), 7.57 (d, 1H), 5.33 (d, 1H), 4.57-4.53 (m, 1H), 4.35-4.30 (m, 2H), 1.89-1.76 (m, 1H), 1.68-1.34 (m, 1H), 1.24 (t, 3H), 0.86 (t, 3H), LC-MS m/z calcd for [M+H]⁺ 286.14. found 286.2.

Step 3: ethyl 4-(6-(1-(1H-imidazol-1-yl)propyl)pyridin-3-yl)benzoate

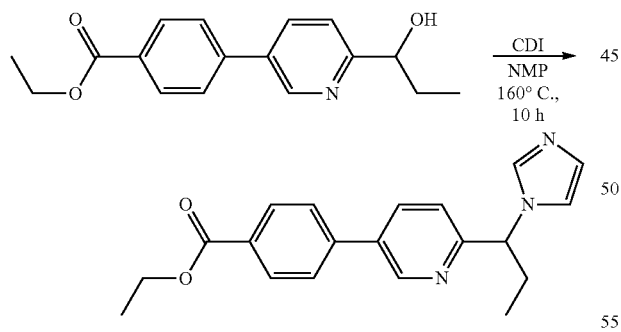

To a stirred solution of ethyl 4-(6-(1-hydroxypropyl)pyridin-3-yl)benzoate (300 mg, 1 mmol) in NMP (3 mL) was added 1,1-carbonyl diimidazole (1.36 g, 8.4 mmol) and the reaction was refluxed at 160° C. for about 10 h. The reaction mixture was concentrated, diluted with water (200 mL), and extracted with ethyl acetate (2×200 mL). The combined organic extracts were washed with brine solution (10 mL), the organic layer was dried over Na₂SO₄ and concentrated under vacuum to obtain crude product. The crude product was purified by prep TLC method using 5% methanol in DCM afforded ethyl 4-(6-(1-(1H-imidazol-1-yl)propyl)pyridin-3-yl)benzoate as brown liquid (65 mg, 22.7% yield). ¹H NMR (400 MHz, DMSO-d₆): δ 8.93 (d, 1H), 8.13 (dd, 1H), 8.03 (d, 2H), 7.87 (d, 2H), 7.81 (s, 1H), 7.41 (d, 1H), 7.31 (s, 1H), 6.90 (s, 1H), 5.41-5.37 (m, 1H), 4.35-4.29 (m, 2H), 2.34-2.19 (m, 2H), 1.32 (t, 3H), 0.81 (t, 3H), LC-MS m/z calcd for [M+H]⁺ 336.16. found 336.2.

Example 6

4-(6-(1-(1H-imidazol-1-yl)propyl)pyridin-3-yl)benzoic acid

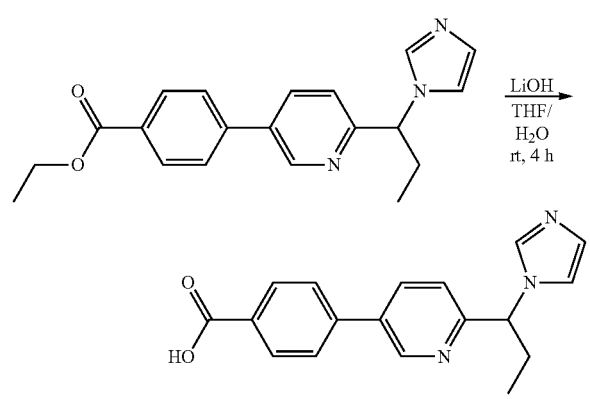

To a stirred solution of ethyl 4-(6-(1-(1H-imidazol-1-yl)propyl)pyridin-3-yl)benzoate (25 mg, 0.07 mmol; prepared as described in Example 5) in THF (2 mL) and water (1 mL) was added LiOH (6 mg, 0.14 mmol) at rt and the reaction was stirred at rt for about 4 h. The reaction mixture was neutralized with 1N HCl (pH=6) and extracted with ethyl acetate (2×100 mL). The combined organic extracts were washed with brine solution (10 mL), the organic layer was dried over Na₂SO₄ and concentrated under vacuum to obtain crude product. The crude product was purified by prep TLC using 5% methanol in DCM to provide 4-(6-(1-(1H-imidazol-1-yl)propyl)pyridin-3-yl)benzoic acid as an off white solid (12 mg, 54.5% yield). ¹H NMR (400 MHz, DMSO-d₆): δ 8.92 (s, 1H), 8.14 (dd, 1H), 8.01 (d, 2H), 7.83 (d, 3H), 7.40 (d, 1H), 7.31 (s, 1H), 6.90 (s, 1H), 5.39 (s, 1H), 2.34-2.19 (m, 2H), 0.81 (t, 3H), LC-MS m/z calcd for [M+H]⁺ 308.13. found 308.1.

Example 7

2-(1-(1H-imidazol-1-yl)propyl)-5-(3-methoxyphenyl)pyridine

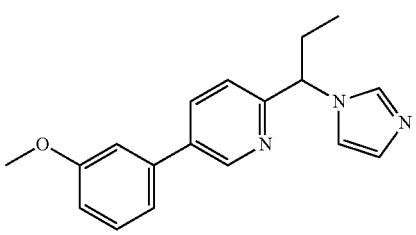 [SMILES: CCC(c1ccc(-c2cccc(OC)c2)cn1)n1ccnc1]

Step 1: 5-(3-methoxyphenyl)picolinaldehyde

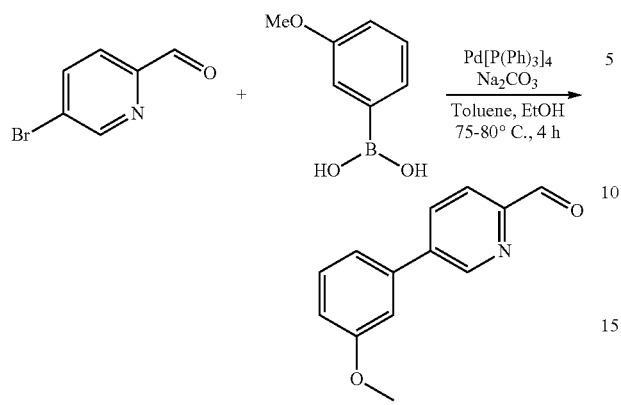

To a solution of 5-bromopicolinaldehyde (1.0 g, 5.43 mmol) in toluene (10 mL) and ethanol (8 mL) was added (3-methoxyphenyl)boronic acid (1.2 g, 8.1 mmol), 2M sodium carbonate (3.4 g, 32.6 mmol, 8 mL water), Pd(PPh$_3$)$_4$ (0.228 g, 0.25 mmol) under argon. The resulting mixture was heated at 75-80° C., for 4 h. The contents were cooled to room temperature, diluted with ethyl acetate (150 mL) and washed with bicarbonate solution (2×100 mL) and brine solution (2×100 mL). The organic layer was dried over sodium sulphate, which was distilled off to obtain the crude product. The crude product was purified by flash chromatography (100-200 microns; 15% ethyl acetate in hexane) to afford 5-(3-methoxyphenyl)picolinaldehyde (0.75 g, 65% yield). $^1$H NMR (400 MHz, DMSO-d$_6$): δ 10.02 (s, 1H), 9.14 (s, 1H), 8.33 (d, 1H), 7.98 (d, 1H), 7.45 (t, 1H), 7.38 (d, 2H), 7.03 (d, 1H), 3.84 (s, 3H); LC-MS m/z calculated for [M+H]$^+$ 214.08 found, 214.3.

Step 2: 1-(5-(3-methoxyphenyl)pyridin-2-yl)propan-1-ol

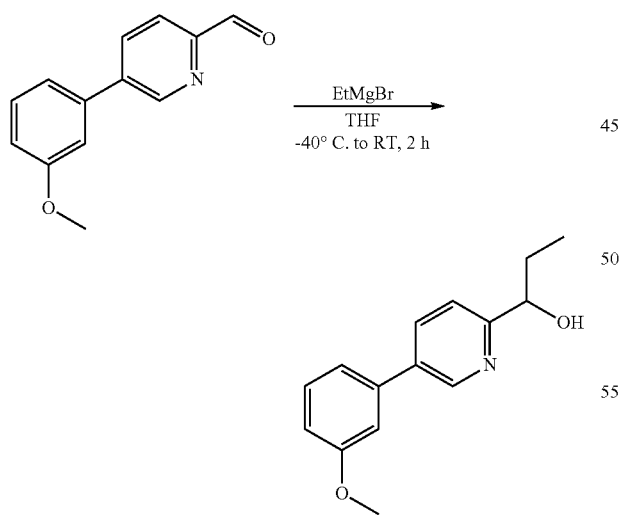

To a solution of 5-(3-methoxyphenyl)picolinaldehyde (0.75 g, 3.5 mmol), in THF (7 mL) was added methyl magnesium bromide (0.17 g, 8.8 mmol) under nitrogen at −40° C./ The reaction was brought to rt and then stirred at rt for 2 h. The contents were diluted with ethyl acetate (150 mL), quenched with ammonium chloride solution (100 mL), the organic layer washed with brine solution (2×100 mL), the layers separated, the organic layer was dried over sodium sulphate and distilled off to get the crude product. The compound was purified by flash chromatography (100-200 microns; 15% ethyl acetate in hexane) to give 1-(5-(3-methoxyphenyl)pyridin-2-yl)propan-1-ol (450 mg, 53% yield). $^1$H NMR (400 MHz, DMSO-d$_6$): δ 8.73 (s, 1H), 8.04 (d, 1H), 7.52 (d, 1H), 7.38 (t, 1H), 7.26 (s, 1H), 7.23 (d, 1H), 6.95 (d, 1H), 5.28 (d, 1H), 4.54 (q, 1H), 3.81 (s, 3H), 1.7 (m, 1H), 1.8 (m, 1H), 0.86 (t, 3H); LC-MS m/z calcd for [M+H]$^+$ 244.13. found 244.0.

Step 3: 2-(1-bromopropyl)-5-(3-methoxyphenyl)pyridine

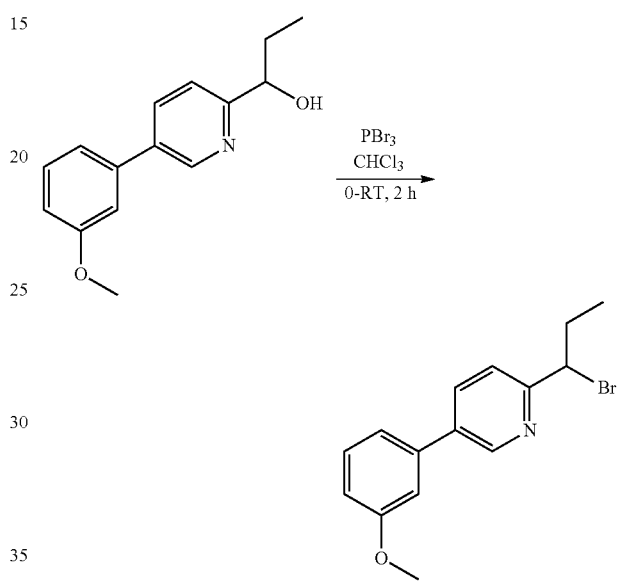

To a solution of 1-(5-(3-methoxyphenyl)pyridin-2-yl)propan-1-ol (0.45 g, 1.8 mmol) in chloroform (5 mL) was added PBr$_3$ (1.5 g, 5.55 mmol) at 0-5° C., the reaction was maintained at the same temperature for 1 h, and then the reaction was slowly warmed to rt and maintained at this temperature for 1 h. The contents were diluted with water (75 mL) and chloroform (100 mL) and the layers were separated. The organic layer was washed with bicarbonate solution (2×30 mL), dried over sodium sulphate and distilled to get the crude product. The non-polar impurity was removed by pentane washings (2×7 mL) to provide 2-(1-bromopropyl)-5-(3-methoxyphenyl)pyridine (0.45 g, crude). LC-MS m/z calcd for [M+H]$^+$ 306.04. found 306.0.

Step 4: 2-(1-(1H-imidazol-1-yl)propyl)-5-(3-methoxyphenyl)pyridine

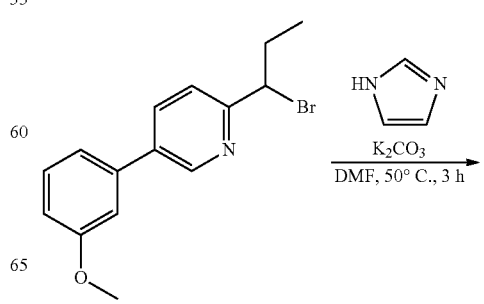

-continued

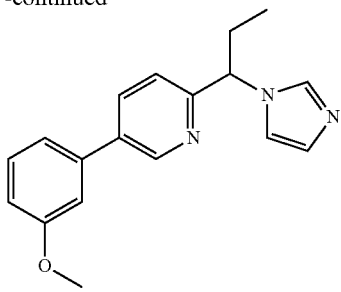

To a solution of imidazole (0.2 g, 2.9 mmol) in DMF (5 mL) was added potassium carbonate (0.4 g, 2.9 mmol) and 2-(1-bromopropyl)-5-(3-methoxyphenyl)pyridine under nitrogen and the reaction was heated to 50° C. for 3 h. The contents were cooled to rt, diluted with water (100 mL) and extracted with ethyl acetate (2×100 mL). The layers were separated, the organic layer was washed with brine solution (2×30 mL), dried over sodium sulphate and distilled off to get the crude product. The product was purified by preparative TLC (2000μ; pure ethyl acetate) to provide 2-(1-(1H-imidazol-1-yl)propyl)-5-(3-methoxyphenyl)pyridine (50 mg, 12% yield). $^1$H NMR (400 MHz, DMSO-d$_6$): δ 8.86 (s, 1H), 8.09 (d, 1H), 7.81 (s, 1H), 7.40 (m, 2H), 7.36 (s, 1H), 7.25 (d, 2H), 6.97 (d, 1H), 6.89 (s, 1H), 5.37 (q, 1H), 3.80 (s, 3H), 2.25 (m, 2H), 0.82 (t, 3H); LC-MS m/z calcd for [M+H]$^+$ 294.15. found 294.2.

Example 8

3-(6-(1-(1H-imidazol-1-yl)propyl)pyridin-3-yl)phenol

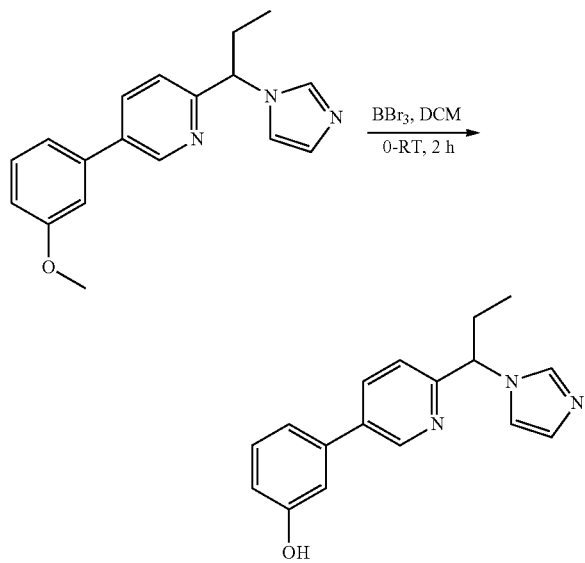

To a solution of 2-(1-(1H-imidazol-1-yl)propyl)-5-(3-methoxyphenyl) pyridine (0.05 g, 0.17 mmol; prepared as described in Example 7) in dichloromethane (1 mL) was added BBr$_3$ (0.064 g, 0.25 mmol) under nitrogen at 0° C. The reaction was stirred at this temperature for 1 h, allowed to warm to rt and then maintained at rt for another 1 h. The contents were diluted with dichloromethane (100 mL) and then distilled off to obtain crude product. Ice-cold water (100 mL) and dichloromethane (50 mL) were then added to the crude product, the mixture was shaken, and the DCM layer was discarded since the product was in the aqueous layer. To this aqueous layer was added ethyl acetate (100 mL) and saturated sodium bicarbonate solution (150 mL). The organic phase was washed with brine solution (2×50 mL), the layers were separated, and the organic layer was dried over sodium sulphate and distilled off to get the crude product. The product was recrystallized with dichloromethane and hexane to give 3-(6-(1-(1H-imidazol-1-yl)propyl)pyridin-3-yl)phenol (20 mg, 42% yield). $^1$H NMR (400 MHz, DMSO-d$_6$): δ 9.59 (s, 1H), 8.78 (d, 1H), 7.99 (d, 1H), 7.92 (s, 1H), 7.36 (d, 2H), 7.26 (t, 1H), 7.09 (d, 1H), 7.08 (s, 1H), 6.95 (s, 1H), 6.81 (d, 1H), 5.38 (q, 1H), 2.33 (m, 2H), 0.81 (t, 3H); LC-MS m/z calcd for [M+H]$^+$ 280.14. found 280.0.

Example 9

4-(6-(1-(1H-imidazol-1-yl)propyl)pyridin-3-yl)-N-methylbenzamide

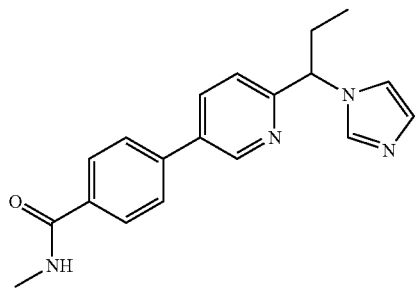 [SMILES: CCC(c1ccc(-c2ccc(C(=O)NC)cc2)cn1)n1ccnc1]

Step 1:
4-(6-formylpyridin-3-yl)-N-methylbenzamide

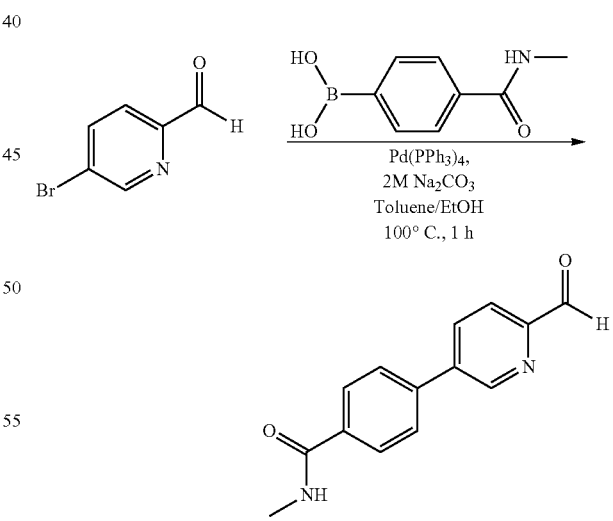

To a solution of 5-bromopicolinaldehyde (0.25 g, 1.34 mmol) in toluene (6 mL) and EtOH (5 mL) was added (4-(methylcarbamoyl)phenyl)boronic acid (0.36 g, 2.0 mmol), 2M Na$_2$CO$_3$ (2.5 mL, 4.03 mmol) and Pd(PPh$_3$)$_4$ (0.24 g, 0.2 mmol) under argon. The mixture was degassed, heated to 100° C., and stirred for 1 h. After completion of the reaction by monitoring with TLC (80% EtOAc\hexane), the resulting mixture was filtered using Celite® reagent. The filtrate was separated, concentrated, extracted with EtOAc (2×100 mL), washed with water (100 mL), dried over Na$_2$SO$_4$ and concentrated in vacuo. The resulting residue was purified by column chromatography (silica gel 100-200µ) using 60% ethyl acetate in hexane and isolated as a yellow solid (0.22 g, 62% yield). $^1$H NMR (400 MHz, DMSO-d$_6$): δ 10.0 (s, 1H), 9.20 (s, 1H), 8.53 (s, 2H), 8.39 (d, 2H), 7.9 (m, 3H); LC-MS: m/z 241.4 [M+H]$^+$.

Step 2: 4-(6-(1-hydroxypropyl)pyridin-3-yl)-N-methylbenzamide

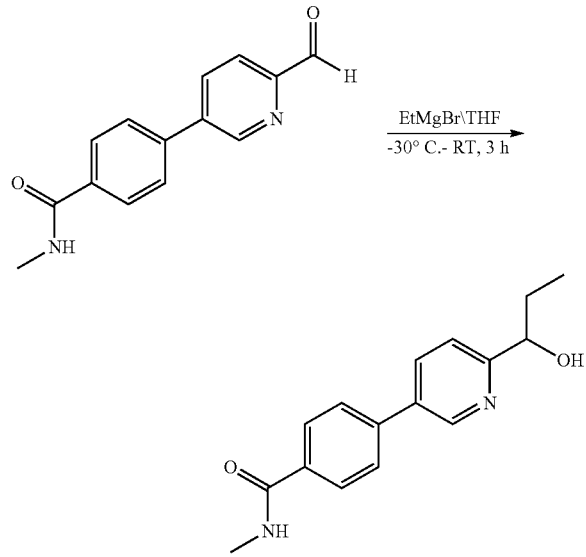

To a solution of 4-(6-formylpyridin-3-yl)-N-methylbenzamide (0.2 g, 0.8 mmol) in THF (15 mL) at –30° C. was slowly added 3.0 M ethyl magnesium bromide in diethyl ether (0.9 mL, 2.4 mmol) and the reaction mixture was stirred at rt for 3 h. After completion of the reaction as monitored with TLC (5% MeOH\DCM), the reaction mixture was quenched with sat'd. NH$_4$Cl (50 mL) solution. The reaction mixture was extracted with EtOAc (3×50 mL), washed with water (2×50 mL), dried over Na$_2$SO$_4$ and concentrated in vacuo. The resulting residue was purified by column chromatography (silica gel 230-400µ) using 2% methanol in dichloromethane. The product was isolated as a yellow solid (0.1 g, 45% yield). $^1$H NMR (400 MHz, DMSO-d$_6$): δ 8.82 (d, 1H), 8.46 (d, 1H), 8.11 (dd, 1H), 7.92 (d, 2H), 7.80 (d, 2H), 7.51 (d, 1H), 5.30 (d, 1H), 4.54 (q, 1H), 2.78 (d, 3H), 1.79 (m, 1H), 1.63 (m, 1H), 0.85 (t, 3H).

Step 3: 1-(5-(4-(methylcarbamoyl)phenyl)pyridin-2-yl)propyl methanesulfonate

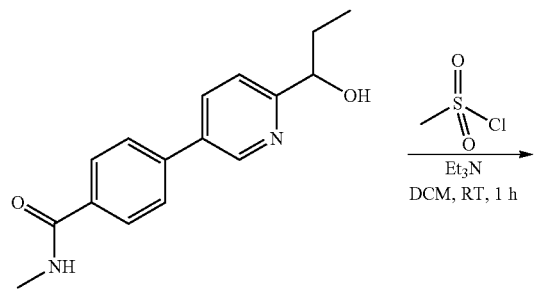

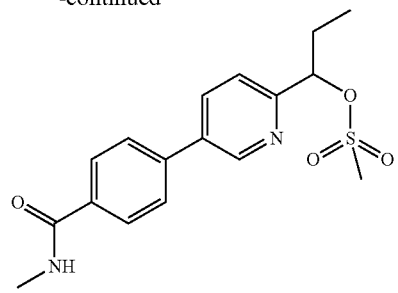

4-(6-(1-Hydroxypropyl)pyridin-3-yl)-N-methylbenzamide (0.02 g 0.074 mmol) and triethylamine (0.01 mL, 0.14 mmol) were dissolved in DCM (5 mL) and cooled to 0° C. To this solution was drop-wise added a solution of methanesulfonyl chloride (0.02 mL, 0.14 mmol) over 1 h and the mixture stirred at room temperature until the reaction was deemed complete by TLC (5% MeOH\DCM). The reaction was poured into water (50 mL), and the aqueous layer was extracted with dichloromethane (2×50 mL). The combined organic extract was washed with brine, dried over Na$_2$SO$_4$ and concentrated in vacuo to give the mesylate product as a yellow viscous liquid (0.02 g, 80% yield). $^1$H NMR (400 MHz, DMSO-d$_6$): δ 8.94 (d, 1H), 8.48 (d, 1H), 8.19 (dd, 1H), 7.94 (d, 2H), 7.84 (d, 2H), 7.59 (d, 1H), 5.59 (t, 1H), 3.14 (s, 3H), 2.79 (d, 3H), 2.05 (d, 3H), 0.89 (t, 3H). LC-MS: m/z 349.5 [M+H]$^+$.

Step 4: 4-(6-(1-(1H-imidazol-1-yl)propyl)pyridin-3-yl)-N-methylbenzamide

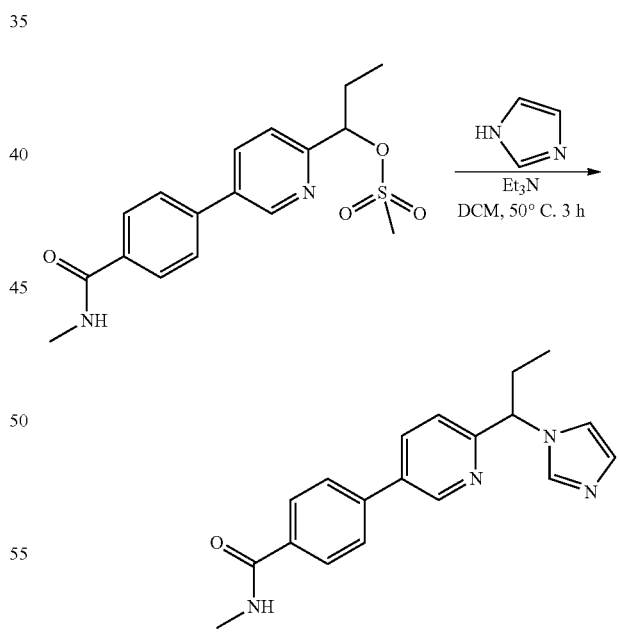

A mixture of 1-(5-(4-(methylcarbamoyl)phenyl)pyridin-2-yl)propyl methanesulfonate (0.02 g, 0.057 mmol), 1H-imidazole (0.008 g, 0.114 mmol) and triethylamine (0.03 mL, 0.114 mmol) in DCM (10 mL) was stirred and refluxed at 50° C. for 3 h. The mixture was then cooled to room temperature, poured out into ice water (50 mL) and extracted with DCM (2×50 mL). The organic layer was separated, dried (Na$_2$SO$_4$), and the solvent was evaporated under vacuo. The resulting residue was purified by preparative TLC using 5% methanol in dichloromethane and the product isolated as off white solid (0.007 g, 39% yield). $^1$H NMR (400 MHz, DMSO-d$_6$): δ 8.91 (d, 1H), 8.46 (d, 1H), 8.12 (d, 1H), 7.91 (d, 2H), 7.80 (d, 3H), 7.39 (d, 1H), 7.31 (s, 1H), 6.89 (s, 1H), 5.37 (t, 1H), 2.78 (d, 3H), 2.27 (m, 2H), 0.89 (t, 3H). LC-MS: m/z 321.5 [M+H]$^+$.

Example 10

4-(6-(1-(1H-imidazol-1-yl)propyl)pyridin-3-yl)benzamide

Step 1: 4-(6-formylpyridin-3-yl)benzamide

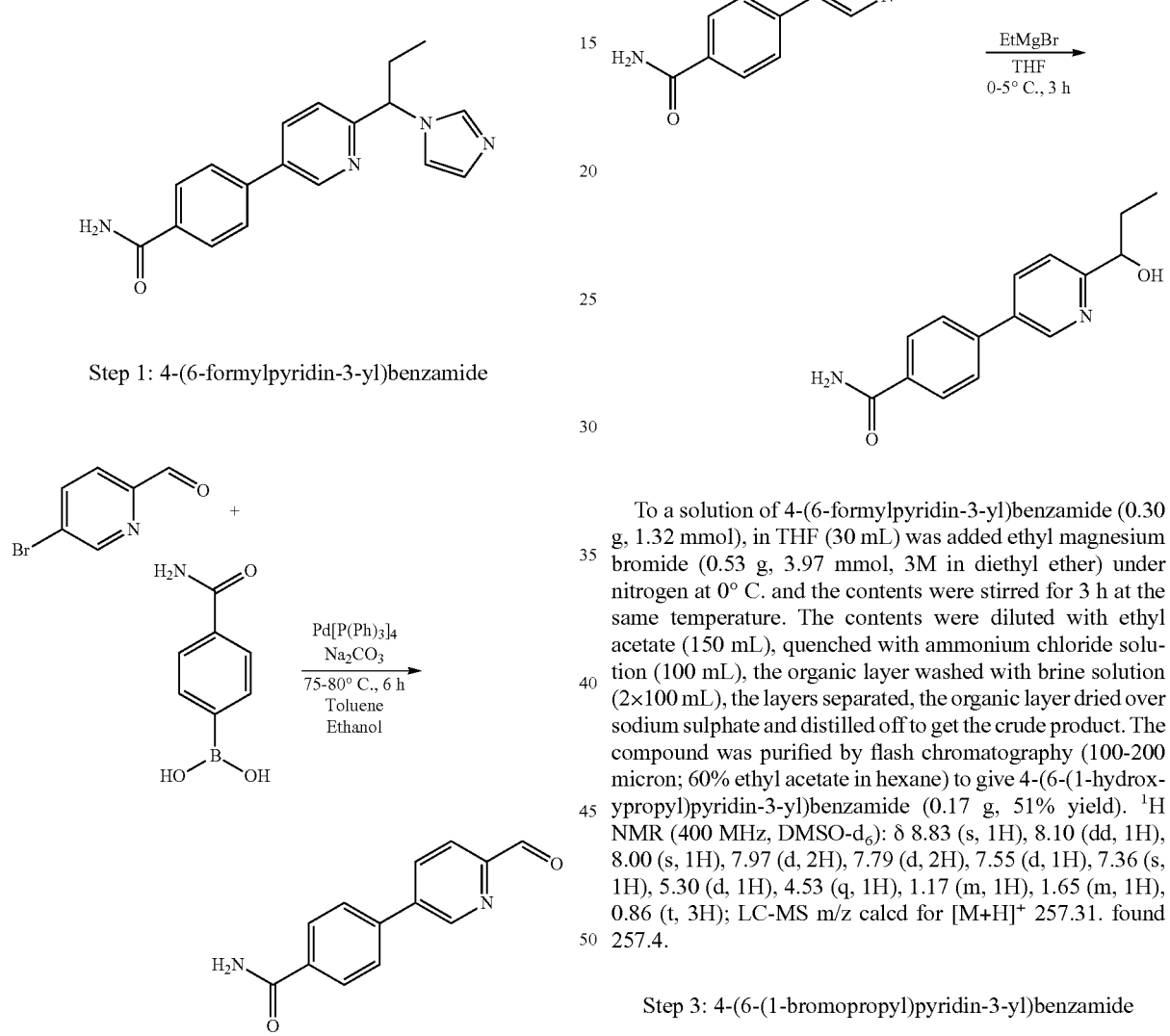

To a solution of 5-bromo picolinaldehyde (0.7 g, 3.76 mmol) in toluene (100 mL) and ethanol (75 mL) was added (4-carbamoylphenyl)boronic acid (1.24 g, 7.52 mmol), 2M sodium carbonate (2.8 g, 26.32 mmol, 6 mL water), Pd(PPh$_3$)$_4$ (0.217 g, 0.188 mmol) under argon. The resulting mixture was heated at 75-80° C., for 6 h. The contents were cooled to room temperature, diluted with ethyl acetate (150 mL) and washed with bicarbonate solution (2×100 mL) and brine solution (2×100 mL). The organic layer was dried over sodium sulphate and distilled off to obtain the crude product. The crude product was purified by flash chromatography (100-200μ; 35% ethyl acetate in hexane) to afford 4-(6-formylpyridin-3-yl)benzamide (0.53 g, 62% yield). $^1$H NMR (400 MHz, DMSO-d$_6$): δ 10.03 (s, 1H), 9.20 (s, 1H), 8.39 (d, 1H), 8.07 (s, 1H), 8.03 (d, 3H), 7.93 (d, 2H), 7.44 (s, 1H).

Step 2: 4-(6-(1-hydroxypropyl)pyridin-3-yl)benzamide

To a solution of 4-(6-formylpyridin-3-yl)benzamide (0.30 g, 1.32 mmol), in THF (30 mL) was added ethyl magnesium bromide (0.53 g, 3.97 mmol, 3M in diethyl ether) under nitrogen at 0° C. and the contents were stirred for 3 h at the same temperature. The contents were diluted with ethyl acetate (150 mL), quenched with ammonium chloride solution (100 mL), the organic layer washed with brine solution (2×100 mL), the layers separated, the organic layer dried over sodium sulphate and distilled off to get the crude product. The compound was purified by flash chromatography (100-200 micron; 60% ethyl acetate in hexane) to give 4-(6-(1-hydroxypropyl)pyridin-3-yl)benzamide (0.17 g, 51% yield). $^1$H NMR (400 MHz, DMSO-d$_6$): δ 8.83 (s, 1H), 8.10 (dd, 1H), 8.00 (s, 1H), 7.97 (d, 2H), 7.79 (d, 2H), 7.55 (d, 1H), 7.36 (s, 1H), 5.30 (d, 1H), 4.53 (q, 1H), 1.17 (m, 1H), 1.65 (m, 1H), 0.86 (t, 3H); LC-MS m/z calcd for [M+H]$^+$ 257.31. found 257.4.

Step 3: 4-(6-(1-bromopropyl)pyridin-3-yl)benzamide

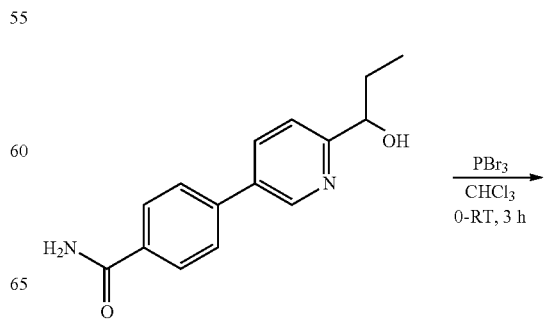

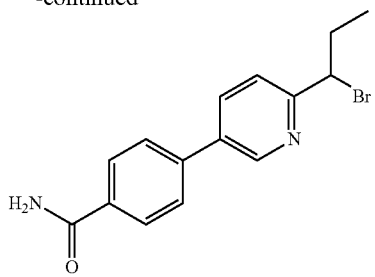

To a solution of 4-(6-(1-hydroxypropyl)pyridin-3-yl)benzamide (0.1 g, 0.39 mmol) in chloroform (15 mL) was added PBr₃ (0.316 g, 1.17 mmol) at 0-5° C. The solution was maintained at the same temperature for 1 h, was slowly warmed to rt and maintained at rt for another 2 h. The contents were diluted with water (75 mL) and chloroform (100 mL), the layers separated, the organic layer was washed with bicarbonate solution (2×30 mL), and the organic layer was dried over sodium sulphate and distilled off to get the crude product. The non-polar impurity was removed by pentane washings (2×7 mL) to provide 4-(6-(1-bromopropyl)pyridin-3-yl)benzamide (0.12 g, crude). LC-MS m/z calcd for [M+H]⁺ 321.03. found 321.0.

Step 4: 4-(6-(1-(1H-imidazol-1-yl)propyl)pyridin-3-yl)benzamide

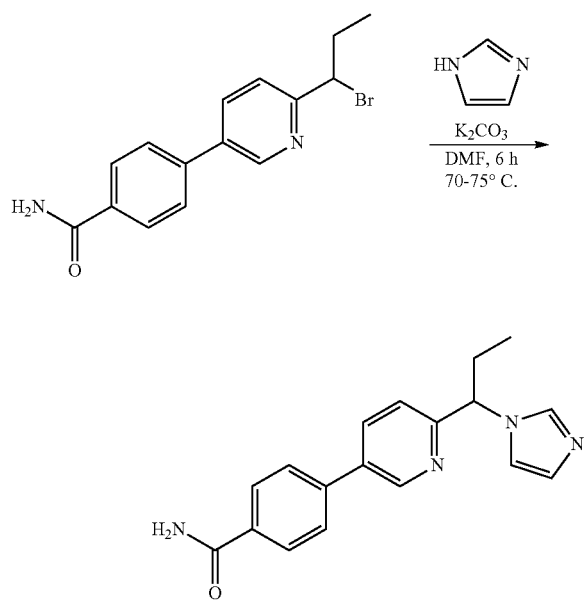

To a solution of imidazole (0.077 g, 1.12 mmol), in DMF (15 mL) was added potassium carbonate (0.26 g, 1.87 mmol) and 4-(6-(1-bromopropyl)pyridin-3-yl)benzamide under nitrogen and the solution was heated to 55-60° C. for 6 h. The contents were cooled to rt, diluted with water (100 mL), extracted with ethyl acetate (2×100 mL), the layers separated, the organic layer washed with brine solution (2×30 mL), the organic layer dried over sodium sulphate and distilled off to get the crude product. The product was purified by preparative TLC (2000; 5% methanol in ethyl acetate) to give 4-(6-(1-(1H-imidazol-1-yl)propyl)pyridin-3-yl)benzamide (15 mg, 13% yield). ¹H NMR (400 MHz, DMSO-d₆): δ 8.92 (s, 1H), 8.13 (d, 1H), 8.11 (s, 1H), 7.97 (d, 2H), 7.80 (t, 3H), 7.40 (d, 2H), 7.31 (s, 1H), 6.89 (s, 1H), 5.38 (q, 1H), 2.27 (m, 2H), 0.82 (t, 3H); LC-MS m/z calcd for [M+H]⁺ 307.37. found 307.3.

Example 11

2-(1-(1H-imidazol-1-yl)propyl)-5-(4-((methoxymethoxy)methyl)-phenyl)pyridine

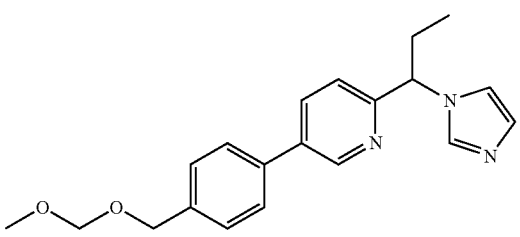 [SMILES: CCC(c1ccc(-c2ccc(COCOC)cc2)cn1)n1ccnc1]

Step 1: 5-(4-(hydroxymethyl)phenyl)picolinaldehyde

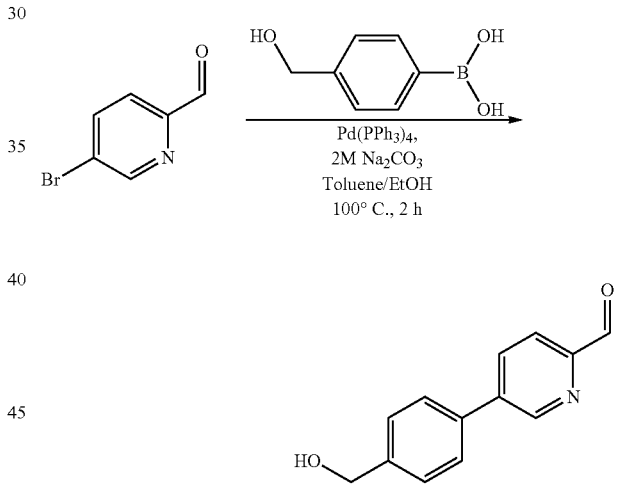

To a solution of 5-bromopicolinaldehyde (0.7 g, 3.76 mmol) in toluene (8 mL) and EtOH (6 mL) was added (4-(hydroxymethyl)phenyl)boronic acid (0.68 g, 4.516 mmol), 2M Na₂CO₃ (5.6 mL, 11.3 mmol) and Pd(PPh₃)₄ (0.2 mg, 0.188 mmol) under argon. The mixture was degassed and heated to 100° C. and stirred for 2 h. After completion of the reaction by monitoring with TLC (60% EtOAc\hexane), the resulting mixture was filtered with Celite® reagent and the filtrate was separated. The filtrate was concentrated, extracted with EtOAc (2×100 mL), washed with water (100 mL), dried over Na₂SO₄ and concentrated in vacuo. The resulting residue was purified by a Biotage Isolera® One column purifier (silica gel 100-200µ) using 38% ethyl acetate in hexane to provide a yellow solid (0.6 g, 75% yield). ¹H NMR (400 MHz, DMSO-d₆): δ 10.01 (s, 1H), 9.14 (d, 1H), 8.306 (dd, 1H), 7.98 (d, 1H), 7.80 (d, 2H), 7.47 (d, 2H), 5.25 (s, 1H), 4.56 (d, 2H); LC-MS: m/z 214.3 [M+H]⁺.

Step 2: 5-(4-((methoxymethoxy)methyl)phenyl)pi-colinaldehyde

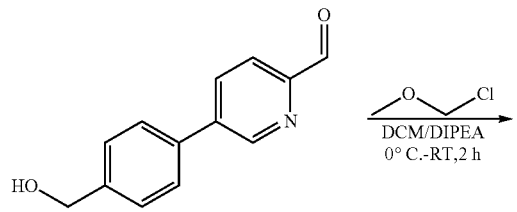

To a solution of 5-(4-(hydroxymethyl)phenyl)picolinaldehyde (0.6 g, 2.81 mmol) in DCM (15 mL) at 0° C. was added diisopropylethyl amine (1.5 mL, 8.4 mmol), followed by chloro(methoxy)methane (1.0 mL, 14.08 mmol). The reaction mixture was stirred at 0° C. for 3 h. After completion of the reaction by monitoring with TLC (30% EtOAc\hexane), the reaction mixture was extracted with dichloromethane (2×100 mL), washed with water (100 mL), dried over Na$_2$SO$_4$ and concentrated in vacuo. The resulting residue was purified by a Biotage Isolera® One column purifier (silica gel 100-200μ) using 13% ethyl acetate in hexane and the product isolated as a yellow viscous liquid (0.36 g, 50% yield). $^1$H NMR (400 MHz, DMSO-d$_6$): δ 10.01 (s, 1H), 9.14 (s, 1H), 8.32 (dd, 1H), 7.996 (d, 1H), 7.83 (d, 2H), 7.50 (d, 2H), 4.67 (s, 2H), 4.60 (s, 2H), 3.28 (s, 3H); LC-MS: m/z 258.1 [M+H]$^+$.

Step 3: 1-(5-(4-((methoxymethoxy)methyl)phenyl)pyridin-2-yl)propan-1-ol

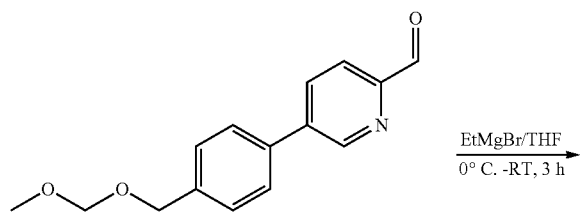

To a solution of 5-(4-((methoxymethoxy)methyl)phenyl) picolinaldehyde (0.36 g, 1.4 mmol) in THF (15 mL) at 0° C. was slowly added 3.0-M ethyl magnesium bromide in diethyl ether (1.4 mL, 4.2 mmol) was added. The reaction mixture was stirred at 0° C. for 3 h. After completion of the reaction by monitoring with TLC (50% EtOAc\hexane), the reaction mixture was quenched with sat'd. NH$_4$Cl (50 mL) solution. The reaction mixture was extracted with EtOAc (3×50 mL), washed with water (2×50 mL), dried over Na$_2$SO$_4$ and concentrated in vacuo. The resulting residue was purified by a Biotage Isolera® One column purifier (silica gel 230-400μ) using 33% ethyl acetate in hexane and the product isolated as a yellow solid (0.15 g, 37% yield). $^1$H NMR (400 MHz, DMSO-d$_6$): δ 8.76 (d, 1H), 8.04 (dd, 1H), 7.69 (d, 2H), 7.53 (d, 1H), 7.44 (d, 2H), 4.66 (s, 2H), 4.57 (s, 2H), 3.30 (s, 3H), 1.79 (m, 1H), 1.65 (m, 1H), 0.862 (t, 3H); LC-MS: m/z 288.5 [M+H]$^+$.

Step 4: 1-(5-(4-((methoxymethoxy)methyl)phenyl) pyridin-2-yl)propylmethane-sulfonate

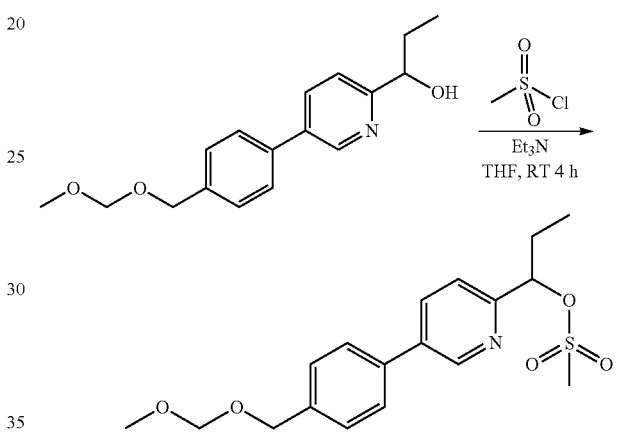

1-(5-(4-((methoxymethoxy)methyl)phenyl)pyridin-2-yl) propan-1-ol (0.1 g 0.348 mmol) and triethylamine (0.1 mL, 1.39 mmol) were dissolved in THF (15 mL) and cooled to 0° C. To this solution was added drop-wise a solution of methanesulfonyl chloride (0.1 mL, 1.39 mmol) over 4 h. The reaction was then stirred at room temperature until the reaction was deemed complete by TLC (50% EtOAc\hexane). The reaction was then poured into water (50 mL) and the aqueous layer was extracted with ethyl acetate (2×50 mL). The combined organic extract was washed with brine, dried over Na$_2$SO$_4$ and concentrated in vacuo to give the mesylate product as a yellow viscous liquid (0.1 g, 83% yield). $^1$H NMR (400 MHz, DMSO-d$_6$): δ 8.998 (s, 1H), 8.4 (d, 1H), 7.79 (q, 3H), 7.48 (d, 2H), 5.73 (t, 1H), 4.66 (s, 2H), 4.58 (s, 2H), 3.32 (s, 3H), 3.20 (s, 3H), 2.02 (m, 2H), 0.91 (t, 3H). LC-MS: m/z 366.1 [M+H]$^+$.

Step 5: 2-(1-(1H-imidazol-1-yl)propyl)-5-(4-((methoxymethoxy)methyl)phenyl)-pyridine

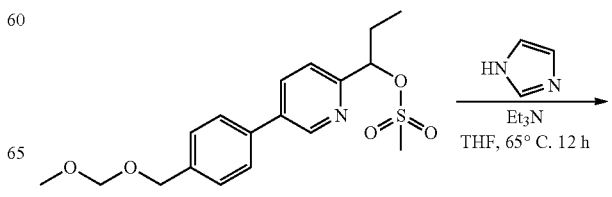

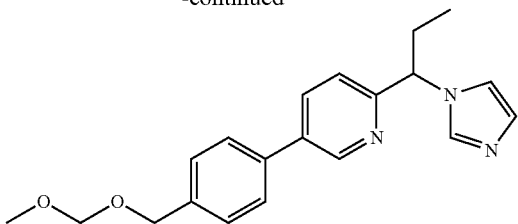

A mixture of 1-(5-(4-((methoxymethoxy)methyl)phenyl)pyridin-2-yl)propyl methanesulfonate (0.1 g, 0.27 mmol), 1H-imidazole (0.037 g, 0.54 mmol) and triethylamine (0.07 mL, 0.54 mmol) in THF (15 mL) was stirred and refluxed at 65° C. for 12 h, cooled to room temperature, poured into ice water (50 mL) and extracted with EtOAc (2×50 mL). The organic layer was separated, dried (Na$_2$SO$_4$), and the solvent was evaporated under vacuo. The resulting residue was purified by preparative TLC using 5% methanol in dichloromethane and isolated as light green viscous liquid (0.04 g, 44% yield). $^1$H NMR (400 MHz, DMSO-d$_6$): δ 8.86 (s, 1H), 8.06 (dd, 1H), 7.81 (s, 1H), 7.69 (d, 2H), 7.44 (d, 2H), 7.37 (d, 1H), 7.30 (s, 1H), 5.36 (q, 1H), 4.65 (s, 2H), 4.56 (s, 2H), 3.30 (s, 3H), 2.25 (m, 2H), 0.81 (t, 3H). LC-MS: m/z 338.2 [M+H]$^+$.

Example 12

2-(1-(1H-imidazol-1-yl)ethyl)-5-(4-fluorophenyl)pyridine

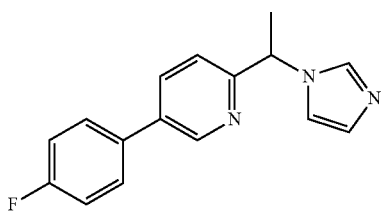 [SMILES: CC(c1ccc(-c2ccc(F)cc2)cn1)n1ccnc1]

Step 1: 1-(5-(4-fluorophenyl)pyridin-2-yl)ethanone

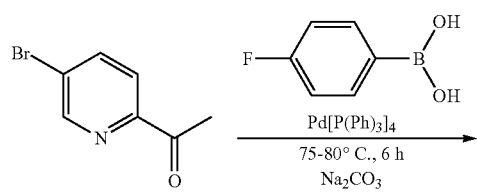

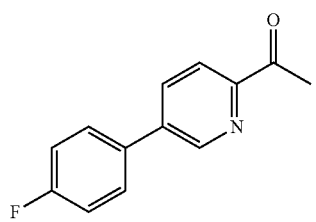

To a solution of 1-(5-bromopyridin-2-yl)ethanone (1.0 g, 4.99 mmol) in toluene (100 mL) and ethanol (50 mL) was added 4-fluoro phenyl-boronic acid (1.4 g, 9.99 mmol), 2M sodium carbonate (3.7 g, 34.99 mmol, 12 mL water), Pd(PPh$_3$)$_4$ (0.228 g, 0.25 mmol) under argon. The resulting mixture was heated at 75-80° C. for 6 h. The contents were cooled to room temperature, diluted with ethyl acetate (150 mL), and washed with bicarbonate solution (2×100 mL) and brine solution (2×100 mL). The organic layer was dried over sodium sulphate and distilled off to obtain the crude product. The product was purified by flash chromatography (100-200μ; 35% ethyl acetate in hexane) to afford 1-(5-(4-fluorophenyl)pyridin-2-yl)ethanone (0.75 g, 66% yield). $^1$H NMR (400 MHz, DMSO-d$_6$): δ 9.12 (s, 1H), 8.25 (dd, 1H), 8.00 (d, 1H), 7.86 (m, 2H), 7.36 (t, 2H), 2.65 (s, 3H); LC-MS m/z calculated for [M+H]$^+$ 216.23 found, 216.0.

Step 2: 1-(5-(4-fluorophenyl)pyridin-2-yl)ethanol

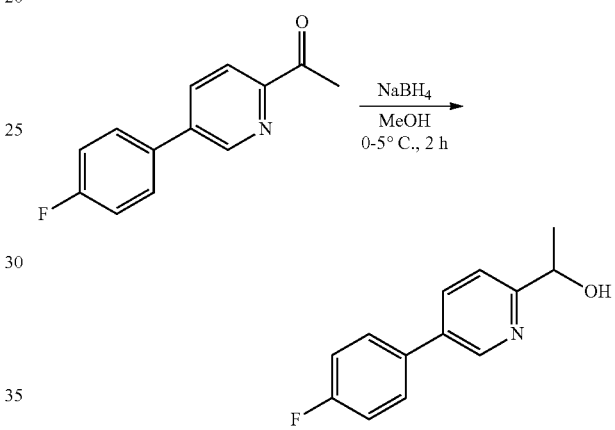

To a solution of 1-(5-(4-fluorophenyl)pyridin-2-yl)ethanone (0.75 g, 3.48 mmol) in MeOH (20 mL) was added NaBH$_4$ (0.264 g, 6.97 mmol) and the contents stirred at 0-5° C. for 2 h. The mixture was diluted with ethyl acetate (150 mL) and then washed with ammonium chloride solution (2×50 mL) and brine solution (2×100 mL). The organic layer was dried over sodium sulphate and distilled off to obtain the crude compound. The crude product was purified by flash chromatography (230-400; 35% ethyl acetate in hexane) to afford 1-(5-(4-fluorophenyl)pyridin-2-yl)ethanol (0.45 g, 60% yield). $^1$H NMR (400 MHz, DMSO-d$_6$): δ 8.74 (s, 1H), 8.03 (dd, 1H), 7.74 (t, 2H), 7.56 (d, 1H), 7.30 (t, 2H), 5.35 (d, 1H), 4.74 (q, 1H), 1.38 (d, 3H); LC-MS m/z calcd for [M+H]$^+$ 218.25. found 218.0.

Step 3: 2-(1-(1H-imidazol-1-yl)ethyl)-5-(4-fluorophenyl)pyridine

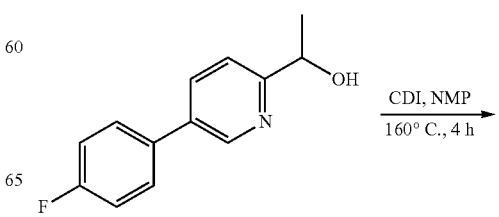

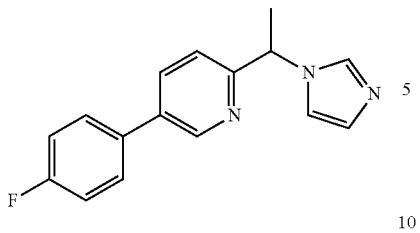

To a solution of 1-(5-(4-fluorophenyl)pyridin-2-yl)ethanol (0.350 g, 1.61 mmol) in NMP (10 mL) was added CDI (1.35 g, 8.37 mmol) under nitrogen and the mixture heated to 160° C. for 4 h. The contents were cooled to rt, diluted with ethyl acetate (100 mL), washed with ice-cold water (2×100 mL), bicarbonate (2×50 mL) and brine solution (2×50 mL), the layers separated, the organic layer dried over sodium sulphate and distilled off to provide the crude product. The product was purified by preparative TLC using (2000μ; 5% methanol in ethyl acetate) to give 2-(1-(1H-imidazol-1-yl)ethyl)-5-(4-fluorophenyl)pyridine (80 mg, 19% yield). $^1$H NMR (400 MHz, DMSO-d$_6$): δ 8.83 (s, 1H), 8.04 (d, 1H), 7.81 (s, 1H), 7.74 (t, 2H), 7.28 (m, 4H), 6.90 (s, 1H), 5.64 (q, 1H), 1.81 (d, 3H); LC-MS m/z calcd for [M+H]$^+$ 268.31. found 268.2.

Step 4: 2-(1-(1H-imidazol-1-yl)ethyl)-5-(4-fluorophenyl)pyridine hydrochloride salt

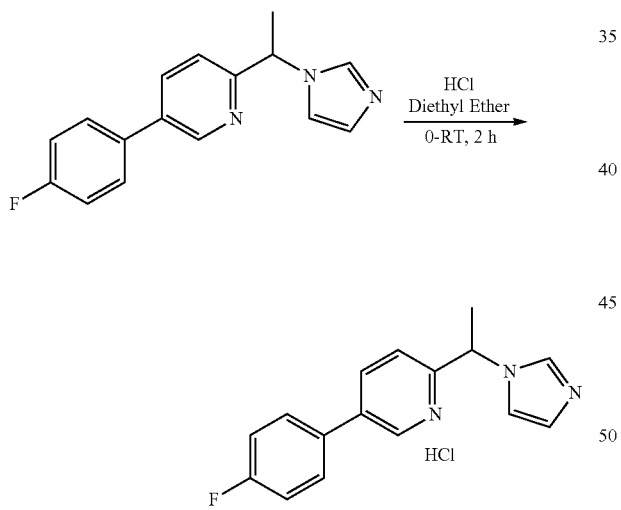

To a solution of 2-(1-(1H-imidazol-1-yl)ethyl)-5-(4-fluorophenyl)pyridine (0.13 g, 0.486 mmol) in diethyl ether (15 mL) was added HCl (0.3 mL, 3M solution in diethyl ether) under nitrogen at 0° C. The mixture was stirred at the same temperature for 1 h, warmed to rt and maintained at rt for another 2 h. The solid material was filtered, pentane washed (2×7 mL) and dried to obtain the hydrochloride salt of 2-(1-(1H-imidazol-1-yl)ethyl)-5-(4-fluorophenyl)pyridine as an off-white solid (0.12 g, 82% yield). $^1$H NMR (400 MHz, DMSO-d$_6$): δ 14.7 (brs, 1H), 9.38 (s, 1H), 8.83 (s, 1H), 8.14 (d, 1H), 7.86 (s, 1H), 7.77 (t, 2H), 7.64 (s, 1H), 7.57 (d, 1H), 7.32 (t, 2H), 5.95 (q, 1H), 1.91 (d, 3H); LC-MS m/z calcd for [M+H]$^+$ 268.31. found 268.4.

Example 13

2-(1-(1H-imidazol-1-yl)ethyl)-5-(furan-3-yl)pyridine

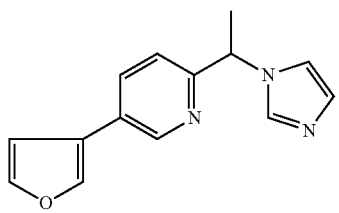 [SMILES: CC(c1ccc(-c2ccoc2)cn1)n1ccnc1]

Step 1: 1-(5-(furan-3-yl)pyridin-2-yl)ethanone

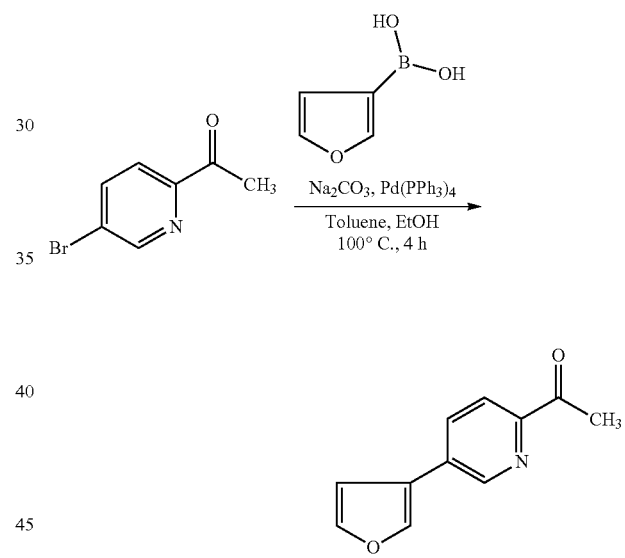

To a solution of 1-(5-bromopyridin-2-yl)ethanone (0.5 g, 2.5 mmol) in toluene (10 mL) and ethanol (5 mL) was added furan-3-ylboronic acid (0.335 g, 3.0 mmol) and a 2 M solution of aq. Na$_2$CO$_3$. The reaction mixture was degassed with argon, Pd(PPh$_3$)$_4$ (0.144 g, 0.125 mmol) was added, the reaction mixture was degassed with argon for 10 min, and the reaction was heated to 100° C. for 4 h. The reaction mixture was evaporated under vacuum to remove the ethanol, diluted with water (30 mL), extracted with ethyl acetate (100 mL), dried over sodium sulphate, filtered and evaporated under reduced pressure to obtain crude product. The crude product was purified by Biotage Isolera® One column (using 10% ethyl acetate and hexane) to give 1-(5-(furan-3-yl)pyridin-2-yl)ethanone (0.35 g, 74% yield); $^1$H NMR (400 MHz, DMSO-d$_6$): δ 9.00 (s, 1H), 8.44 (s, 1H), 8.20-8.17 (m, 1H); 7.95 (d, 1H), 7.83 (s, 1H), 7.13 (s, 1H), 2.57 (s, 3H): LC-MS m/z calcd for [M+H]$^+$ 187.06. found 188.0.

Step 2: 1-(5-(furan-3-yl)pyridin-2-yl)ethanol

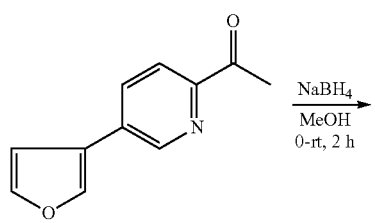

To a solution of 1-(5-(furan-3-yl)pyridin-2-yl)ethanone (0.2 g, 1.0752 mmol) in MeOH (10 ml) was added sodium borohydride (0.0795 g, 2.150 mmol) at 0° C., the reaction mixture warmed to room temperature and was stirred for 2 h. The reaction mixture was evaporated under reduced pressure to remove the methanol, diluted with water (15 mL), extracted with ethyl acetate (200 mL), dried over sodium sulphate and concentrated under reduced pressure to obtain crude product. The crude product was purified by Biotage Isolera® One column (using 20% ethyl acetate and hexane to give 1-(5-(furan-3-yl)pyridin-2-yl)ethanol as a colorless liquid (0.150 g, 73% yield). $^1$H NMR (400 MHz, DMSO-$d_6$): δ 8.68 (s, 1H), 7.76 (t, 2H), 7.52 (s, 1H); 7.28 (t, 1H), 6.71 (s, 1H), 4.91 (d, 1H), 4.14-4.07 (m, 1H), 1.52 (d, 3H): LC-MS m/z calcd for [M+H]$^+$ 189.08. found 190.0.

Step 3: 2-(1-bromoethyl)-5-(furan-3-yl)pyridine

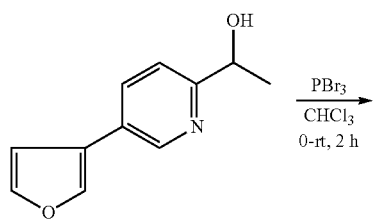

To a solution of 1-(5-(furan-3-yl)pyridin-2-yl)ethanol (0.075 g, 0.403 mmol) in chloroform (5 ml) was added PBr$_3$ (0.321 g, 1.209 mmol), at 0-5° C., the reaction maintained at the same temperature for 15 min, the reaction was slowly warmed to rt and was maintained at rt for another 2 h. The contents were diluted with ethyl acetate (100 mL), bicarbonate solution (10 mL) was added, the organic layer was separated, the organic layer dried over sodium sulphate and distilled to provide 2-(1-bromoethyl)-5-(furan-3-yl)pyridine (0.075 g, 75% yield). LC-MS m/z calcd for [M+H]$^+$ 253.99. found 254.0.

Step 4: 2-(1-(1H-imidazol-1-yl)ethyl)-5-(furan-3-yl) pyridine

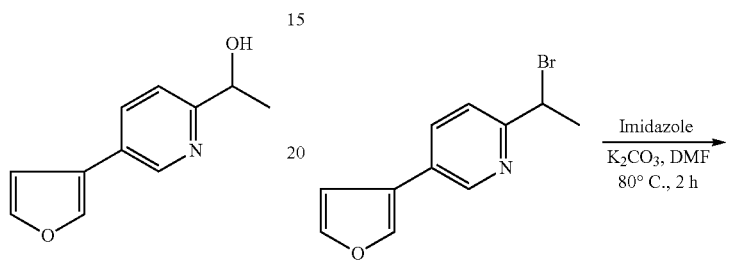

To a solution of imidazole (0.0404 g, 0.595 mmol) in DMF (4 ml) was added potassium carbonate (0.123 g, 0.892 mmol) and 2-(1-bromoethyl)-5-(furan-3-yl)pyridine (0.075 g, 0.297 mmol) under nitrogen and the mixture was heated to 70° C. for 3 h. The contents were cooled to rt, sodium bicarbonate was added, the product extracted with ethyl acetate (100 ml), the organic layer was separated, the organic layer was dried over sodium sulphate and concentrated to obtain the crude product. The crude compound was purified by preparative TLC using (5% MeOH/DCM) to provide 2-(1-(1H-imidazol-1-yl)ethyl)-5-(furan-3-yl)pyridine as a yellow liquid (0.020 g, 28% yield). $^1$H NMR (400 MHz, DMSO-$d_6$): δ 8.81 (s, 1H), 8.25 (s, 1H), 7.97 (s, 1H), 7.84 (s, 1H), 7.76 (s, 1H), 7.31 (s, 1H), 6.88 (d, 2H), 5.25 (t, 1H), 3.87 (s, 3H), 2.25-2.12 (m, 2H), 0.82 (t, 3H): LC-MS m/z calcd for [M+H]$^+$ 240.11. found 240.4.

Example 14

4-(6-(1-(1H-imidazol-1-yl)ethyl)pyridin-3-yl)aniline

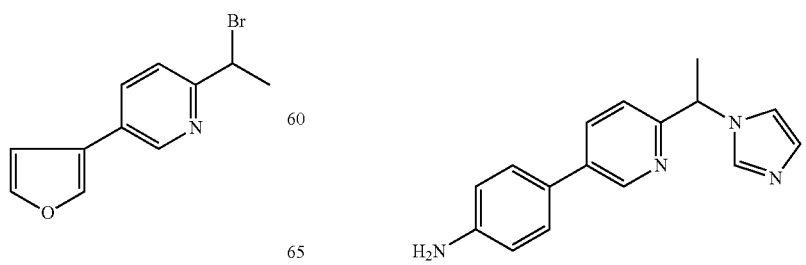

Step 1: 1-(5-(4-nitrophenyl)pyridin-2-yl)ethanone

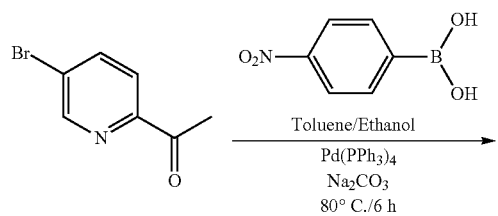

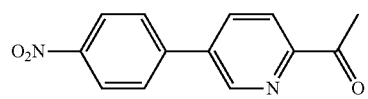

To a stirred solution of 1-(5-bromopyridin-2-yl)ethanone (100 mg, 0.5 mmol) in toluene (4 mL) and ethanol (2 mL) was added (4-nitrophenyl)boronic acid (160 mg, 1 mmol), 2M Na$_2$CO$_3$ (1.4 mL), and Pd(PPh$_3$)$_4$ (6 mg, 0.005 mmol), the reaction was purged with argon, and then heated at 80° C. for about 6 h. The reaction mixture was concentrated, diluted with water (50 mL), and extracted with ethyl acetate (2×100 mL). The combined organic extracts were washed with brine solution (10 mL), organic layer was dried over Na$_2$SO$_4$ and concentrated under vacuum to obtain crude product. The crude product was purified by flash chromatography (silica gel, 60-120µ) using 10% ethyl acetate in hexane eluent to afford 1-(5-(4-nitrophenyl)pyridin-2-yl)ethanone as off white solid (105 mg, 86% yield). $^1$H NMR (400 MHz, DMSO-d$_6$): δ 9.14 (s, 1H), 8.40-8.34 (m, 3H), 8.08 (dd, 3H), 2.67 (s, 3H), LC-MS m/z calcd for [M+H]$^+$ 243.07. found 243.2.

Step 2: 1-(5-(4-nitrophenyl)pyridin-2-yl)ethanol

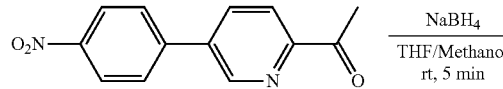

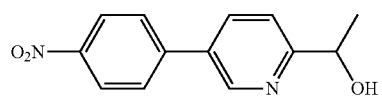

To a stirred solution of 1-(5-(4-nitrophenyl)pyridin-2-yl) ethanone (100 mg, 0.4 mmol) in THF (2 mL) and methanol (2 mL) was added NaBH$_4$ (3 mg, 0.8 mmol) at rt and the reaction was stirred at rt for about 5 min. The reaction mixture was diluted with water (10 mL) and extracted with ethyl acetate (2×100 mL). The combined organic extracts were washed with brine solution (10 mL), organic layer was dried over Na$_2$SO$_4$ and concentrated under vacuum to obtain 1-(5-(4-nitrophenyl)pyridin-2-yl)ethanol as off white solid (100 mg, 100% yield). $^1$H NMR (400 MHz, DMSO-d$_6$): δ 8.88 (d, 1H), 8.31 (d, 2H), 8.19 (dd, 1H), 8.01 (d, 2H), 7.64 (d, 1H), 5.43 (d, 1H), 4.78 (t, 1H), and 1.38 (t, 3H).

Step 3: 2-(1-bromoethyl)-5-(4-nitrophenyl)pyridine

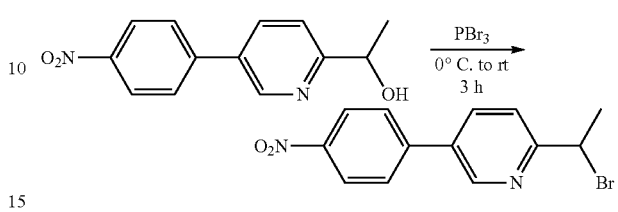

To a stirred solution of 1-(5-(4-nitrophenyl)pyridin-2-yl) ethanol (95 mg, 0.3 mmol) in chloroform (3 mL) was added PBr$_3$ (0.1 mL, 1.1 mmol) at 0° C. and the reaction was stirred at 0° C. for about 3 h. The reaction mixture was quenched with saturated NaHCO$_3$ solution (10 mL) and extracted with DCM (2×100 mL). The combined organic extracts were washed with brine solution (10 mL), organic layer was dried over Na$_2$SO$_4$ and concentrated under vacuum to obtain crude 2-(1-bromoethyl)-5-(4-nitrophenyl)pyridine as off brown liquid (95 mg, 79% yield). $^1$H NMR (400 MHz, DMSO-d$_6$): δ 8.98 (d, 1H), 8.31 (d, 2H), 8.22 (dd, 1H), 8.01 (d, 2H), 7.70 (d, 1H), 5.55 (dd, 1H), 2.04 (d, 3H), LC-MS m/z calcd for [M+H]$^+$ 309.00. found 309.3.

Step 4: 2-(1-(1H-imidazol-1-yl)ethyl)-5-(4-nitrophenyl)pyridine

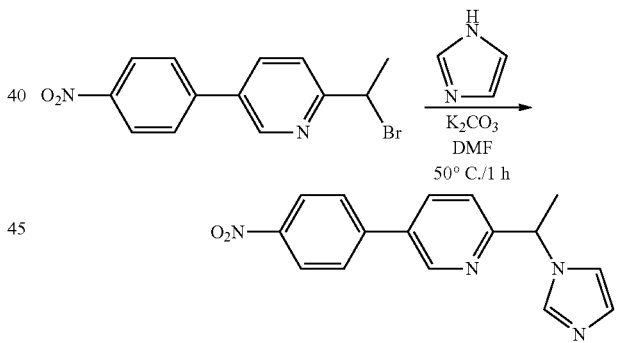

To a stirred solution of 1H-imidazole (13 mg, 0.19 mmol) in DMF (2 mL) was added 2-(1-bromoethyl)-5-(4-nitrophenyl)pyridine (50 mg, 0.1 mmol) and K$_2$CO$_3$. The reaction was heated at 50° C. for about 1 h. The reaction mixture was diluted with water (20 mL) and extracted with ethyl acetate (2×100 mL). The combined organic extracts were washed with brine solution (10 mL), organic layer was dried over Na$_2$SO$_4$ and concentrated under vacuum to obtain crude product. The crude product was purified by flash chromatography (silica gel, 100-200µ) using 2% methanol in DCM eluent to afford 2-(1-(1H-imidazol-1-yl)ethyl)-5-(4-nitrophenyl)pyridine as off white solid (50 mg, 58% yield). $^1$H NMR (400 MHz, DMSO-d$_6$): δ 8.97 (s, 1H), 8.31 (d, 2H), 8.22 (dd, 1H), 8.01 (d, 2H), 7.82 (s, 1H), 7.30 (t, 2H), 6.91 (s, 1H), 5.71-5.65 (m, 1H), 1.84 (d, 3H), LC-MS m/z calcd for [M+H]$^+$ 295.11. found 295.4.

Step 5: 4-(6-(1-(1H-imidazol-1-yl)ethyl)pyridin-3-yl)aniline

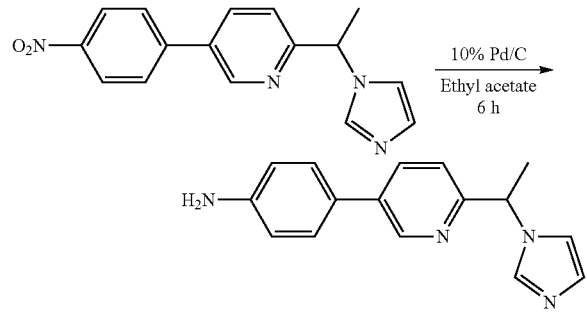

To a stirred solution of 2-(1-(1H-imidazol-1-yl)ethyl)-5-(4-nitrophenyl)pyridine (255 mg, 0.86 mmol) in ethyl acetate (10 mL) was added 10% Pd/C (about 50 mg), under nitrogen. The reaction was stirred at rt for about 6 h under hydrogen. The reaction mixture was filtered through a Celite® bed and the filtrate was concentrated under vacuum to obtain crude product. The crude product was purified by prep TLC method using 3% methanol in DCM to provide 4-(6-(1-(1H-imidazol-1-yl)ethyl)pyridin-3-yl)aniline as off white solid (160 mg, 70% yield). $^1$H NMR (400 MHz, DMSO-d$_6$): δ 8.71 (d, 1H), 7.87 (dd, 1H), 7.78 (s, 1H), 7.36 (d, 2H), 7.24 (s, 1H), 7.14 (d, 1H), 6.88 (s, 1H), 6.61 (t, 2H), 5.60-5.54 (m, 1H), 5.29 (s, 2H), 1.79 (d, 2H), LC-MS m/z calcd for [M+H]$^+$ 265.14. found 265.4.

Example 15

2-(1-(1H-imidazol-1-yl)ethyl)-5-(4-methoxyphenyl)pyridine

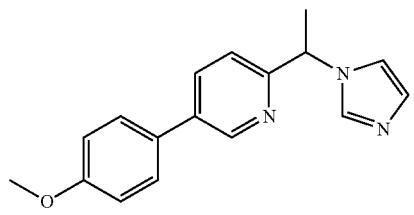 [SMILES: COc1ccc(-c2ccc(C(C)n3ccnc3)nc2)cc1]

Step 1: 1-(5-(4-methoxyphenyl)pyridin-2-yl)ethanone

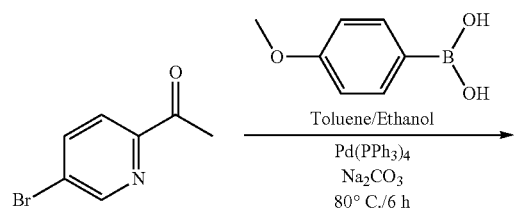

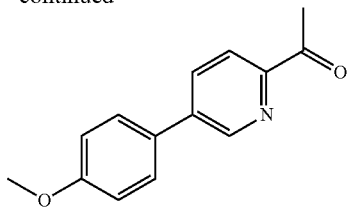

To a stirred solution of 1-(5-bromopyridin-2-yl)ethanone (1.0 g, 5.0 mmol) in toluene (30 mL) and ethanol (20 mL) was added (4-methoxyphenyl)boronic acid (1.52 g, 10 mmol), 2M Na$_2$CO$_3$ (14 mL), Pd(PPh$_3$)$_4$ (0.057 g, 0.05 mmol), the reaction was purged with argon and heated at 80° C. for about 6 h. The reaction mixture was concentrated, diluted with water (100 mL), and extracted with ethyl acetate (2×300 mL). The combined organic extracts were washed with brine solution (20 mL), organic layer was dried over Na$_2$SO$_4$ and concentrated under vacuum to obtain crude product. The crude product was purified by flash chromatography (silica gel, 60-120μ) using 10% ethyl acetate in hexane eluent to afford 1-(5-(4-methoxyphenyl)-pyridin-2-yl)ethanone as off white solid (1 g, 88% yield). $^1$H NMR (400 MHz, DMSO-d$_6$): δ 8.99 (s, 1H), 8.20 (d, 1H), 7.96 (d, 1H), 7.76 (d, 2H), 7.027 (d, 2H), 3.80 (s, 3H), 2.63 (s, 3H). LC-MS m/z calcd for [M+H]$^+$ 228.09. found 228.2.

Step 2: 1-(5-(4-methoxyphenyl)pyridin-2-yl)ethanol

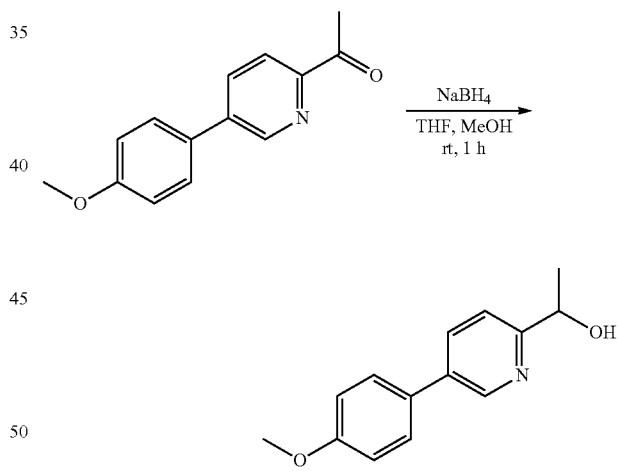

To a stirred solution of 1-(5-(4-methoxyphenyl)pyridin-2-yl)ethanone (1.5 g, 6.6 mmol) in THF (8 mL) and methanol (8 mL) was added NaBH$_4$ (0.4 g, 13.2 mmol) at 0° C. and the reaction was stirred at rt for about 1 h. The reaction mixture was diluted with water (100 mL), extracted with ethylacetate (2×100 mL). The combined organic extracts were washed with brine solution (10 mL), organic layer was dried over Na$_2$SO$_4$ and concentrated under vacuum to obtain 1-(5-(4-methoxyphenyl)-pyridin-2-yl)ethanol as an off-white solid (1.0 g, 66% yield). $^1$H NMR (400 MHz, DMSO-d$_6$): 8.72 (d, 1H), 7.84 (dd, 1H), 7.51 (d, 2H), 7.32 (d, 1H), 7.01 (d, 2H), 4.93 (s, 1H), 4.11 (d, 1H), 3.86 (s, 3H), 1.54 (d, 3H), LC-MS m/z calcd for [M+H]$^+$ 230.1. found 230.3.

Step 3: 2-(1-bromoethyl)-5-(4-methoxyphenyl)pyridine

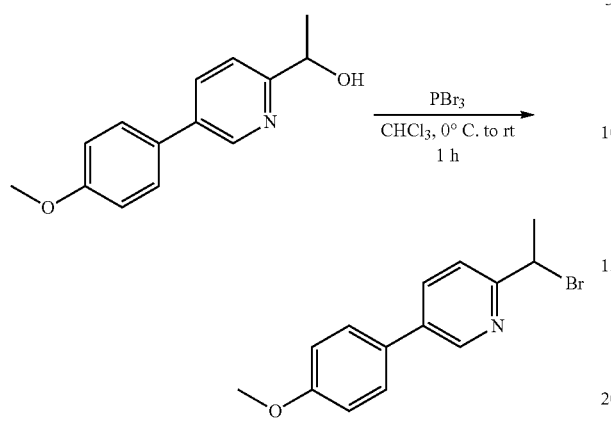

To a stirred solution of 1-(5-(4-methoxyphenyl)pyridin-2-yl)ethanol (0.2 g, 0.8 mmol) in chloroform (4 mL) was added PBr$_3$ (0.3 mL, 1.3 mmol) at 0° C. and the reaction was stirred at 0° C. to rt for about 1 h. The reaction mixture was quenched with saturated NaHCO$_3$ solution (10 mL) and extracted with ethyl acetate (2×100 mL). The combined organic extracts were washed with brine solution (10 mL), the organic layer was dried over Na$_2$SO$_4$ and concentrated under vacuum to obtain crude product. The crude product was purified by flash chromatography (silica gel, 60-120μ) using 10% ethyl acetate in hexane eluent to provide 2-(1-bromoethyl)-5-(4-methoxyphenyl)pyridine (0.15 g, 58% yield). $^1$H NMR (400 MHz, DMSO-d$_6$): δ 8.76 (d, 1H), 7.84 (dd, 1H), 7.51 (dd, 3H), 7.01 (d, 2H), 5.32-5.26 (m, 1H), 3.86 (s, 3H), 2.11 (d, 3H), LC-MS m/z calcd for [M+H]$^+$ 292.0. found 292.3.

Step 4: 2-(1-(1H-imidazol-1-yl)ethyl)-5-(4-methoxyphenyl)pyridine

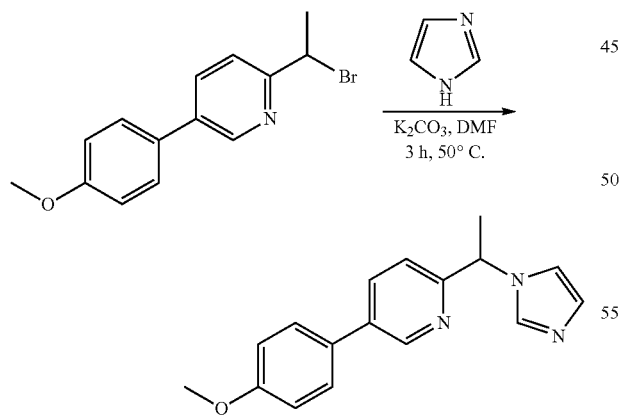

To a stirred solution of 1H-imidazole (0.069 g, 1.0 mmol) in DMF (7 mL) was added 2-(1-bromoethyl)-5-(4-methoxyphenyl)pyridine (0.150 g, 0.50 mmol) and K$_2$CO$_3$ (354 mg, 2.5 mmol). The reaction was heated at 50° C. for about 3 h. The reaction mixture was diluted with water (100 mL) and extracted with ethyl acetate (2×100 mL). The combined organic extracts were washed with brine solution (10 mL), the organic layer was dried over Na$_2$SO$_4$ and concentrated under vacuum to obtain crude product. The crude product was purified by flash chromatography (silica gel, 100-200μ) using 2% methanol in DCM eluent to afford 2-(1-(1H-imidazol-1-yl)ethyl)-5-(4-methoxyphenyl)pyridine as an off-white solid (0.1 g, 69% yield). $^1$H NMR (400 MHz, DMSO-d$_6$): δ 8.80 (d, 1H), 7.99 (dd, 1H), 7.80 (s, 1H), 7.63 (d, 2H), 7.26 (s, 1H), 7.03 (d, 1H), 7.21 (d, 2H), 6.89 (s, 1H), 5.64-5.59 (m, 1H), 3.78 (s, 3H), 1.81 (d, 3H), LC-MS m/z calcd for [M+H]$^+$ 280.14. found 280.2.

Example 16

4-(6-(1-(1H-imidazol-1-yl)ethyl)pyridin-3-yl)phenol

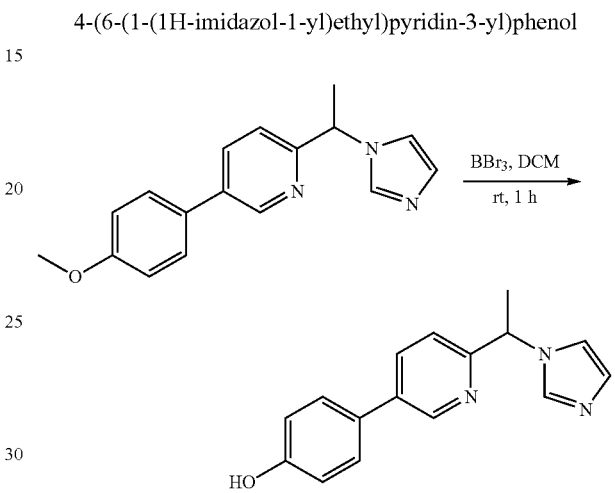

To a stirred solution of 2-(1-(1H-imidazol-1-yl)ethyl)-5-(4-methoxyphenyl)pyridine (0.075 g, 0.26 mmol; prepared as described for Example 15) in DCM (3 mL) was added BBr$_3$ (0.1 mL 0.4 mmol) at 0° C. The reaction was stirred at rt for about 1 h. The reaction mixture was quenched with saturated NaHCO$_3$ solution (5 mL), diluted with water (100 mL), and extracted with DCM (2×100 mL). The combined organic extracts were washed with brine solution (10 mL), organic layer was dried over Na$_2$SO$_4$ and concentrated under vacuum to obtain crude product. The crude product was purified by flash chromatography (silica gel, 60-120) using 4% methanol in DCM eluent to afford 4-(6-(1-(1H-imidazol-1-yl)ethyl)pyridin-3-yl)phenol as an off-white solid (35 mg, 49% yield). $^1$H NMR (400 MHz, DMSO-d$_6$): δ 9.62 (s, 1H), 8.74 (d, 1H), 7.99 (dd, 1H), 7.85 (s, 1H), 7.50 (d, 2H), 7.28 (s, 1H), 7.20 (d, 1H), 6.91 (s, 1H), 6.84 (d, 2H), 5.64-5.59 (m, 1H), 1.80 (d, 3H), LC-MS m/z calcd for [M+H]$^+$ 266.12. found 266.2.

Example 17

4-(6-(1-(1H-imidazol-1-yl)propyl)pyridin-3-yl)cyclohexa-1,3-dienecarbonitrile

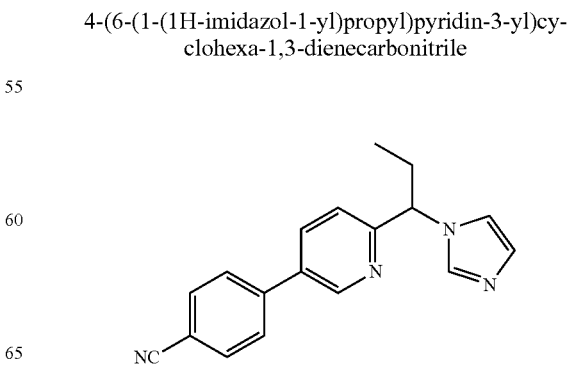

Step 1: 1-(5-bromopyridin-2-yl)propan-1-ol

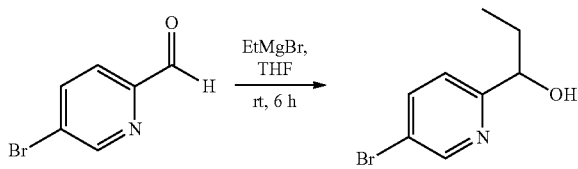

To a solution of 5-bromopicolinaldehyde (2.0 g, 10.8 mmol) in THF (20 mL) was added 3.0 M solution of ethyl magnesium bromide in diethyl ether (7.1 ml, 21.5 mmol) at 0° C. The reaction mixture was allowed to warm to room temperature and was stirred for 6 h. The reaction mixture was quenched with saturated ammonium chloride solution (20 mL) and water (15 mL), extracted with ethyl acetate (200 mL), dried over sodium sulphate and concentrated under reduced pressure to obtain crude product. The crude product was purified by a Biotage Isolera® One column (using 10% ethyl acetate and hexane (0.72 g, (45% yield). $^1$H NMR (400 MHz, DMSO-d$_6$): δ 8.57 (d, 1H), 8.01-7.98 (dd, 1H), 7.445 (d, 1H), 5.36 (d, 1H), 4.49-4.45 (dd, 1H), 1.65-1.61 (m, 2H), 0.815 (t, 3H).

Step 2: 4-(6-(1-hydroxypropyl)pyridin-3-yl)benzonitrile

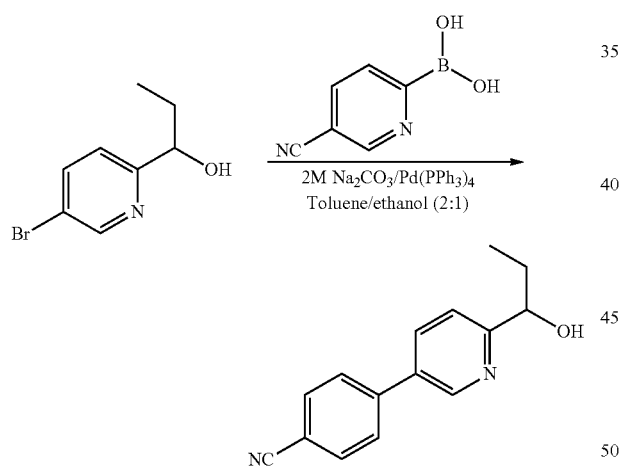

To a solution of 1-(5-bromopyridin-2-yl)propan-1-ol (0.3 g, 1.38 mmol) in toluene (8 mL) and ethanol (4 mL) was added 4-cyano phenyl boronic acid (0.244 g, 1.6 mmol) and a 2 M solution of aq. Na$_2$CO$_3$. The reaction mixture degassed with argon, Pd(PPh$_3$)$_4$ (0.08 g, 0.069 mmol) was added, the reaction mixture was again degassed with argon for 10 min, and heated to 80° C. for 4 h. The reaction mixture was evaporated under vacuum to remove ethanol, the reaction mixture was diluted with water (10 mL), extracted with ethyl acetate (100 mL), dried over sodium sulphate, filtered and evaporated under reduced pressure to obtain crude product. The crude product was purified by a Biotage Isolera® One column (using 15% ethyl acetate and hexane) to give 4-(6-(1-hydroxypropyl)pyridin-3-yl)benzonitrile (0.15 g, 45.45% yield). $^1$H NMR (400 MHz DMSO-d$_6$): δ 8.78 (s, 1H), 7.89 (dd, 1H), 7.78 (d, 2H); 7.69 (d, 2H), 7.39 (d, 1H), 4.77 (t, 1H), 3.90 (s, 1H), 1.91-1.81 (m, 2H), 0.99 (t, 3H).

Step 3: 4-(6-(1-bromopropyl)pyridin-3-yl)benzonitrile

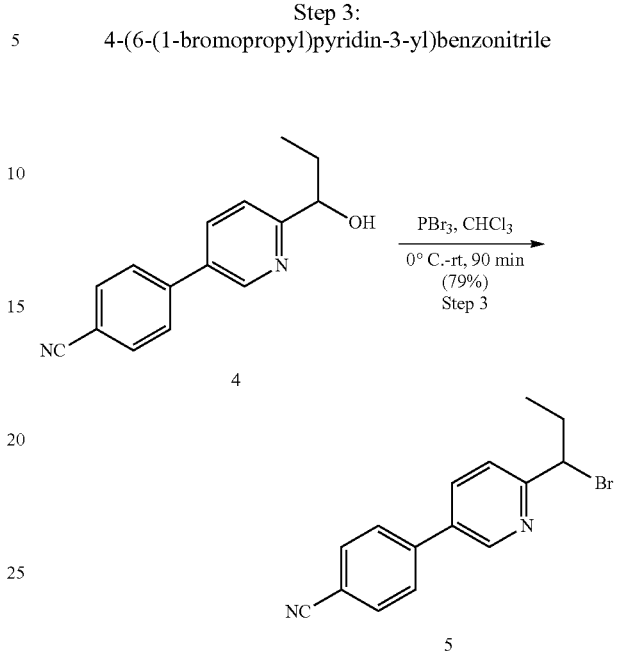

To a solution of 4-(6-(1-hydroxypropyl)pyridin-3-yl)benzonitrile (0.10 g, 0.21 mmol) in chloroform (4 mL) was added PBr$_3$ (0.34 g, 0.63 mmol) at 0-5° C. This temperature was maintained for 15 min, was slowly allowed to rt and was then maintained at rt for another 90 min. The contents were diluted with chloroform (100 mL) and washed with bicarbonate solution (2×30 mL). The organic layer was separated, dried over sodium sulphate and evaporated to provide 4-(6-(1-bromopropyl)pyridin-3-yl)benzonitrile (92 mg, 73% yield).

Step 4: 4-(6-(1-(1H-imidazol-1-yl)propyl)pyridin-3-yl)cyclohexa-1,3-dienecarbonitrile

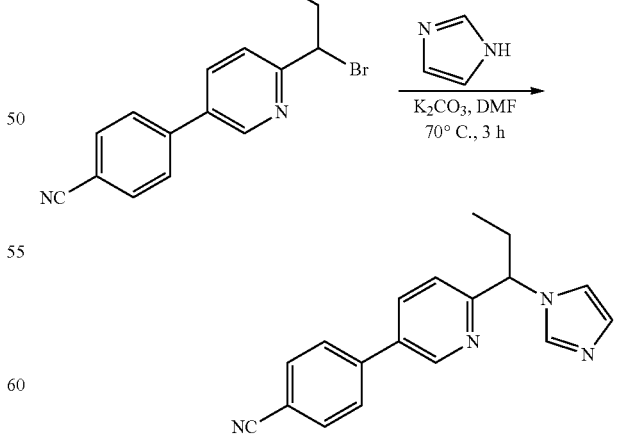

To a solution of imidazole (0.034 g, 0.332 mmol) in DMF (3 ml) was added potassium carbonate (0.11 g, 0.83 mmol) and 4-(6-(1-bromopropyl)pyridin-3-yl)benzonitrile (0.090 g) under nitrogen and the solution was heated to 70° C. for 3 h.

After cooling the contents to rt, sodium bicarbonate was added, extracted with ethyl acetate (50 mL), the organic layer separated, the organic layer dried over sodium sulphate and distilled off to obtain the crude product. The compound was purified by preparative TLC using (2000µ; 5% MeOH/DCM) to provide 4-(6-(1-(1H-imidazol-1-yl)propyl)pyridin-3-yl) cyclohexa-1,3-dienecarbonitrile (0.012 g, 13.9% yield). $^1$H NMR (400 MHz DMSO-d$_6$): δ 8.96 (d, 1H), 8.19 (dd, 1H), 7.96 (d, 5H); 7.47 (d, 1H), 7.39 (s, 1H), 7.01 (s, 1H), 5.45 (t, 1H), 2.26-2.23 (m, 2H), 0.84 (t, 3H): LC-MS m/z calcd for [M+H]$^+$ 289.14. found 289.0.

Example 18

2-(6-(1-(1H-imidazol-1-yl)propyl)pyridin-3-yl)benzonitrile

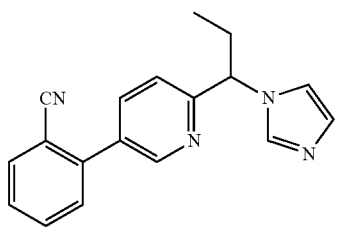 [SMILES: CCC(c1ccc(-c2ccccc2C#N)cn1)n1ccnc1]

Step 1: 2-(6-(1-(1H-imidazol-1-yl)propyl)pyridin-3-yl)benzonitrile

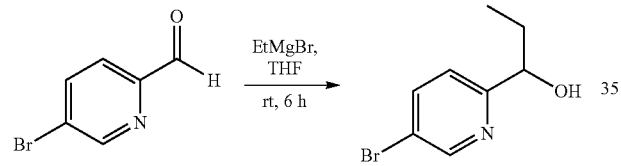

To a solution of 5-bromopicolinaldehyde (2.0 g, 10.8 mmol) in THF (20 mL) was added a 3.0 M solution of ethyl magnesium bromide in diethyl ether (7.1 mL, 21.5 mmol) at 0° C., the reaction mixture was allowed to warm to room temperature and was stirred for 6 h. The reaction mixture was quenched with saturated ammonium chloride solution (20 mL) and water (15 mL), extracted with ethyl acetate (200 mL). dried over sodium sulphate and concentrated under reduced pressure to obtain crude product. The crude product was purified by a Biotage Isolera® One column (using 10% ethyl acetate and hexane) to provide the desired product (0.72 g, 45% yield). $^1$H NMR (400 MHz, DMSO-d$_6$): δ 8.57 (d, 1H), 8.01-7.98 (dd, 1H), 7.44 (d, 1H); 5.36 (d, 1H), 4.49-4.44 (dd, 1H), 1.65-1.61 (m, 2H), 0.82 (t, 3H).

Step 2:
2-(6-(1-hydroxypropyl)pyridin-3-yl)benzonitrile

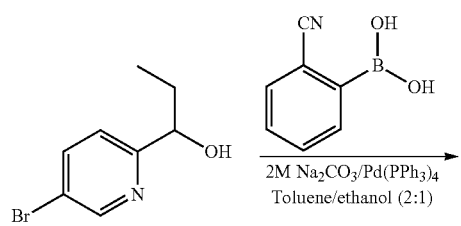

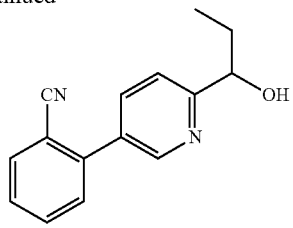

To a solution of 1-(5-bromopyridin-2-yl)propan-1-ol (0.7 g, 3.2 mmol) in toluene (15 mL) and ethanol (8 mL) was added 2-cyano phenyl boronic acid (0.57 g, 3.8 mmol) and a 2M solution of aq. Na$_2$CO$_3$. The reaction mixture was degassed with argon, Pd(PPh$_3$)$_4$ (0.187 g, 0.162 mmol) was added, the reaction mixture was again degassed with argon for 10 min, and the reaction heated to 100° C. for 3 h. The reaction mixture was evaporated under vacuum to remove ethanol, diluted with water (40 mL), extracted with ethyl acetate (200 mL), dried over sodium sulphate, filtered and evaporated under reduced pressure to obtain crude product. The crude product was purified by a Biotage Isolera® One column (using 20% ethyl acetate and hexane) to give 2-(6-(1-hydroxypropyl)pyridin-3-yl)benzonitrile. (0.150 g, 19.4% yield). $^1$H NMR (400 MHz DMSO-d$_6$): δ 8.67 (s, 1H), 8.02-7.97 (m, 2H), 7.82 (t, 1H), 7.69 (d, 1H), 7.63-7.60 (m, 2H), 1.83-1.68 (m, 2H), 0.89 (t, 3H): LC-MS m/z calcd for [M+H]$^+$ 239.11. found 239.0.

Step 3:
2-(6-(1-bromopropyl)pyridin-3-yl)benzonitrile

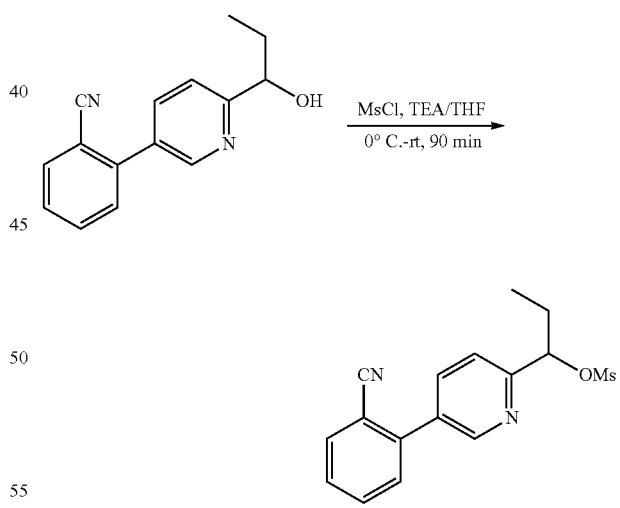

To solution of 2-(6-(1-hydroxypropyl)pyridin-3-yl)benzonitrile (0.05 g) in THF (3 mL) was added triethyl amine (0.042 g), the mixture was stirred for 5 minutes, and then methanesulfonyl chloride was added (0.47 g). The mixture was stirred at room temperature for 90 min. The reaction mixture was quenched with sodium bicarbonate and extracted with ethyl acetate. The organic extracts were dried over sodium sulphate, filtered and concentrated to obtain 1-(5-(2-cyanophenyl)pyridin-2-yl)propyl methanesulfonate (0.050 g, 71% yield), which was used directly in the next step.

Step 4: 2-(6-(1-(1H-imidazol-1-yl)propyl)pyridin-3-yl)benzonitrile

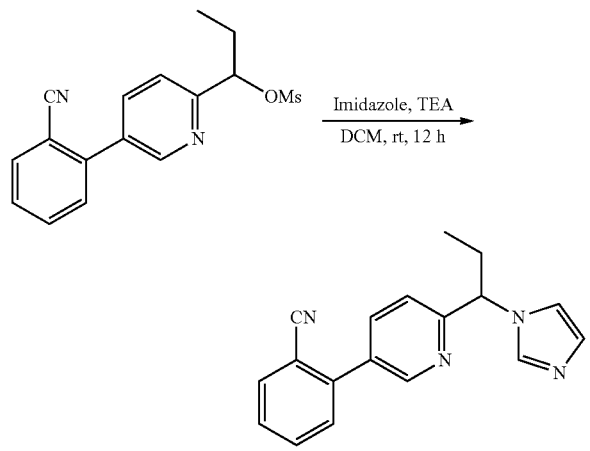

To solution of 1-(5-(2-cyanophenyl)pyridin-2-yl)propyl methanesulfonate (0.050 g, 0.15 mmol) in DCM was added triethyl amine (0.030 g, 0.30 mmol) followed by imidazole (0.20 g, 0.30 mmol) at room temperature. The reaction mixture was stirred for 12 h at room temperature. The reaction mixture was diluted with water (20 mL) and extracted with ethyl acetate (50 mL). The organic extracts were dried over sodium sulphate, filtered and concentrated to obtain the crude compound which was purified by preparative TLC by using 5% MeOH/DCM to give 2-(6-(1-(1H-imidazol-1-yl)propyl)pyridin-3-yl)benzonitrile (10 mg, 24%). $^1$H NMR (400 MHz DMSO-d$_6$): δ 8.77 (s, 1H), 8.04 (dd, 1H), 7.98 (d, 1H), 7.84 (s, 1H), 7.80 (d, 1H), 7.68 (d, 1H), 7.63 (t, 1H), 7.44 (d, 1H), 7.34 (s, 1H), 6.92 (s, 1H), 5.43 (dd, 1H), 2.31-2.20 (m, 2H), 0.83 (t, 3H); LC-MS m/z calcd for [M+H]$^+$ 289.14. found 289.5.

Example 19

2-(1-(1H-imidazol-1-yl)propyl)-5-(4-fluorophenyl)-1,3,4-thiadiazole

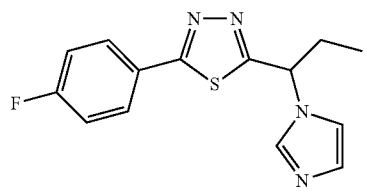 [SMILES: CCC(c1nnc(-c2ccc(F)cc2)s1)n1ccnc1]

Step 1: Ethyl 5-amino-1,3,4-thiadiazole-2-carboxylate

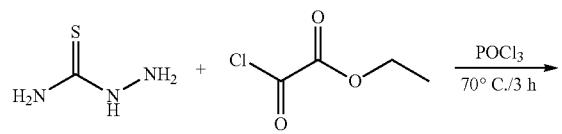

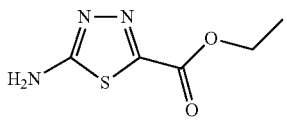

To a solution of hydrazinecarbothioamide (10 g, 54.8 mmol) in POCl$_3$ (25 mL) was added ethyl 2-chloro-2-oxacetate (6.1 mL, 54.8 mmol). The reaction was heated to 70° C. and stirred for 5 h. POCl$_3$ was completely removed from the reaction mixture under vacuum. The residue was diluted with ice cold water (150 mL) and basified to pH 8 with saturated sodium bicarbonate solution and then extracted with ethyl acetate (200 mL). The organic layer was separated and dried over Na$_2$SO$_4$, and the solvent was evaporated to obtain crude product. The crude product was purified by flash chromatography (silica gel 100-200μ, 2% methanol and dichloromethane) to afford ethyl 5-amino-1,3,4-thiadiazole-2-carboxylate as a yellow solid (3.1 g, 24% yield). $^1$H NMR (400 MHz, DMSO-d$_6$): δ 7.94 (s, 2H), 4.29 (q, 2H), 1.27 (t, 3H); LC-MS m/z calcd for [M+H]$^+$ 174.03. found 174.1.

Step 2: ethyl 5-bromo-1,3,4-thiadiazole-2-carboxylate

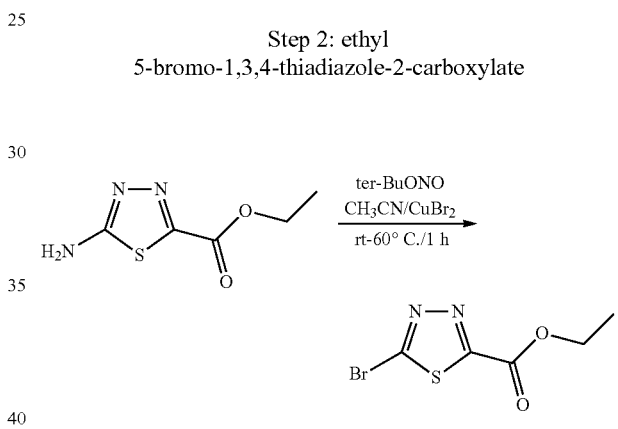

To a stirred solution of ethyl 5-amino-1,3,4-thiadiazole-2-carboxylate (3.1 g, 17.8 mmol) in acetonitrile (50 mL) at room temperature was added copper (II) bromide (7.95 g, 35.6 mmol) and the mixture was stirred for 20 min. Tertiary butyl nitrite (3.67 g, 35.63 mmol) was then added drop wise for 10 min, and the reaction mixture was heated to 60° C. for 30 min. The reaction mixture was concentrated under reduced pressure, diluted with water (300 mL), and then extracted with ethyl acetate (500 m:). The organic layer was separated and dried over anhydrous sodium sulphate, and evaporated to afford ethyl 5-bromo-1,3,4-thiadiazole-2-carboxylate as a brown solid (3.0 g, 74% yield). $^1$H NMR (400 MHz, CDCl$_3$): δ 4.53-4.51 (m, 2H), 1.45-1.43 (m, 3H); LC-MS m/z calcd for [M+H]$^+$ 238.92. found 238.9.

Step 3: (5-bromo-1,3,4-thiadiazol-2-yl)methanol

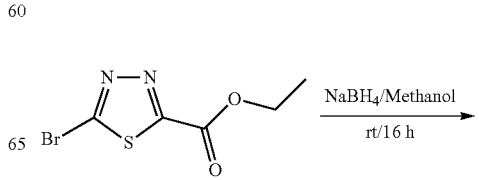

-continued

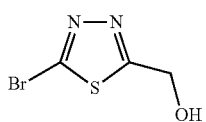

A solution of ethyl 5-bromo-1,3,4-thiadiazole-2-carboxylate (3.0 g, 12.6 mmol) in methanol (50 mL) was cooled to 0° C. and then sodium borohydride (1.40 g, 38.0 mmol) was added slowly. The reaction mixture was allowed to stir for 16 hours at room temperature. The reaction mixture was quenched with acetic acid (3 mL), extracted with ethyl acetate (200 mL), the organic layer was washed with sodium bicarbonate solution (20 mL) followed by brine solution (10 mL), the organic layer was separated, dried over sodium sulphate and evaporated under reduced pressure to obtain crude product. The crude product was purified by a Biotage Isolera® One column (using 25% ethyl acetate and hexane) to give (5-bromo-1,3,4-thiadiazol-2-yl)methanol as a white solid (1.8 g, 73% yield). $^1$H NMR (400 MHz, DMSO-$d_6$): δ 6.31 (t, 3H), 4.85 (d, 2H); LC-MS m/z calcd for [M+H]$^+$ 194.91. found 195.0.

Step 4:
(5-(4-fluorophenyl)-1,3,4-thiadiazol-2-yl)methanol

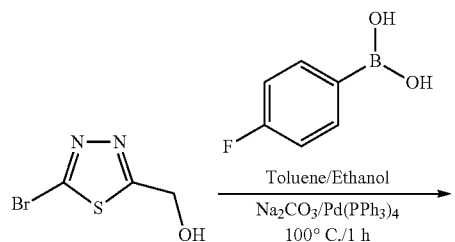

To a solution of (5-bromo-1,3,4-thiadiazol-2-yl)methanol (1.2 g, 6.15 mmol) in toluene (40 ml) and ethanol (40 ml) was added 4-fluorophenyl boronic acid (1.03 g, 7.38 mmol) and 2 M aqueous $Na_2CO_3$. The reaction mixture was degassed with argon, Pd(PPh$_3$)$_4$ (0.354 g, 0.355 mmol) was added, the reaction mixture was degassed again with argon for 10 min, and then heated to 100° C. for 2 h. The reaction mixture was evaporated under vacuum to remove ethanol, the reaction mixture was diluted with water (50 mL), and extracted with ethyl acetate (200 mL). The organic extracts were dried over sodium sulphate, filtered and evaporated under reduced pressure to obtain crude product. The crude product was purified by Biotage Isolera® One column (using 30% ethyl acetate and hexane) to give (5-(4-fluorophenyl)-1,3,4-thiadiazol-2-yl)methanol as a pale yellow solid (0.85 g, 65% yield); LC-MS m/z calcd for [M+H]$^+$ 211.03. found 211.1

Step 5: 5-(4-fluorophenyl)-1,3,4-thiadiazole-2-carbaldehyde

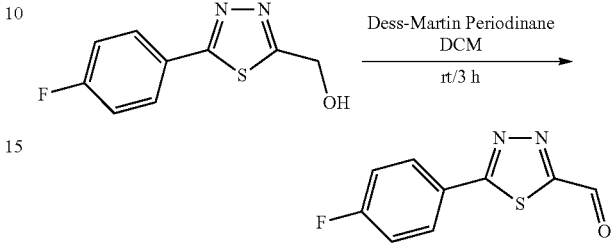

To a solution of 5-(4-fluorophenyl)-1,3,4-thiadiazol-2-yl)methanol (0.85 g, 4.1 mmol) in dichloromethane (30 ml) at 0° C. was slowly added Dess-Martin Periodinane (3.4 g, 8.1 mmol). The reaction mixture was allowed to warm to room temperature for 3 h. To the mixture was then added saturated sodium bicarbonate solution (20 mL) and sodium thiosulphate (2 g). The reaction mixture was extracted with ethyl acetate (200 mL). The organic extracts were dried over sodium sulphate, filtered and evaporated under reduced pressure to obtain crude product. The crude compound was purified by flash column chromatography (using 20% ethyl acetate in hexane) to obtain 5-(4-fluorophenyl)-1,3,4-thiadiazole-2-carbaldehyde as a white solid (0.45 g, 53% yield). $^1$H NMR (400 MHz, DMSO-$d_6$): δ 10.17 (s, 1H), 8.19 (q, 2H), 7.45 (t, 2H); LC-MS m/z calcd for [M+H]$^+$ 209.21. found 209.1.

Step 6: 1-(5-(4-fluorophenyl)-1,3,4-thiadiazol-2-yl)propan-1-ol

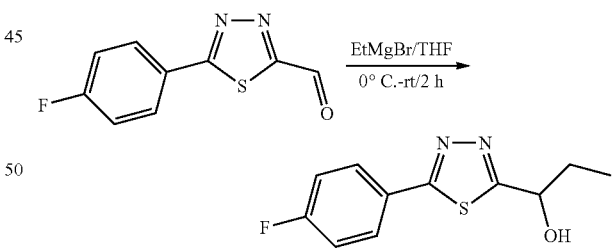

To a solution of 5-(4-fluorophenyl)-1,3,4-thiadiazole-2-carbaldehyde (0.2 g, 0.96 mmol) in THF (8 mL) was added 3.0 M solution of ethyl magnesium bromide in diethyl ether (0.96 mL, 2.9 mmol) at 0° C. The reaction mixture was allowed to warm to room temperature and was stirred for 2 h. The reaction mixture was quenched with saturated ammonium chloride solution (15 mL) and water (15 mL), and extracted with ethyl acetate (100 mL). The organic extracts were dried over sodium sulphate and concentrated under reduced pressure to afford 1-(5-(4-fluorophenyl)-1,3,4-thiadiazol-2-yl)propan-1-ol as a yellow solid (0.10 g, 45% yield). $^1$H NMR (400 MHz, DMSO-$d_6$): δ 8.0-8.03 (m, 1H), 7.39-

7.35 (m, 2H), 6.36 (d, 1H), 4.92-4.89 (m, 1H), 1.89-1.78 (m, 2H), 0.95 (t, 3H); LC-MS m/z calcd for [M+H]+ 239.06. found 239.1.

Step 7: 2-(1-(1H-imidazol-1-yl)propyl)-5-(4-fluorophenyl)-1,3,4-thiadiazole

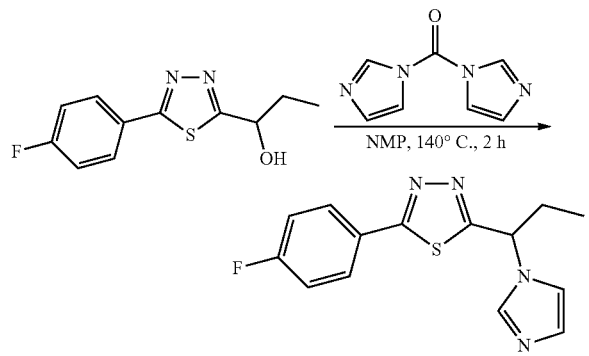

To a solution of 1-(5-(4-fluorophenyl)-1,3,4-thiadiazol-2-yl)propan-1-ol (0.1 g, 0.42 mmol) in NMP (4 mL) was added CDI (0.353 g, 2.18 mmol) at room temperature. The mixture was heated to 140° C. for 2 hours. The reaction was diluted with ice-cold water (200 mL) and extracted with ethyl acetate (150 mL). The organic extracts were dried over sodium sulphate, filtered and concentrated under reduced pressure to obtain crude product. The crude product was purified by preparative TLC (using 5% MeOH/DCM) to give 2-(1-(1H-imidazol-1-yl)propyl)-5-(4-fluorophenyl)-1,3,4-thiadiazole as a brown solid. (10 mg, 8.3% yield). ¹H NMR (400 MHz, DMSO-d₆): δ 8.01 (q, 2H), 7.40 (m, 1H), 7.40-7.35 (m, 3H), 6.98 (s, 1H), 5.96 (q, 1H), 2.42-2.37 (m, 2H); 0.85 (t, 3H). LC-MS m/z calcd for [M+H]+ 289.08. found 289.1.

Example 20

5-(5-(1-(1H-imidazol-1-yl)ethyl)thiophen-2-yl)-1-methylpyridin-2(1H)-one

Step 1: 5-bromo-2-methoxypyridine

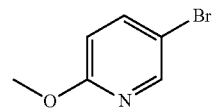

A mixture of 2,5-dibromopyridine (10 g, 42.37 mmol) and NaOMe (6.86 g, 127.1 mmol) in MeOH (100 mL) was heated at 70° C. and refluxed for 10 h. The mixture was allowed to cool to room temperature, was treated with water (100 mL) and extracted with EtOAc (2×150 mL). The combined organic extracts were dried over sodium sulphate and concentrated under reduced pressure to give a pale yellow, volatile oil of 5-bromo-2-methoxypyridine (6.7 g, 84% yield), which was used without purification in the next step. ¹H NMR (400 MHz, CDCl₃): δ 8.19 (s, 1H), 7.62 (dd, 1H), 6.65 (d, 1H), 3.90 (s, 3H); LC-MS m/z calcd for [M+H]+ 189.96. found 190.0.

Step 2: 5-bromopyridin-2(1H)-one

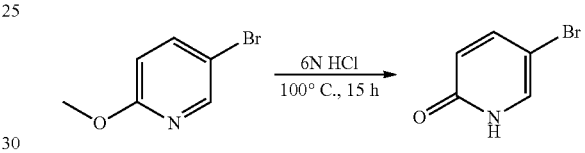

5-Bromo-2-methoxypyridine (6.7 g, 35.8 mmol) was dissolved in 6N HCl (40 mL). The solution was heated at 100° C. for 15 h. The mixture was cooled to 5° C. and the pH of the mixture was adjusted to pH 6.5 with 10% aq. NaOH. The crystalline precipitate was collected by filtration and washed with water (100 mL), and dried under vacuum to give 5-bromopyridin-2(1H)-one (3.0 g, 48% yield). ¹H NMR (400 MHz, DMSO-d₆): δ 11.67 (s, 1H), 7.66 (s, 1H), 3.77 (d, 1H), 6.33 (d, 1H); LC-MS m/z calcd for [M+H]+ 175.95. found 176.0.

Step 3: 5-bromo-1-methylpyridin-2(1H)-one

To a solution of 5-bromopyridin-2(1H)-one (3.0 g, 17.2 mmol) in DMF (30 mL) was added iodomethane (7.34 g, 5.17 mmol) and potassium carbonate (14.24 g, 103.2 mmol) under argon. The reaction mixture was stirred at room temperature for 16 h, and was then concentrated under vacuum. The residue was dissolved in ethyl acetate (2×100 mL) and then washed with water (2×50 mL) and brine solution (2×50 mL). The organic phase was dried over sodium sulphate, concentrated under vacuum to afford 5-bromo-1-methylpyridin-2 (1H)-one as a yellow solid. ¹H NMR (400 MHz, CDCl₃): δ

7.40 (s, 1H), 7.34 (d, 1H), 7.25 (s, 1H), 6.48 (d, 1H), 3.51 (s, 3H); LC-MS m/z calcd for [M+H]+ 189.96. found 190.0.

Step 4: 5-(5-acetylthiophen-2-yl)-1-methylpyridin-2(1H)-one

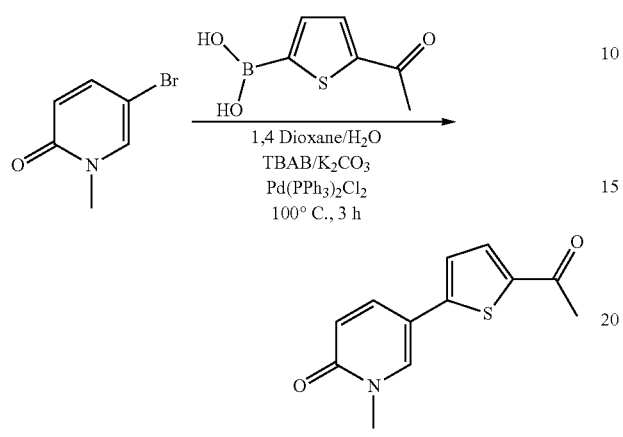

To a solution of 5-bromo-1-methylpyridin-2(1H)-one (1.0 g, 5.31 mmol) in 1,4-dioxane (10 mL)\H₂O (5 mL) was added 5-acetylthiophen-2-yl boronic acid (1.35 g, 7.97 mmol), tetra-butyl ammonium bromide (17 mg, 0.053 mmol), K₂CO₃ (2.19 g, 15.93 mmol) and Pd(PPh₃)₂Cl₂ (37 mg, 0.053 mmol) under argon. The mixture was degassed and heated to 100° C. for 3 h. After the reaction was complete based on monitoring by TLC (80% EtOAc\hexane), the mixture was filtered with Celite® reagent and the filtrate was separated. This filtrate was concentrated and extracted with EtOAc (2×100 mL), washed with water (100 mL), and brine solution (100 mL). The organic layer was dried over sodium sulphate and concentrated in vacuum. The residue was purified by Combi-flash® column purifier (80% ethyl acetate in hexane) to provide 5-(5-acetylthiophen-2-yl)-1-methylpyridin-2(1H)-one as a yellow viscous liquid (0.65 g, 43% yield). ¹H NMR (400 MHz, DMSO-d₆): δ 8.31 (d, 1H), 7.88 (d, 1H), 7.80 (dd, 1H), 7.41 (d, 1H), 6.46 (d, 1H), 3.48 (s, 3H), 2.48 (s, 3H); LC-MS m/z calcd for [M+H]+ 234.05. found 234.1.

Step 5: 5-(5-(1-hydroxyethyl)thiophen-2-yl)-1-methylpyridin-2(1H)-one

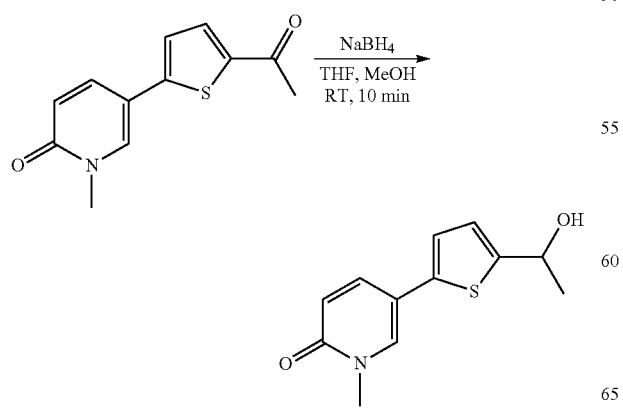

To a solution of 5-(5-acetylthiophen-2-yl)-1-methylpyridin-2(1H)-one (0.65 g, 2.78 mmol) in THF (8 mL) and MeOH (8 mL) was added NaBH₄ (0.26 g, 6.97 mmol) under nitrogen. The mixture was stirred at rt for 10 min, quenched with ammonium chloride solution (15 mL) and extracted with ethyl acetate (2×100 mL). The organic extracts were washed with brine solution (2×50 mL), dried over sodium sulphate and evaporated to obtain the crude compound. Purification by flash chromatography (100-200μ; 100% ethyl acetate) afforded 5-(5-(1-hydroxyethyl)thiophen-2-yl)-1-methylpyridin-2(1H)-one (0.5 g, 76% yield). ¹H NMR (400 MHz, DMSO-d₆): δ 8.00 (s, 1H), 7.69 (d, 1H), 7.07 (d, 1H), 6.83 (d, 1H), 6.43 (d, 1H), 5.51 (bs, 1H), 4.88 (q, 1H), 3.45 (s, 3H), 1.38 (d, 3H); LC-MS m/z calcd for [M+H]+ 236.07 found 236.3.

Step 6: 5-(5-(1-(1H-imidazol-1-yl)ethyl)thiophen-2-yl)-1-methylpyridin-2(1H)-one

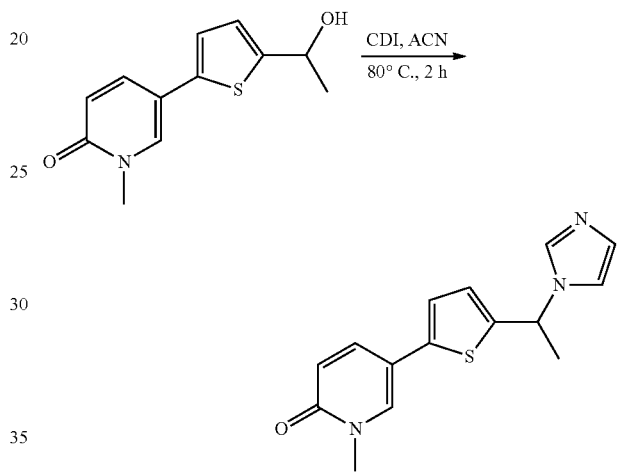

To a solution of 5-(5-(1-hydroxyethyl)thiophen-2-yl)-1-methylpyridin-2(1H)-one (0.3 g, 1.27 mmol) in acetonitrile (10 mL) was added CDI (2.07 g, 3.35 mmol) under nitrogen and the mixture was heated to 80° C. for 2 h. The contents were cooled to rt, diluted with ethyl acetate (100 mL), washed with ice-cold water (2×100 mL), brine solution (2×50 mL), the layers separate, the organic layer dried over sodium sulphate and distilled off to provide the crude product. The product was purified by flash column (100-200μ; 7% methanol in dichloromethane) to give 5-(5-(1-(1H-imidazol-1-yl)ethyl)thiophen-2-yl)-1-methylpyridin-2(1H)-one (0.16 g, 43% yield). ¹H NMR (400 MHz, DMSO-d₆): δ 8.00 (s, 1H), 7.77 (s, 1H), 7.66 (d, 1H), 7.23 (s, 1H), 7.13 (d, 1H), 7.00 (d, 1H), 6.92 (d, 1H), 6.41 (d, 1H), 5.77 (q, 1H), 3.43 (s, 3H), 1.82 (d, 3H); LC-MS m/z calcd for [M+H]+ 286.09. found 218.3 [M-imidazole]+.

Example 21

5-(5-(1-(1H-imidazol-1-yl)ethyl)thiophen-2-yl)-1-isopropylpyridin-2(1H)-one

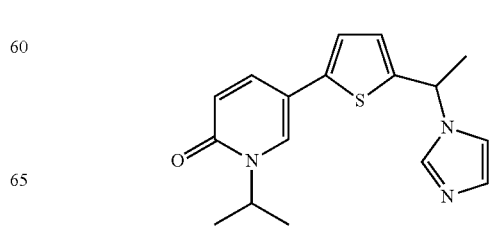

Step 1: 5-iodo-1-isopropylpyridin-2(1H)-one

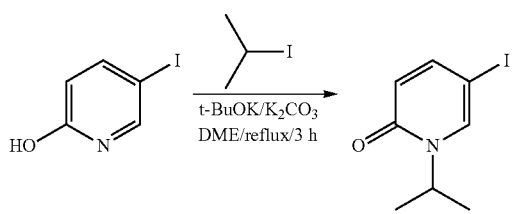

To a stirred solution 5-iodopyridin-2-ol (0.4 g, 1.80 mmol) in DME (10 mL) was added t-BuOK (0.604 g, 5.4 mmol). The mixture was stirred for 30 min at rt, K₂CO₃ (0.621 g, 4.5 mmol) and 2-iodopropane (0.35 mL, 3.6 mmol) were added, and the reaction was heated at reflux for about 3 h. The reaction mixture was diluted with water (30 mL) and extracted with ethyl acetate (2×100 mL). The combined organic extracts were washed with brine solution (10 mL), dried over Na₂SO₄ and concentrated under vacuum to obtain crude product. The crude product was purified by flash chromatography (silica gel, 60-120μ) using 10% ethyl acetate in hexane as eluent to afford 5-iodo-1-isopropylpyridin-2(1H)-one as an off-white solid (0.41 g, 67% yield). $^1$H NMR (400 MHz, DMSO-$d_6$): δ 7.90 (s, 1H), 7.49 (dd, 1H), 6.21 (d, 1H), 4.94 (t, 1H), 1.25 (t, 6H), LC-MS m/z calcd for [M+H]⁺ 263.98. found 264.0.

Step 2: 5-(1-isopropyl-6-oxo-1,6-dihydropyridin-3-yl)thiophene-2-carbaldehyde

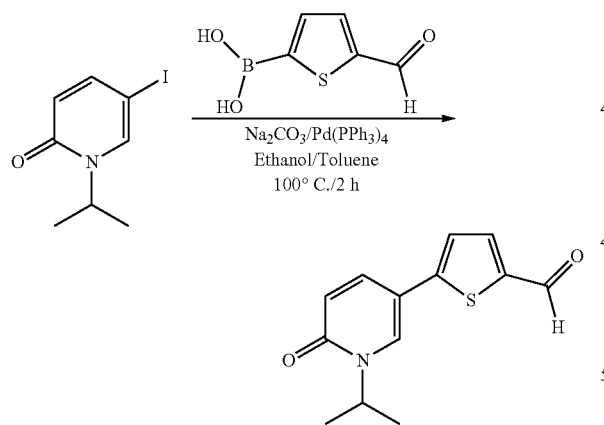

To a stirred solution of 5-iodo-1-isopropylpyridin-2(1H)-one (0.41 g, 1.55 mmol) in toluene (5 mL) and ethanol (2 mL) was added 5-formylthiophen-2-yl boronic acid (0.289 g, 1.87 mmol), 2M Na₂CO₃ (0.495 g, 4.67 mmol), and Pd(PPh₃)₄ (0.09 g, 0.07 mmol). The mixture was purged with argon and heated at 100° C. for about 2 h. The mixture was concentrated, diluted with water (50 mL), and extracted with ethyl acetate (2×200 mL). The combined organic extracts were washed with brine solution (20 mL), dried over Na₂SO₄ and concentrated under vacuum to obtain crude product. The crude product was purified by flash chromatography (silica gel, 60-120μ) using 20% ethyl acetate in hexane as eluent to afford 5-(1-isopropyl-6-oxo-1,6-dihydropyridin-3-yl) thiophene-2-carbaldehyde as an off-white solid (0.205 g, 53.3% yield). $^1$H NMR (400 MHz, DMSO-$d_6$): δ 8.18 (s, 1H), 7.99 (d, 1H), 7.78 (d, 1H), 7.62 (d, 1H), 7.58 (d, 1H), 7.53 (d, 1H), 5.08-5.01 (m, 1H), 1.21 (t, 6H), LC-MS m/z calcd for [M+H]⁺ 248.07. found 248.1.

Step 3: 5-(5-(1-hydroxyethyl)thiophen-2-yl)-1-isopropylpyridin-2(1H)-one

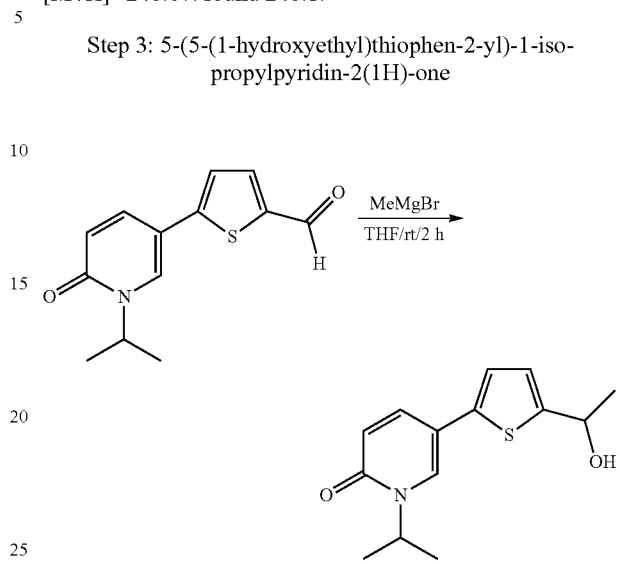

A solution of 5-(1-isopropyl-6-oxo-1,6-dihydropyridin-3-yl)thiophene-2-carbaldehyde (0.205 g, 0.829 mmol) in THF (10 mL) was cooled to 0° C. A solution of 1.5M methyl magnesium bromide in diethyl ether (1.65 mL, 2.48 mmol) was added slowly at 0° C. and the mixture was stirred for 2 h at rt. The reaction mixture was quenched with saturated NH₄Cl solution (10 mL) and extracted with ethyl acetate (2×100 mL). The combined organic extracts were washed with brine solution (10 mL), dried over Na₂SO₄ and concentrated under vacuum to obtain crude 5-(5-(1-hydroxyethyl)thiophen-2-yl)-1-isopropylpyridin-2(1H)-one as an off-white solid (0.150 g, 71% yield). LC-MS m/z calcd for [M+H]⁺ 264.1. found 264.1.

Step 4: 5-(5-(1-(1H-imidazol-1-yl)ethyl)thiophen-2-yl)-1-isopropylpyridin-2(1H)-one

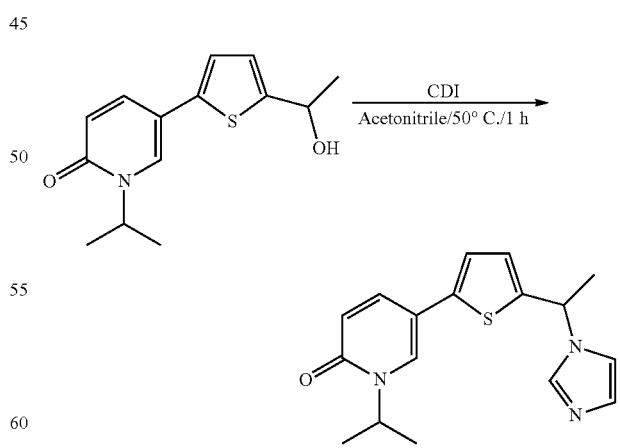

To a stirred solution of 5-(5-(1-hydroxyethyl)thiophen-2-yl)-1-isopropylpyridin-2(1H)-one (0.075 g, 0.28 mmol) in ACN (5 mL) was added 1,1-carbonyl diimidazole (0.240 g, 1.48 mmol). The mixture was heated at 50° C. for about 1 h. The mixture was concentrated, diluted with water (25 mL), and extracted with ethyl acetate (2×100 mL). The combined organic extracts were washed with brine solution (10 mL), dried over $Na_2SO_4$ and concentrated under vacuum to obtain crude product. The crude product was purified by preparative TLC using 2% methanol in DCM as eluent to afford 5-(5-(1-(1H-imidazol-1-yl)ethyl)thiophen-2-yl)-1-isopropylpyridin-2(1H)-one as an off-white solid (0.016 g, 13.4% yield). $^1$H NMR (400 MHz, DMSO-$d_6$): δ 7.83 (s, 1H), 7.77 (s, 1H), 7.60 (dd, 1H), 7.24 (s, 1H), 7.20 (d, 1H), 7.03 (d, 1H), 6.89 (s, 1H), 6.42 (d, 1H), 5.80-5.75 (m, 1H), 5.05-4.98 (m, 1H), 1.82 (d, 3H), 1.31 (d, 6H), LC-MS m/z calcd for [M+H]$^+$ 314.12. found 314.1.

The following Table 1 summarizes the compounds and synthetic methods utilized to prepare the name compounds of Examples 1-21. This table also provides additional compounds as Examples 22-66 and the synthetic route by which the same were prepared.

TABLE 1

| Ex. | Structure | Name | Synthesis method (scheme #) |
|---|---|---|---|
| 1 | [structure] | 2-(3-Fluoro-phenyl)-5-(1-imidazol-1-yl-propyl)-thiazole | 1 |
| 2 | [structure] | 5-(1-Imidazol-1-yl-propyl)-2-(1-methyl-1H-pyrazol-4-yl)-thiazole | 1 |
| 3 | [structure] | 1-{1-[5-(4-Methoxy-phenyl)-thiophen-2-yl]-propyl}-1H-imidazole | 1 |
| 4 | [structure] | 4-[5-(1-Imidazol-1-yl-propyl)-thiophen-2-yl]-phenol | 1 |
| 5 | [structure] | 4-[6-(1-Imidazol-1-yl-propyl)-pyridin-3-yl]-benzoic acid ethyl ester | 1 |

TABLE 1-continued
| Ex. | Structure | Name | Synthesis method (scheme #) |
|---|---|---|---|
| 6 | 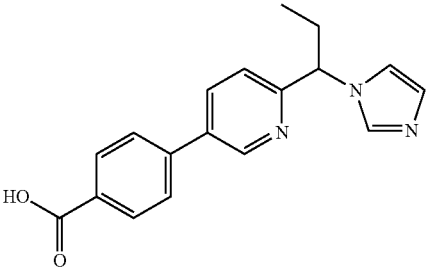 [SMILES: CCC(c1ccc(-c2ccc(C(=O)O)cc2)cn1)n1ccnc1] | 4-[6-(1-Imidazol-1-yl-propyl)-pyridin-3-yl]-benzoic acid | 1 |
| 7 | 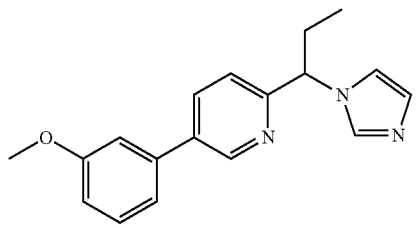 [SMILES: CCC(c1ccc(-c2cccc(OC)c2)cn1)n1ccnc1] | 2-(1-Imidazol-1-yl-propyl)-5-(3-methoxy-phenyl)-pyridine | 2 |
| 8 | 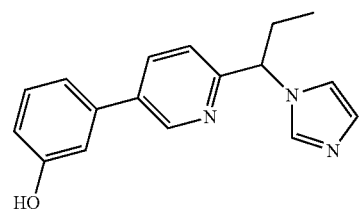 [SMILES: CCC(c1ccc(-c2cccc(O)c2)cn1)n1ccnc1] | 3-[6-(1-Imidazol-1-yl-propyl)-pyridin-3-yl]-phenol | 2 |
| 9 | 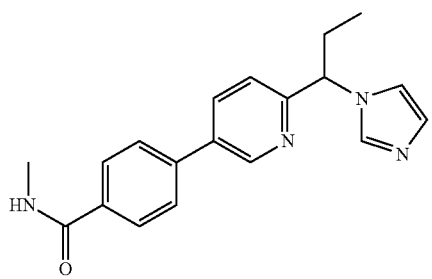 [SMILES: CCC(c1ccc(-c2ccc(C(=O)NC)cc2)cn1)n1ccnc1] | 4-[6-(1-Imidazol-1-yl-propyl)-pyridin-3-yl]-N-methyl-benzamide | 2 |
| 10 | 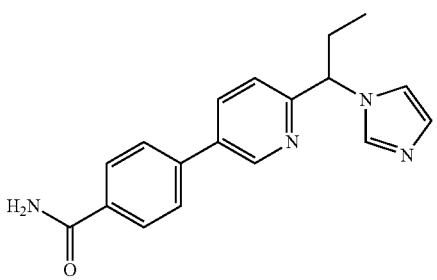 [SMILES: CCC(c1ccc(-c2ccc(C(N)=O)cc2)cn1)n1ccnc1] | 4-[6-(1-Imidazol-1-yl-propyl)-pyridin-3-yl]-benzamide | 2 |
| 11 | 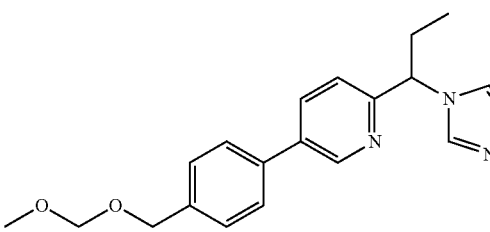 | 2-(1-Imidazol-1-yl-propyl)-5-(4-methoxymethoxy-methyl-phenyl)pyridine | 2 |

TABLE 1-continued

| Ex. | Structure | Name | Synthesis method (scheme #) |
|---|---|---|---|
| 12 | 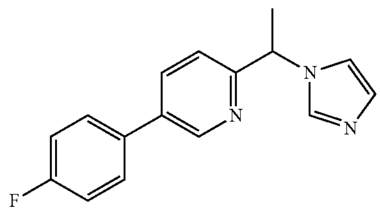 [SMILES: CC(c1ccc(-c2ccc(F)cc2)cn1)n1ccnc1] | 5-(4-Fluoro-phenyl)-2-(1-imidazol-1-yl-ethyl)-pyridine | 3 |
| 13 | 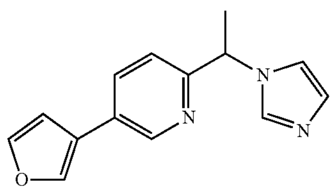 [SMILES: CC(c1ccc(-c2ccoc2)cn1)n1ccnc1] | 2-[1-(2,3-Dihydro-imidazol-1-yl)-ethyl]-5-furan-3-yl-pyridine | 4 |
| 14 | 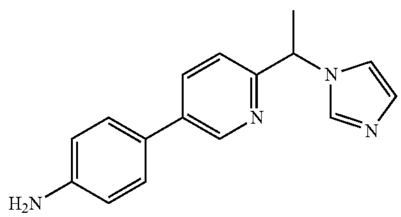 [SMILES: CC(c1ccc(-c2ccc(N)cc2)cn1)n1ccnc1] | 4-[6-(1-Imidazol-1-yl-ethyl)-pyridin-3-yl]-phenylamine | 4 |
| 15 | 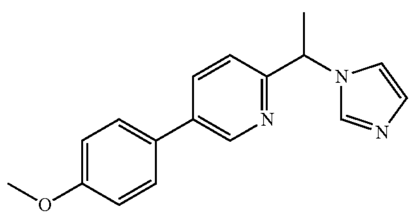 [SMILES: COc1ccc(-c2ccc(C(C)n3ccnc3)nc2)cc1] | 2-(1-Imidazol-1-yl-ethyl)-5-(4-methoxy-phenyl)-pyridine | 4 |
| 16 | 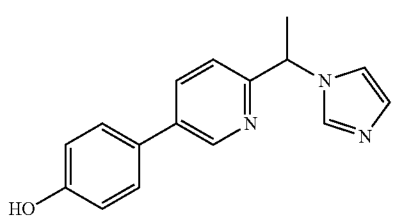 [SMILES: CC(c1ccc(-c2ccc(O)cc2)cn1)n1ccnc1] | 4-[6-(1-Imidazol-1-yl-ethyl)-pyridin-3-yl]-phenol | 4 |
| 17 | 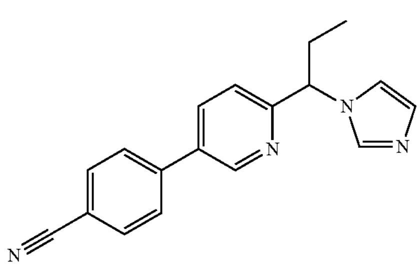 [SMILES: CCC(c1ccc(-c2ccc(C#N)cc2)cn1)n1ccnc1] | 4-[6-(1-Imidazol-1-yl-propyl)-pyridin-3-yl]-benzonitrile | 5 |

TABLE 1-continued

| Ex. | Structure | Name | Synthesis method (scheme #) |
|---|---|---|---|
| 18 | 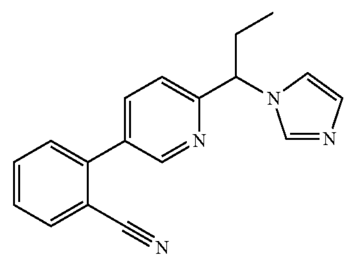 [SMILES: CCC(c1ccc(-c2ccccc2C#N)cn1)n1ccnc1] | 2-[6-(1-Imidazol-1-yl-propyl)-pyridin-3-yl]-benzonitrile | 5 |
| 19 | 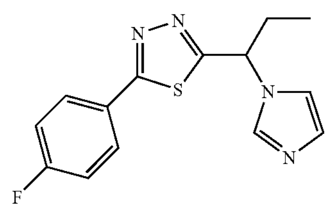 [SMILES: CCC(c1nnc(-c2ccc(F)cc2)s1)n1ccnc1] | 2-(4-Fluoro-phenyl)-5-(1-imidazol-1-yl-propyl)-[1,3,4]thiadiazole | 6 |
| 20 | 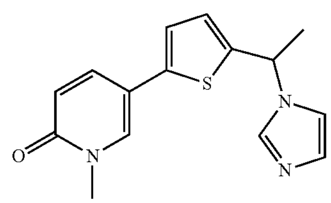 [SMILES: CC(c1ccc(-c2ccc(=O)n(C)c2)s1)n1ccnc1] | 5-[5-(1-Imidazol-1-yl-ethyl)-thiophen-2-yl]-1-methyl-1H-pyridin-2-one | 7 |
| 21 | 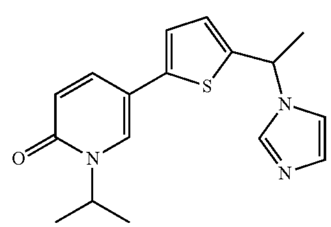 [SMILES: CC(c1ccc(-c2ccc(=O)n(C(C)C)c2)s1)n1ccnc1] | 5-[5-(1-Imidazol-1-yl-ethyl)-thiophen-2-yl]-1-isopropyl-1H-pyridin-2-one | 7 |
| 22 | 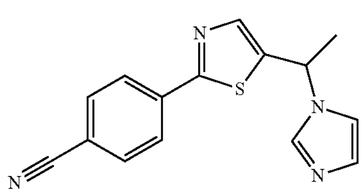 [SMILES: CC(c1cnc(-c2ccc(C#N)cc2)s1)n1ccnc1] | 4-(5-(1-(1H-imidazol-1-yl)ethyl)thiazol-2-yl)benzonitrile | 1 |
| 23 | 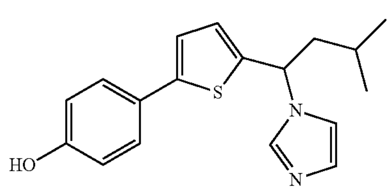 [SMILES: CC(C)CC(c1ccc(-c2ccc(O)cc2)s1)n1ccnc1] | 4-(5-(1-(1H-imidazol-1-yl)-3-methylbutyl)-thiophen-2-yl)phenol | 1 |
| 24 | 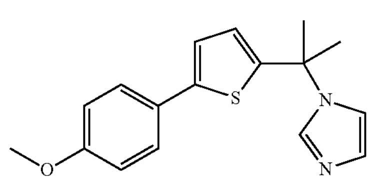 [SMILES: COc1ccc(-c2ccc(C(C)(C)n3ccnc3)s2)cc1] | 1-(2-(5-(4-methoxyphenyl)-thiophen-2-yl)-propan-2-yl)-1H-imidazole | 1 |

TABLE 1-continued

| Ex. | Structure | Name | Synthesis method (scheme #) |
|---|---|---|---|
| 25 | 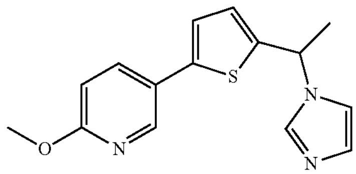 [SMILES: COc1ccc(-c2ccc(C(C)n3ccnc3)s2)cn1] | 5-[5-(1-Imidazol-1-yl-ethyl)-thiophen-2-yl]-2-methoxy-pyridine | 1 |
| 26 | 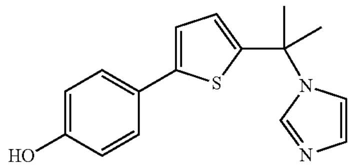 [SMILES: CC(C)(c1ccc(-c2ccc(O)cc2)s1)n1ccnc1] | 4-[5-(1-Imidazol-1-yl-1-methyl-ethyl)-thiophen-2-yl]-phenol | 1 |
| 27 | 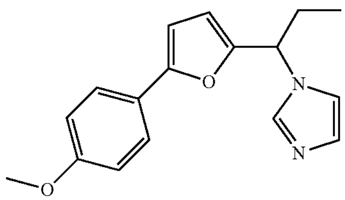 [SMILES: CCC(c1ccc(-c2ccc(OC)cc2)o1)n1ccnc1] | 1-{1-[5-(4-Methoxy-phenyl)-furan-2-yl]-propyl}-1H-imidazole | 1 |
| 28 | 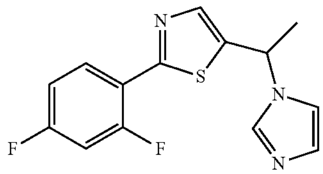 [SMILES: CC(c1cnc(-c2ccc(F)cc2F)s1)n1ccnc1] | 2-(2,4-Difluoro-phenyl)-5-(1-imidazol-1-yl-ethyl)-thiazole | 1 |
| 29 | 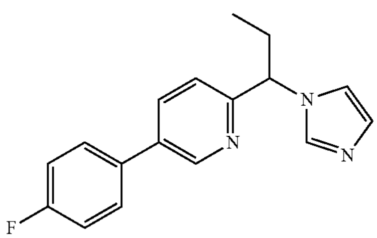 [SMILES: CCC(c1ccc(-c2ccc(F)cc2)cn1)n1ccnc1] | 5-(4-Fluoro-phenyl)-2-(1-imidazol-1-yl-propyl)-pyridine | 1 |
| 30 | 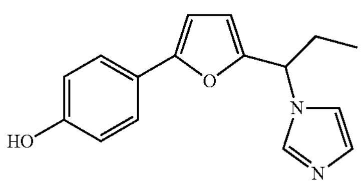 [SMILES: CCC(c1ccc(-c2ccc(O)cc2)o1)n1ccnc1] | 4-[5-(1-Imidazol-1-yl-propyl)-furan-2-yl]-phenol | 1 |
| 31 | 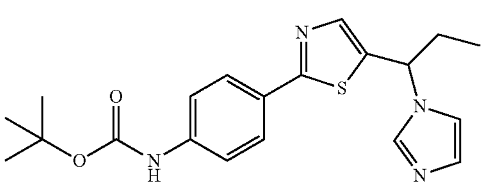 [SMILES: CCC(c1cnc(-c2ccc(NC(=O)OC(C)(C)C)cc2)s1)n1ccnc1] | {4-[5-(1-Imidazol-1-yl-propyl)-thiazol-2-yl]-phenyl}-carbamic acid tert-butyl ester | 1 |
| 32 | 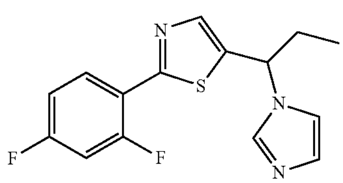 [SMILES: CCC(c1cnc(-c2ccc(F)cc2F)s1)n1ccnc1] | 2-(2,4-Difluoro-phenyl)-5-(1-imidazol-1-yl-propyl)-thiazole | 1 |

TABLE 1-continued

| Ex. | Structure | Name | Synthesis method (scheme #) |
|---|---|---|---|
| 33 | 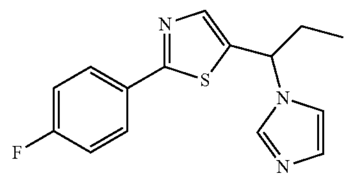 [SMILES: CCC(c1cnc(-c2ccc(F)cc2)s1)n1ccnc1] | 2-(4-Fluoro-phenyl)-5-(1-imidazol-1-yl-propyl)-thiazole | 1 |
| 34 | 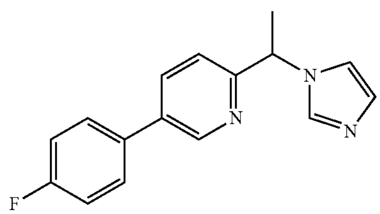 [SMILES: CC(c1ccc(-c2ccc(F)cc2)cn1)n1ccnc1] | 5-(4-Fluoro-phenyl)-2-(1-imidazol-1-yl-ethyl)-pyridine | 1 |
| 35 | 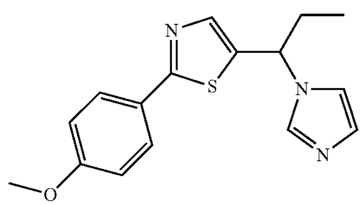 [SMILES: CCC(c1cnc(-c2ccc(OC)cc2)s1)n1ccnc1] | 5-(1-Imidazol-1-yl-propyl)-2-(4-methoxy-phenyl)-thiazole | 1 |
| 36 | 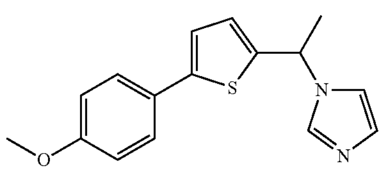 [SMILES: COc1ccc(-c2ccc(C(C)n3ccnc3)s2)cc1] | 1-{1-[5-(4-Methoxy-phenyl)-thiophen-2-yl]-ethyl}-1H-imidazole | 3 |
| 37 | 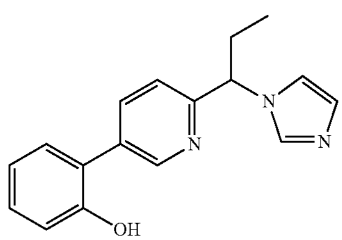 [SMILES: CCC(c1ccc(-c2ccccc2O)cn1)n1ccnc1] | 2-[6-(1-Imidazol-1-yl-propyl)-pyridin-3-yl]-phenol | 2 |
| 38 | 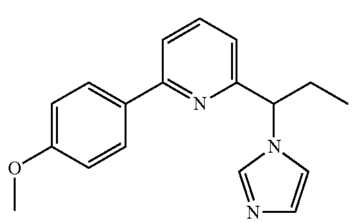 [SMILES: CCC(c1cccc(-c2ccc(OC)cc2)n1)n1ccnc1] | 2-(1-Imidazol-1-yl-propyl)-6-(4-methoxy-phenyl) pyridine | 2 |
| 39 | 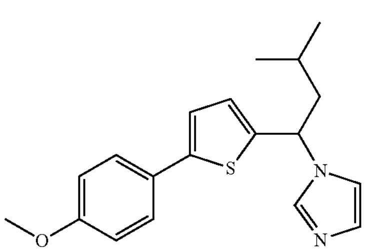 [SMILES: COc1ccc(-c2ccc(C(CC(C)C)n3ccnc3)s2)cc1] | 1-{1-[5-(4-Methoxy-phenyl)-thiophen-2-yl]-3-methyl-butyl}-1H-imidazole | 1 |

TABLE 1-continued

| Ex. | Structure | Name | Synthesis method (scheme #) |
|---|---|---|---|
| 40 | 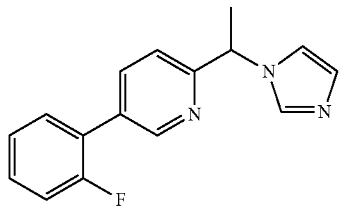 [SMILES: CC(c1ccc(-c2ccccc2F)cn1)n1ccnc1] | 5-(2-Fluoro-phenyl)-2-(1-imidazol-1-yl-ethyl)-pyridine | 1 |
| 41 | 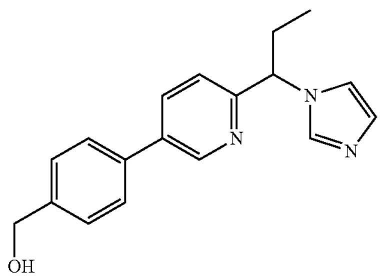 [SMILES: CCC(c1ccc(-c2ccc(CO)cc2)cn1)n1ccnc1] | {4-[6-(1-Imidazol-1-yl-propyl)-pyridin-3-yl]-phenyl}-methanol | 2 |
| 42 | 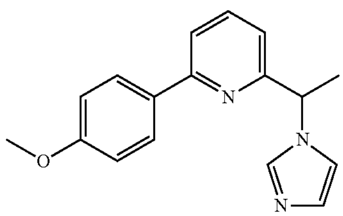 [SMILES: COc1ccc(-c2cccc(C(C)n3ccnc3)n2)cc1] | 2-(1-Imidazol-1-yl-ethyl)-6-(4-methoxy-phenyl)-pyridine | 2 |
| 43 | 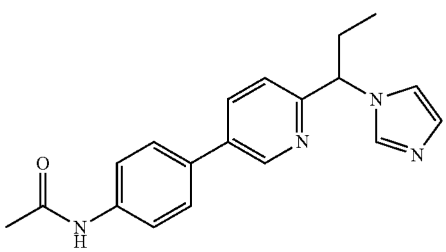 [SMILES: CCC(c1ccc(-c2ccc(NC(C)=O)cc2)cn1)n1ccnc1] | N-{4-[6-(1-Imidazol-1-yl-propyl)-pyridin-3-yl]-phenyl}-acetamide | 2 |
| 44 | 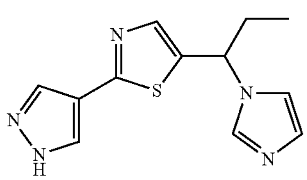 [SMILES: CCC(c1cnc(-c2cn[nH]c2)s1)n1ccnc1] | 5-(1-Imidazol-1-yl-propyl)-2-(1H-pyrazol-4-yl)-thiazole | 1 |
| 45 | 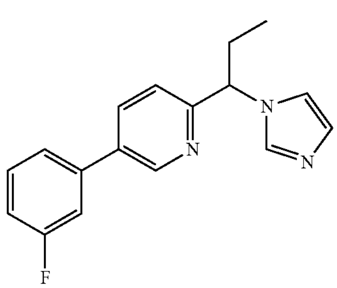 [SMILES: CCC(c1ccc(-c2cccc(F)c2)cn1)n1ccnc1] | 5-(3-Fluoro-phenyl)-2-(1-imidazol-1-yl-propyl)-pyridine | 1 |

TABLE 1-continued

| Ex. | Structure | Name | Synthesis method (scheme #) |
|---|---|---|---|
| 46 | 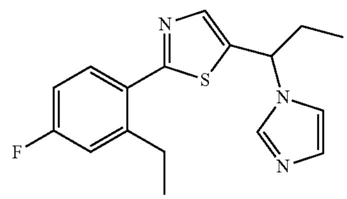 [SMILES: CCc1cc(F)ccc1-c1ncc(C(CC)n2ccnc2)s1] | 2-(2-Ethyl-4-fluoro-phenyl)-5-(1-imidazol-1-yl-propyl)-thiazole | 1 |
| 47 | 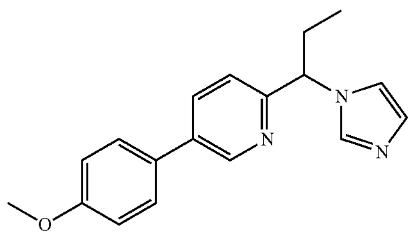 [SMILES: CCC(c1ccc(-c2ccc(OC)cc2)cn1)n1ccnc1] | 2-(1-Imidazol-1-yl-propyl)-5-(4-methoxy-phenyl)-pyridine | 2 |
| 48 | 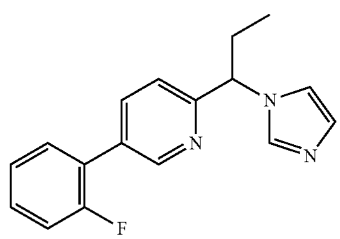 [SMILES: CCC(c1ccc(-c2ccccc2F)cn1)n1ccnc1] | 5-(2-Fluoro-phenyl)-2-(1-imidazol-1-yl-propyl)-pyridine | 1 |
| 49 | 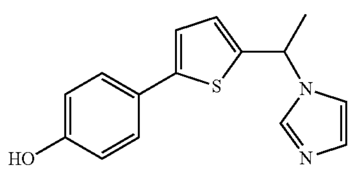 [SMILES: CC(c1ccc(-c2ccc(O)cc2)s1)n1ccnc1] | 4-[5-(1-Imidazol-1-yl-ethyl)-thiophen-2-yl]-phenol | 3 |
| 50 | 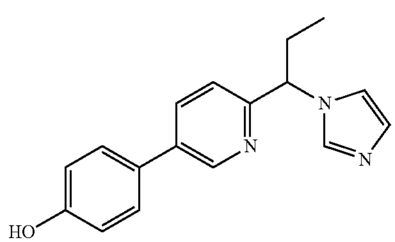 [SMILES: CCC(c1ccc(-c2ccc(O)cc2)cn1)n1ccnc1] | 4-[6-(1-Imidazol-1-yl-propyl)-pyridin-3-yl]-phenol | 1 |
| 51 | 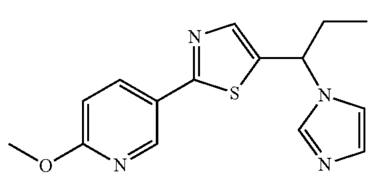 [SMILES: CCC(c1cnc(-c2ccc(OC)nc2)s1)n1ccnc1] | 5-[5-(1-Imidazol-1-yl-propyl)-thiazol-2-yl]-2-methoxy-pyridine | 1 |
| 52 | 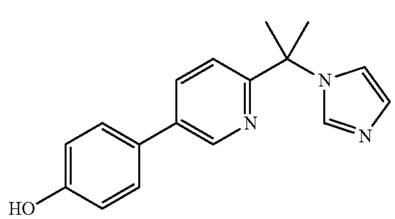 [SMILES: CC(C)(c1ccc(-c2ccc(O)cc2)cn1)n1ccnc1] | 4-[6-(1-Imidazol-1-yl-1-methyl-ethyl)-pyridin-3-yl]-phenol | 1 |

TABLE 1-continued

| Ex. | Structure | Name | Synthesis method (scheme #) |
|---|---|---|---|
| 53 | 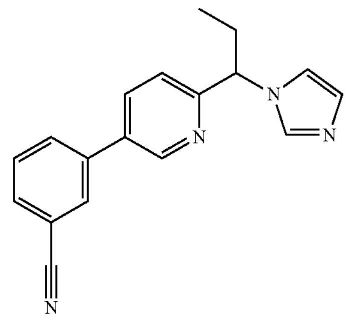 [SMILES: CCC(c1ccc(-c2cccc(C#N)c2)cn1)n1ccnc1] | 3-[6-(1-Imidazol-1-yl-propyl)-pyridin-3-yl]-benzonitrile | 5 |
| 54 | 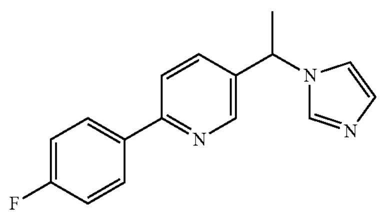 [SMILES: CC(c1ccc(-c2ccc(F)cc2)nc1)n1ccnc1] | 2-(4-Fluoro-phenyl)-5-(1-imidazol-1-yl-ethyl)-pyridine | 1 |
| 55 | 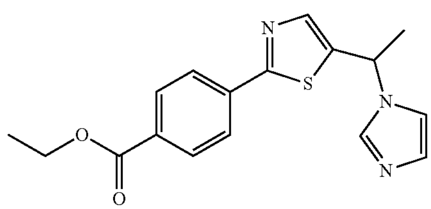 [SMILES: CCOC(=O)c1ccc(-c2ncc(C(C)n3ccnc3)s2)cc1] | 4-[5-(1-Imidazol-1-yl-ethyl)-thiazol-2-yl]-benzoic acid ethyl ester | 1 |
| 56 | 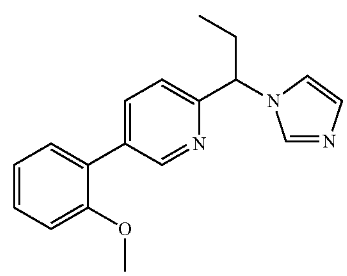 [SMILES: CCC(c1ccc(-c2ccccc2OC)cn1)n1ccnc1] | 2-(1-Imidazol-1-yl-propyl)-5-(2-methoxy-phenyl)-pyridine | 2 |
| 57 | 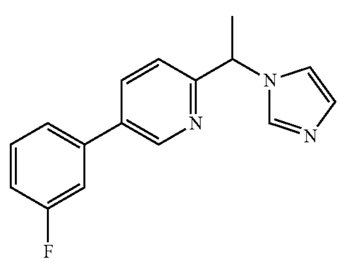 [SMILES: CC(c1ccc(-c2cccc(F)c2)cn1)n1ccnc1] | 5-(3-Fluoro-phenyl)-2-(1-imidazol-1-yl-ethyl)-pyridine | 1 |
| 58 | 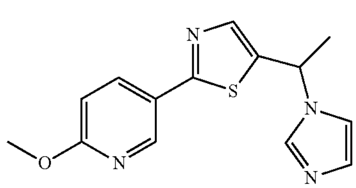 [SMILES: COc1ccc(-c2ncc(C(C)n3ccnc3)s2)cn1] | 5-[5-(1-Imidazol-1-yl-ethyl)-thiazol-2-yl]-2-methoxy-pyridine | 1 |

TABLE 1-continued

| Ex. | Structure | Name | Synthesis method (scheme #) |
|---|---|---|---|
| 59 | 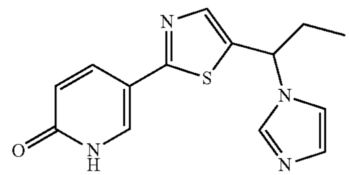 [SMILES: CCC(c1cnc(-c2ccc(=O)[nH]c2)s1)n1ccnc1] | 5-[5-(1-Imidazol-1-yl-propyl)-thiazol-2-yl]-1H-pyridin-2-one | 1 |
| 60 | 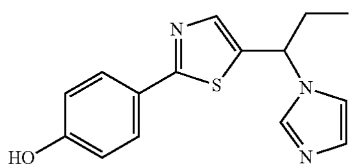 [SMILES: CCC(c1cnc(-c2ccc(O)cc2)s1)n1ccnc1] | 4-[5-(1-Imidazol-1-yl-propyl)-thiazol-2-yl]-phenol | 1 |
| 61 | 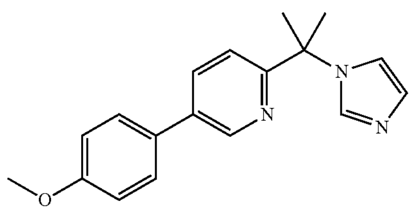 [SMILES: COc1ccc(-c2ccc(C(C)(C)n3ccnc3)nc2)cc1] | 2-(1-Imidazol-1-yl-1-methyl-ethyl)-5-(4-methoxy-phenyl)-pyridine | 1 |
| 62 | 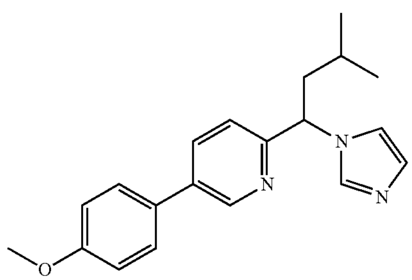 [SMILES: COc1ccc(-c2ccc(C(CC(C)C)n3ccnc3)nc2)cc1] | 2-(1-Imidazol-1-yl-3-methyl-butyl)-5-(4-methoxy-phenyl)-pyridine | 1 |
| 63 | 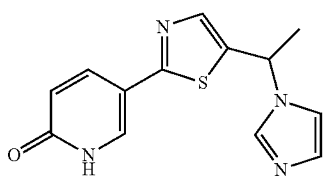 [SMILES: CC(c1cnc(-c2ccc(=O)[nH]c2)s1)n1ccnc1] | 5-[5-(1-Imidazol-1-yl-ethyl)-thiazol-2-yl]-1H-pyridin-2-one | 1 |
| 64 | 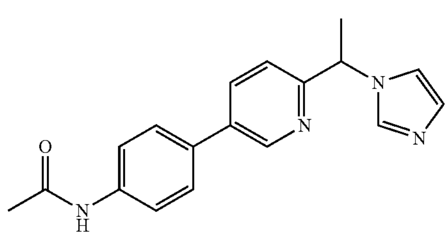 [SMILES: CC(=O)Nc1ccc(-c2ccc(C(C)n3ccnc3)nc2)cc1] | N-{4-[6-(1-Imidazol-1-yl-ethyl)-pyridin-3-yl]-phenyl}-acetamide | 4 |
| 65 | 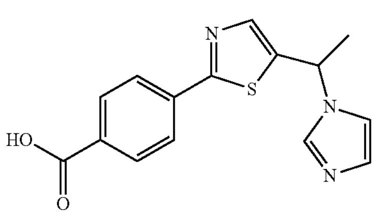 [SMILES: CC(c1cnc(-c2ccc(C(=O)O)cc2)s1)n1ccnc1] | 4-[5-(1-Imidazol-1-yl-ethyl)-thiazol-2-yl]-benzoic acid | 1 |

TABLE 1-continued

| Ex. | Structure | Name | Synthesis method (scheme #) |
|---|---|---|---|
| 66 | 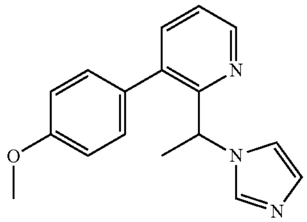 [SMILES: COc1ccc(-c2cccnc2C(C)n2ccnc2)cc1] | 2-(1-(1H-imidazol-1-yl)ethyl)-3-(4-methoxyphenyl)-pyridine | 1 |

The following Table 2 is a summary of the LC-MS data for the compounds prepared according to Examples 1-66.

TABLE 2

| Ex. | Structure | Name | Exact mass | LC-MS [M + H]+ (m/z) | LC-MS retention time (min) |
|---|---|---|---|---|---|
| 1 | 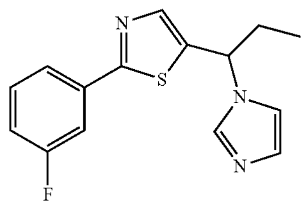 [SMILES: CCC(c1cnc(-c2cccc(F)c2)s1)n1ccnc1] | 2-(3-Fluoro-phenyl)-5-(1-imidazol-1-yl-propyl)-thiazole | 287.09 | 288.0 | 1.40 |
| 2 | 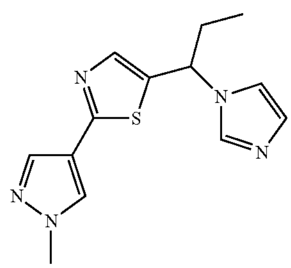 [SMILES: CCC(c1cnc(-c2cnn(C)c2)s1)n1ccnc1] | 5-(1-Imidazol-1-yl-propyl)-2-(1-methyl-1H-pyrazol-4-yl)-thiazole | 273.10 | 274.1 | 0.39 |
| 3 | 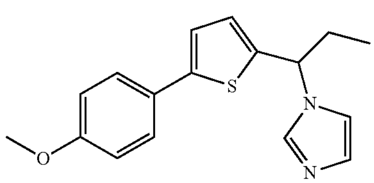 [SMILES: CCC(c1ccc(-c2ccc(OC)cc2)s1)n1ccnc1] | 1-{1-[5-(4-Methoxy-phenyl)-thiophen-2-yl]-propyl}-1H-imidazole | 298.11 | 231.3 * | 1.10 |
| 4 | 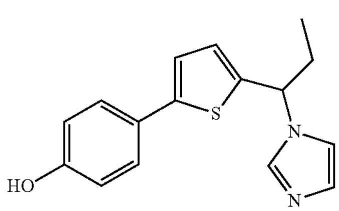 [SMILES: CCC(c1ccc(-c2ccc(O)cc2)s1)n1ccnc1] | 4-[5-(1-Imidazol-1-yl-propyl)-thiophen-2-yl]-phenol | 284.10 | 217.2 * | 1.43 |

TABLE 2-continued
| Ex. | Structure | Name | Exact mass | LC-MS [M + H]+ (m/z) | LC-MS retention time (min) |
|---|---|---|---|---|---|
| 5 | 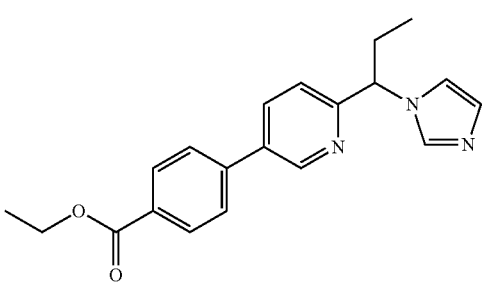 [SMILES: CCOC(=O)c1ccc(-c2ccc(C(CC)n3ccnc3)nc2)cc1] | 4-[6-(1-Imidazol-1-yl-propyl)-pyridin-3-yl]-benzoic acid ethyl ester | 335.16 | 336.2 | 1.08 |
| 6 | 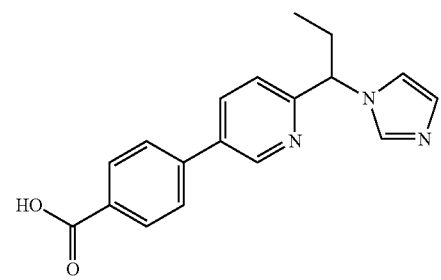 | 4-[6-(1-Imidazol-1-yl-propyl)-pyridin-3-yl]-benzoic acid | 307.13 | 308.1 | 0.93 |
| 7 | 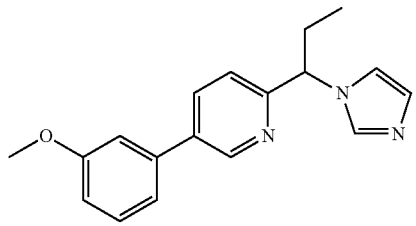 [SMILES: CCC(c1ccc(-c2cccc(OC)c2)cn1)n1ccnc1] | 2-(1-Imidazol-1-yl-propyl)-5-(3-methoxy-phenyl)-pyridine | 293.15 | 294.2 | 1.05 |
| 8 | 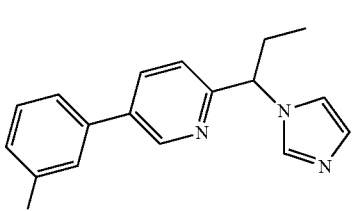 | 3-[6-(1-Imidazol-1-yl-propyl)-pyridin-3-yl]-phenol | 279.14 | 280.0 | 1.19 |
| 9 | 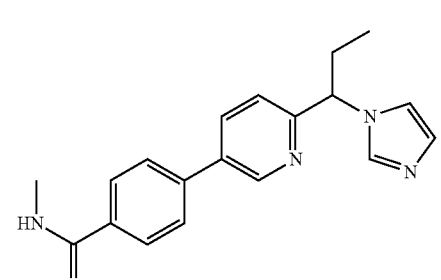 | 4-[6-(1-Imidazol-1-yl-propyl)-pyridin-3-yl]-N-methyl-benzamide | 320.16 | 321.5 | 0.75 |

TABLE 2-continued

| Ex. | Structure | Name | Exact mass | LC-MS [M + H]+ (m/z) | LC-MS retention time (min) |
|---|---|---|---|---|---|
| 10 | 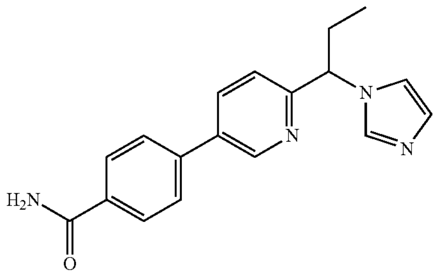 [SMILES: CCC(c1ccc(-c2ccc(C(N)=O)cc2)cn1)n1ccnc1] | 4-[6-(1-Imidazol-1-yl-propyl)-pyridin-3-yl]-benzamide | 306.15 | 307.5 | 0.62 |
| 11 | 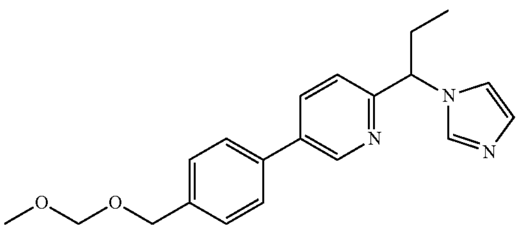 [SMILES: CCC(c1ccc(-c2ccc(COCOC)cc2)cn1)n1ccnc1] | 2-(1-Imidazol-1-yl-propyl)-5-(4-methoxymethoxy-methyl-phenyl)pyridine | 337.18 | 338.2 | 1.47 |
| 12 | 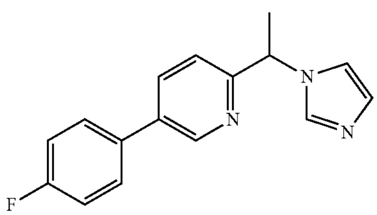 [SMILES: CC(c1ccc(-c2ccc(F)cc2)cn1)n1ccnc1] | 5-(4-Fluoro-phenyl)-2-(1-imidazol-1-yl-ethyl)-pyridine | 267.12 | 268.2 | 0.86 |
| 13 | 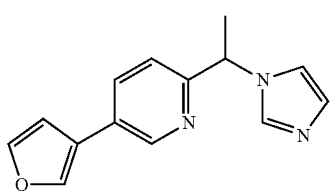 [SMILES: CC(c1ccc(-c2ccoc2)cn1)n1ccnc1] | 2-[1-(2,3-Dihydro-imidazol-1-yl)-ethyl]-5-furan-3-yl-pyridine | 239.11 | 240.4 | 0.84 |
| 14 | 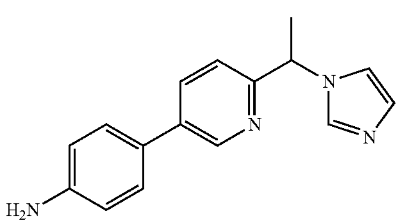 [SMILES: CC(c1ccc(-c2ccc(N)cc2)cn1)n1ccnc1] | 4-[6-(1-Imidazol-1-yl-ethyl)-pyridin-3-yl]-phenylamine | 264.14 | 265.4 | 1.13 |
| 15 | 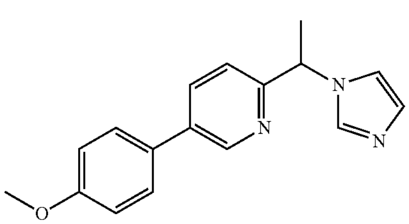 [SMILES: COc1ccc(-c2ccc(C(C)n3ccnc3)nc2)cc1] | 2-(1-Imidazol-1-yl-ethyl)-5-(4-methoxy-phenyl)-pyridine | 279.14 | 280.2 | 2.28 |

TABLE 2-continued

| Ex. | Structure | Name | Exact mass | LC-MS [M + H]+ (m/z) | LC-MS retention time (min) |
|---|---|---|---|---|---|
| 16 | 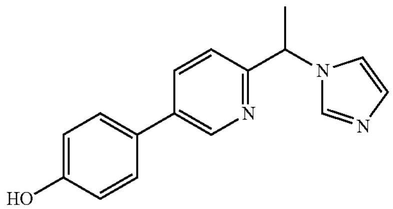 [SMILES: CC(c1ccc(-c2ccc(O)cc2)cn1)n1ccnc1] | 4-[6-(1-Imidazol-1-yl-ethyl)-pyridin-3-yl]-phenol | 265.12 | 266.2 | 2.08 |
| 17 | 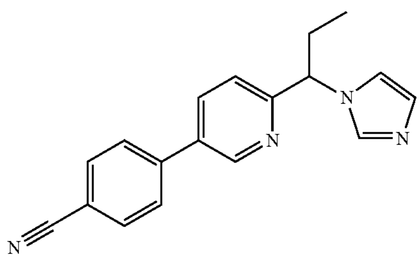 [SMILES: CCC(c1ccc(-c2ccc(C#N)cc2)cn1)n1ccnc1] | 4-[6-(1-Imidazol-1-yl-propyl)-pyridin-3-yl]-benzonitrile | 288.14 | 289.0 | 0.44 |
| 18 | 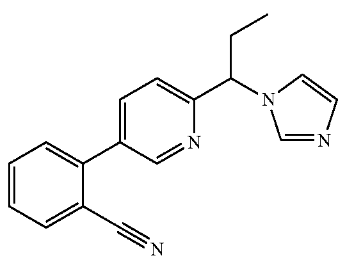 [SMILES: CCC(c1ccc(-c2ccccc2C#N)cn1)n1ccnc1] | 2-[6-(1-Imidazol-1-yl-propyl)-pyridin-3-yl]-benzonitrile | 288.14 | 289.5 | 0.97 |
| 19 | 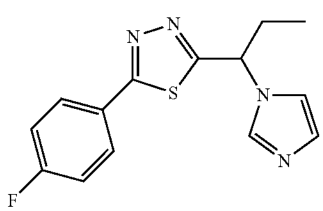 [SMILES: CCC(c1nnc(-c2ccc(F)cc2)s1)n1ccnc1] | 2-(4-Fluoro-phenyl)-5-(1-imidazol-1-yl-propyl)-[1,3,4]thiadiazole | 288.08 | 289.1 | 1.26 |
| 20 | 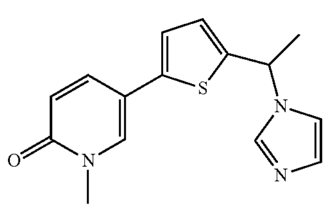 [SMILES: CC(c1ccc(-c2ccc(=O)n(C)c2)s1)n1ccnc1] | 5-[5-(1-Imidazol-1-yl-ethyl)-thiophen-2-yl]-1-methyl-1H-pyridin-2-one | 285.09 | 218.3 * | 0.89 |
| 21 | 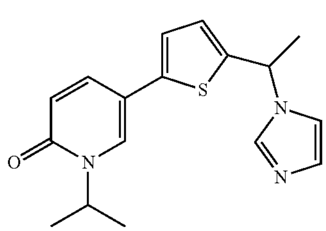 [SMILES: CC(c1ccc(-c2ccc(=O)n(C(C)C)c2)s1)n1ccnc1] | 5-[5-(1-Imidazol-1-yl-ethyl)-thiophen-2-yl]-1-isopropyl-1H-pyridin-2-one | 313.12 | 314.1 | 1.42 |

TABLE 2-continued

| Ex. | Structure | Name | Exact mass | LC-MS [M + H]⁺ (m/z) | LC-MS retention time (min) |
|---|---|---|---|---|---|
| 22 | 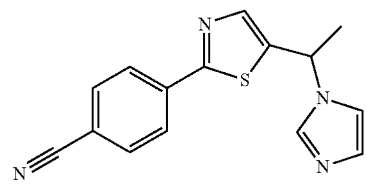 [SMILES: CC(c1cnc(-c2ccc(C#N)cc2)s1)n1ccnc1] | 4-(5-(1-(1H-imidazol-1-yl)ethyl)thiazol-2-yl)benzonitrile | 280.08 | 281.1 | 1.03 |
| 23 | 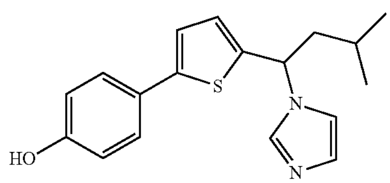 [SMILES: CC(C)CC(c1ccc(-c2ccc(O)cc2)s1)n1ccnc1] | 4-(5-(1-(1H-imidazol-1-yl)-3-methylbutyl)-thiophen-2-yl)phenol | 312.13 | 245.1 * | 2.44 |
| 24 | 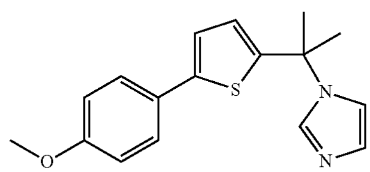 [SMILES: COc1ccc(-c2ccc(C(C)(C)n3ccnc3)s2)cc1] | 1-(2-(5-(4-methoxyphenyl)-thiophen-2-yl)-propan-2-yl)-1H-imidazole | 298.11 | 231.1 * | 2.59 |
| 25 | 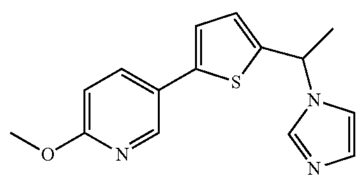 [SMILES: COc1ccc(-c2ccc(C(C)n3ccnc3)s2)cn1] | 5-[5-(1-Imidazol-1-yl-ethyl)-thiophen-2-yl]-2-methoxy-pyridine | 285.09 | 218.1 * | 1.46 |
| 26 | 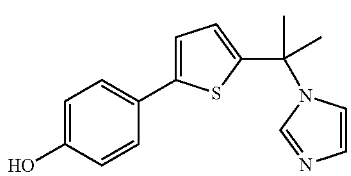 [SMILES: CC(C)(c1ccc(-c2ccc(O)cc2)s1)n1ccnc1] | 4-[5-(1-Imidazol-1-yl-1-methyl-ethyl)-thiophen-2-yl]-phenol | 284.10 | 217.1 * | 2.32 |
| 27 | 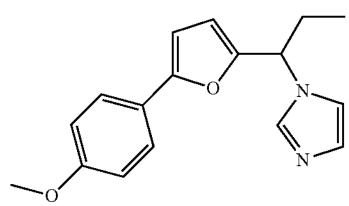 [SMILES: CCC(c1ccc(-c2ccc(OC)cc2)o1)n1ccnc1] | 1-{1-[5-(4-Methoxy-phenyl)-furan-2-yl]-propyl}-1H-imidazole | 282.14 | 215.4 * | 1.46 |
| 28 | 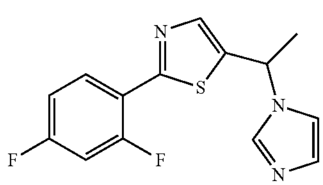 [SMILES: CC(c1cnc(-c2ccc(F)cc2F)s1)n1ccnc1] | 2-(2,4-Difluoro-phenyl)-5-(1-imidazol-1-yl-ethyl)-thiazole | 291.06 | 292.1 | 1.87 |
| 29 | 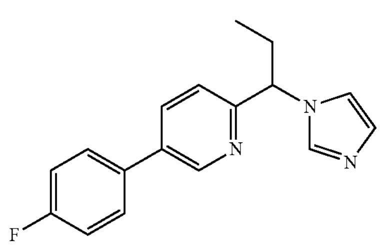 [SMILES: CCC(c1ccc(-c2ccc(F)cc2)cn1)n1ccnc1] | 5-(4-Fluoro-phenyl)-2-(1-imidazol-1-yl-propyl)-pyridine | 281.13 | 282.5 | 1.68 |

TABLE 2-continued

| Ex. | Structure | Name | Exact mass | LC-MS [M + H]+ (m/z) | LC-MS retention time (min) |
|---|---|---|---|---|---|
| 30 | 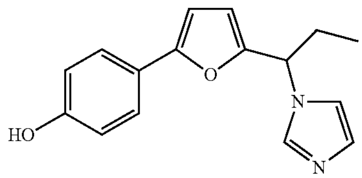 [SMILES: CCC(c1ccc(-c2ccc(O)cc2)o1)n1ccnc1] | 4-[5-(1-Imidazol-1-yl-propyl)-furan-2-yl]-phenol | 268.12 | 201.2 * | 0.89 |
| 31 | 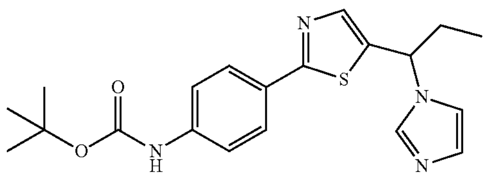 [SMILES: CCC(c1cnc(-c2ccc(NC(=O)OC(C)(C)C)cc2)s1)n1ccnc1] | {4-[5-(1-Imidazol-1-yl-propyl)-thiazol-2-yl]-phenyl}-carbamic acid tert-butyl ester | 384.16 | 317.5 * | 1.24 |
| 32 | 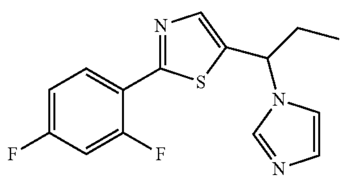 [SMILES: CCC(c1cnc(-c2ccc(F)cc2F)s1)n1ccnc1] | 2-(2,4-Difluoro-phenyl)-5-(1-imidazol-1-yl-propyl)-thiazole | 305.08 | 306.1 | 1.49 |
| 33 | 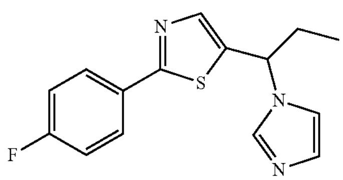 [SMILES: CCC(c1cnc(-c2ccc(F)cc2)s1)n1ccnc1] | 2-(4-Fluoro-phenyl)-5-(1-imidazol-1-yl-propyl)-thiazole | 287.09 | 288.1 | 1.49 |
| 34 | 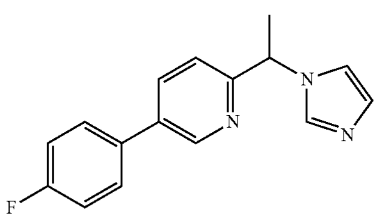 [SMILES: CC(c1ccc(-c2ccc(F)cc2)cn1)n1ccnc1] | 5-(4-Fluoro-phenyl)-2-(1-imidazol-1-yl-ethyl)-pyridine | 267.12 | 268.4 | 1.54 |
| 35 | 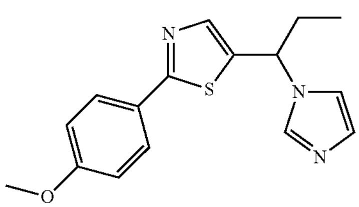 [SMILES: CCC(c1cnc(-c2ccc(OC)cc2)s1)n1ccnc1] | 5-(1-Imidazol-1-yl-propyl)-2-(4-methoxy-phenyl)-thiazole | 299.11 | 300.0 | 3.06 |
| 36 | 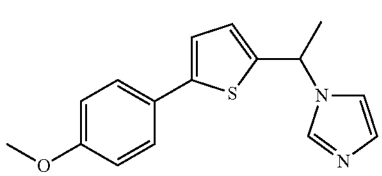 [SMILES: COc1ccc(-c2ccc(C(C)n3ccnc3)s2)cc1] | 1-{1-[5-(4-Methoxy-phenyl)-thiophen-2-yl]-ethyl}-1H-imidazole | 284.10 | 217.2 * | 2.33 |

TABLE 2-continued

| Ex. | Structure | Name | Exact mass | LC-MS [M + H]+ (m/z) | LC-MS retention time (min) |
|---|---|---|---|---|---|
| 37 | 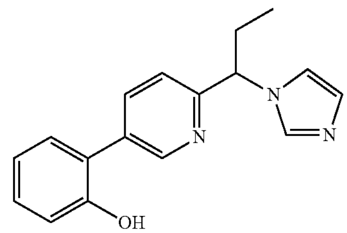 [SMILES: CCC(c1ccc(-c2ccccc2O)cn1)n1ccnc1] | 2-[6-(1-Imidazol-1-yl-propyl)-pyridin-3-yl]-phenol | 279.14 | 280.0 | 1.10 |
| 38 | 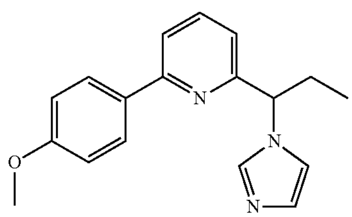 [SMILES: CCC(c1cccc(-c2ccc(OC)cc2)n1)n1ccnc1] | 2-(1-Imidazol-1-yl-propyl)-6-(4-methoxy-phenyl)pyridine | 293.15 | 294.4 | 1.86 |
| 39 | 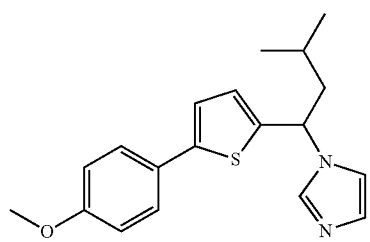 [SMILES: COc1ccc(-c2ccc(C(CC(C)C)n3ccnc3)s2)cc1] | 1-{1-[5-(4-Methoxy-phenyl)-thiophen-2-yl]-3-methyl-butyl}-1H-imidazole | 326.15 | 259.2 * | 2.71 |
| 40 | 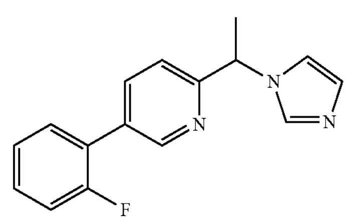 [SMILES: CC(c1ccc(-c2ccccc2F)cn1)n1ccnc1] | 5-(2-Fluoro-phenyl)-2-(1-imidazol-1-yl-ethyl)-pyridine | 267.12 | 268.0 | 0.26 |
| 41 | 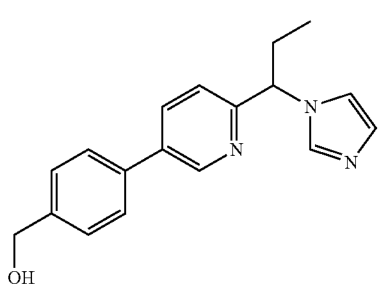 [SMILES: CCC(c1ccc(-c2ccc(CO)cc2)cn1)n1ccnc1] | {4-[6-(1-Imidazol-1-yl-propyl)-pyridin-3-yl]-phenyl}-methanol | 293.15 | 294.5 | 0.85 |
| 42 | 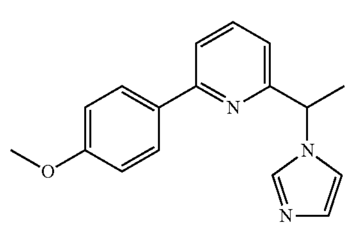 [SMILES: COc1ccc(-c2cccc(C(C)n3ccnc3)n2)cc1] | 2-(1-Imidazol-1-yl-ethyl)-6-(4-methoxy-phenyl)-pyridine | 279.14 | 280.2 | 2.84 |

TABLE 2-continued

| Ex. | Structure | Name | Exact mass | LC-MS [M + H]+ (m/z) | LC-MS retention time (min) |
| --- | --- | --- | --- | --- | --- |
| 43 | 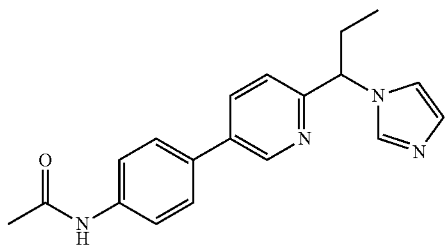 [SMILES: CCC(c1ccc(-c2ccc(NC(C)=O)cc2)cn1)n1ccnc1] | N-{4-[6-(1-Imidazol-1-yl-propyl)-pyridin-3-yl]-phenyl}-acetamide | 320.16 | 321.2 | 1.43 |
| 44 | 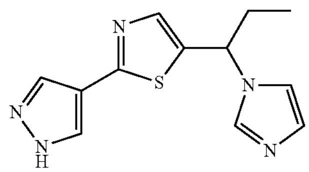 [SMILES: CCC(c1cnc(-c2cn[nH]c2)s1)n1ccnc1] | 5-(1-Imidazol-1-yl-propyl)-2-(1H-pyrazol-4-yl)-thiazole | 259.09 | 260.1 | 1.22 |
| 45 | 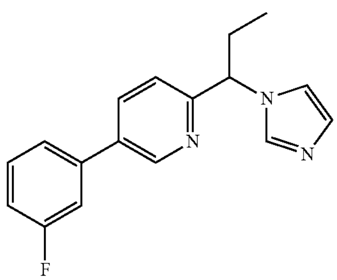 [SMILES: CCC(c1ccc(-c2cccc(F)c2)cn1)n1ccnc1] | 5-(3-Fluoro-phenyl)-2-(1-imidazol-1-yl-propyl)-pyridine | 281.13 | 282.3 | 2.16 |
| 46 | 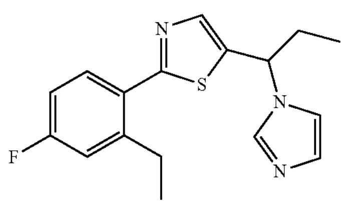 [SMILES: CCc1cc(F)ccc1-c1ncc(C(CC)n2ccnc2)s1] | 2-(2-Ethyl-4-fluoro-phenyl)-5-(1-imidazol-1-yl-propyl)-thiazole | 315.12 | 316.3 | 1.28 |
| 47 | 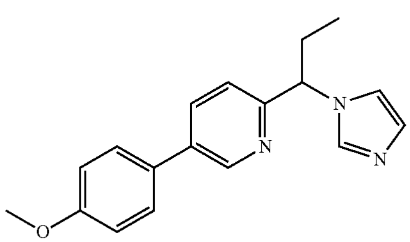 [SMILES: CCC(c1ccc(-c2ccc(OC)cc2)cn1)n1ccnc1] | 2-(1-Imidazol-1-yl-propyl)-5-(4-methoxy-phenyl)-pyridine | 293.15 | 294.14 | 1.32 |
| 48 | 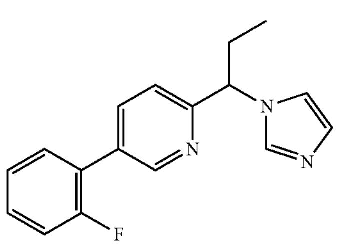 [SMILES: CCC(c1ccc(-c2ccccc2F)cn1)n1ccnc1] | 5-(2-Fluoro-phenyl)-2-(1-imidazol-1-yl-propyl)-pyridine | 281.13 | 282.0 | 0.27 |

TABLE 2-continued

| Ex. | Structure | Name | Exact mass | LC-MS [M + H]+ (m/z) | LC-MS retention time (min) |
| --- | --- | --- | --- | --- | --- |
| 49 | 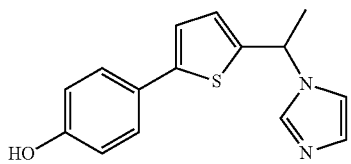 [SMILES: CC(c1ccc(-c2ccc(O)cc2)s1)n1ccnc1] | 4-[5-(1-Imidazol-1-yl-ethyl)-thiophen-2-yl]-phenol | 270.08 | 271.2 | 0.84 |
| 50 | 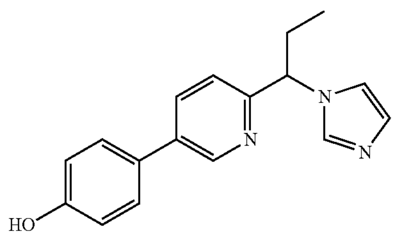 [SMILES: CCC(c1ccc(-c2ccc(O)cc2)cn1)n1ccnc1] | 4-[6-(1-Imidazol-1-yl-propyl)-pyridin-3-yl]-phenol | 279.14 | 212.3 * | 0.91 |
| 51 | 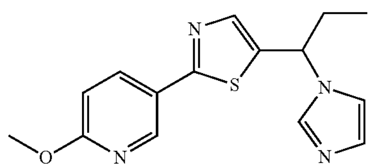 [SMILES: CCC(c1cnc(-c2ccc(OC)nc2)s1)n1ccnc1] | 5-[5-(1-Imidazol-1-yl-propyl)-thiazol-2-yl]-2-methoxy-pyridine | 300.10 | 301.1 | 1.46 |
| 52 | 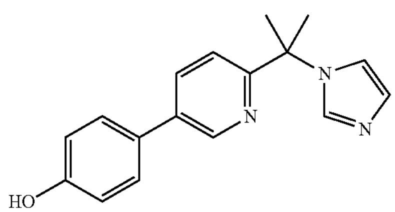 [SMILES: CC(C)(c1ccc(-c2ccc(O)cc2)cn1)n1ccnc1] | 4-[6-(1-Imidazol-1-yl-1-methyl-ethyl)-pyridin-3-yl]-phenol | 279.14 | 212.4 * | 1.50 |
| 53 | 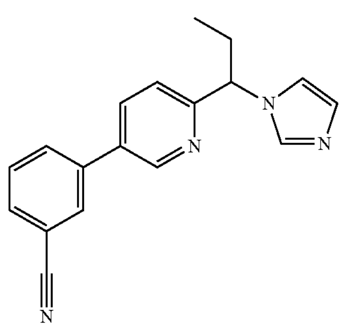 [SMILES: CCC(c1ccc(-c2cccc(C#N)c2)cn1)n1ccnc1] | 3-[6-(1-Imidazol-1-yl-propyl)-pyridin-3-yl]-benzonitrile | 288.14 | 289.5 | 1.22 |
| 54 | 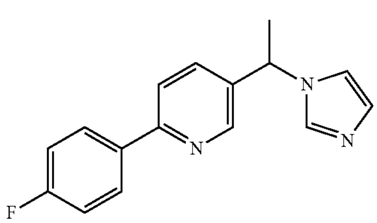 [SMILES: CC(c1ccc(-c2ccc(F)cc2)nc1)n1ccnc1] | 2-(4-Fluoro-phenyl)-5-(1-imidazol-1-yl-ethyl)-pyridine | 267.12 | 268.4 | 1.25 |
| 55 | 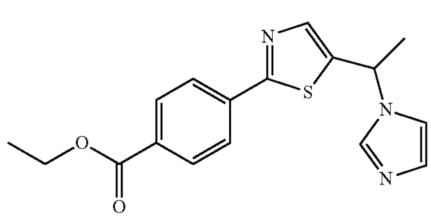 [SMILES: CCOC(=O)c1ccc(-c2ncc(C(C)n3ccnc3)s2)cc1] | 4-[5-(1-Imidazol-1-yl-ethyl)-thiazol-2-yl]-benzoic acid ethyl ester | 327.10 | 328.0 | 0.93 |

TABLE 2-continued

| Ex. | Structure | Name | Exact mass | LC-MS [M + H]+ (m/z) | LC-MS retention time (min) |
|---|---|---|---|---|---|
| 56 | 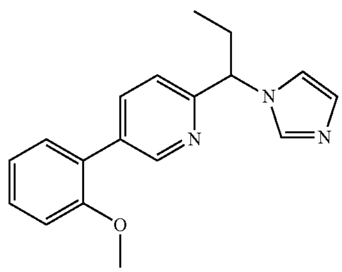 [SMILES: CCC(c1ccc(-c2ccccc2OC)cn1)n1ccnc1] | 2-(1-Imidazol-1-yl-propyl)-5-(2-methoxy-phenyl)-pyridine | 293.15 | 294.5 | 1.25 |
| 57 | 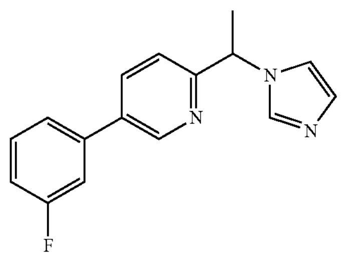 [SMILES: CC(c1ccc(-c2cccc(F)c2)cn1)n1ccnc1] | 5-(3-Fluoro-phenyl)-2-(1-imidazol-1-yl-ethyl)-pyridine | 267.12 | 268.0 | 2.10 |
| 58 | 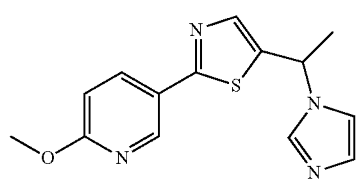 [SMILES: COc1ccc(-c2ncc(C(C)n3ccnc3)s2)cn1] | 5-[5-(1-Imidazol-1-yl-ethyl)-thiazol-2-yl]-2-methoxy-pyridine | 286.09 | 287.1 | 1.43 |
| 59 | 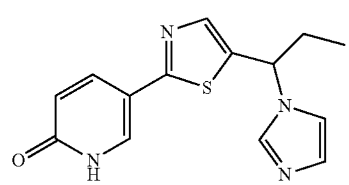 [SMILES: CCC(c1cnc(-c2ccc(=O)[nH]c2)s1)n1ccnc1] | 5-[5-(1-Imidazol-1-yl-propyl)-thiazol-2-yl]-1H-pyridin-2-one | 286.09 | 287.1 | 0.97 |
| 60 | 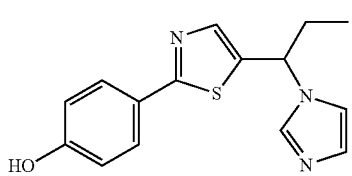 [SMILES: CCC(c1cnc(-c2ccc(O)cc2)s1)n1ccnc1] | 4-[5-(1-Imidazol-1-yl-propyl)-thiazol-2-yl]-phenol | 285.09 | 286.0 | 0.92 |
| 61 | 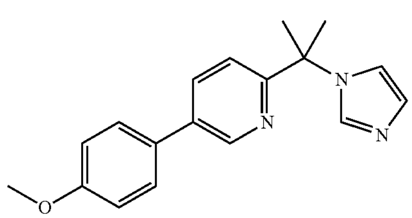 [SMILES: COc1ccc(-c2ccc(C(C)(C)n3ccnc3)nc2)cc1] | 2-(1-Imidazol-1-yl-1-methyl-ethyl)-5-(4-methoxy-phenyl)-pyridine | 293.15 | 226.3 * | 1.44 |

TABLE 2-continued

| Ex. | Structure | Name | Exact mass | LC-MS [M + H]+ (m/z) | LC-MS retention time (min) |
|---|---|---|---|---|---|
| 62 | 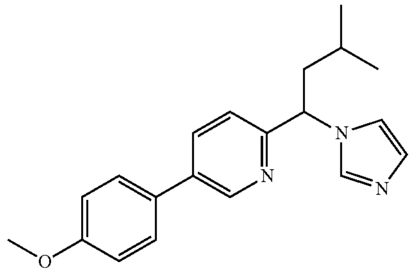 [SMILES: COc1ccc(-c2ccc(C(CC(C)C)n3ccnc3)nc2)cc1] | 2-(1-Imidazol-1-yl-3-methyl-butyl)-5-(4-methoxy-phenyl)-pyridine | 321.18 | 255.4 * | 1.86 |
| 63 | 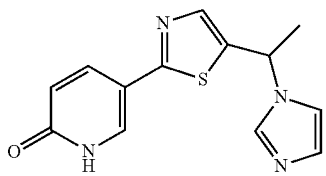 [SMILES: CC(c1cnc(-c2ccc(=O)[nH]c2)s1)n1ccnc1] | 5-[5-(1-Imidazol-1-yl-ethyl)-thiazol-2-yl]-1H-pyridin-2-one | 272.07 | 205.3 * | 0.61 |
| 64 | 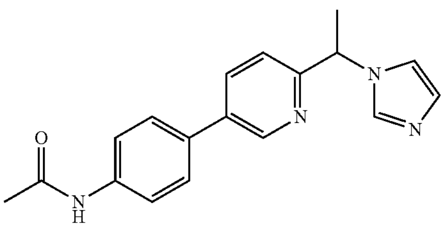 [SMILES: CC(=O)Nc1ccc(-c2ccc(C(C)n3ccnc3)nc2)cc1] | N-{4-[6-(1-Imidazol-1-yl-ethyl)-pyridin-3-yl]-phenyl}-acetamide | 306.15 | 307.4 | 1.16 |
| 65 | 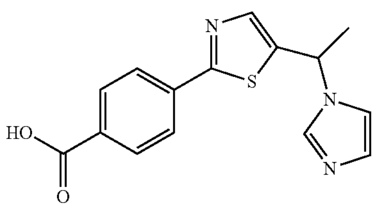 [SMILES: CC(c1cnc(-c2ccc(C(=O)O)cc2)s1)n1ccnc1] | 4-[5-(1-Imidazol-1-yl-ethyl)-thiazol-2-yl]-benzoic acid | 299.07 | 300.0 | 0.75 |
| 66 | 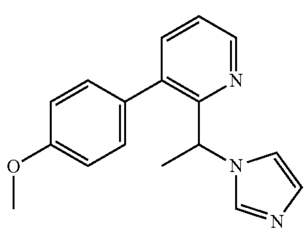 [SMILES: COc1ccc(-c2cccnc2C(C)n2ccnc2)cc1] | 2-(1-(1H-imidazol-1-yl)ethyl)-3-(4-methoxyphenyl)-pyridine | 279.14 | 280.2 | 2.76 |

* m/z for [M − imidazole]+, rather than [M + H]+.

Examples 67-70

The following compounds are prepared using the procedures discussed in Schemes 1-7 and Examples 1-66 noted above:

a) 4-(5-(1-(1H-imidazol-1-yl)ethyl)thiazol-2-yl)-1H-pyrrole-2-carbonitrile

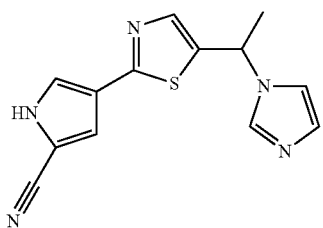 [SMILES: CC(c1cnc(-c2c[nH]c(C#N)c2)s1)n1ccnc1]
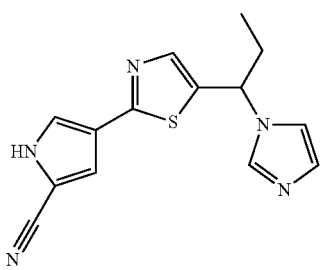 [SMILES: CCC(c1cnc(-c2c[nH]c(C#N)c2)s1)n1ccnc1]

b) 4-(5-(1-(1H-imidazol-1-yl)propyl)thiazol-2-yl)-1H-pyrrole-2-carbonitrile

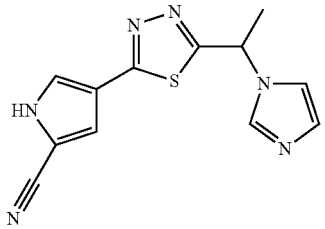 [SMILES: CC(c1nnc(-c2c[nH]c(C#N)c2)s1)n1ccnc1]

c) 4-(5-(1-(1H-imidazol-1-yl)ethyl)-1,3,4-thiadiazol-2-yl)-1H-pyrrole-2-carbonitrile

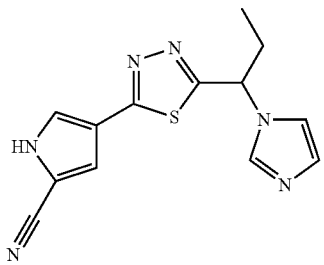 [SMILES: CCC(c1nnc(-c2c[nH]c(C#N)c2)s1)n1ccnc1]

d) 4-(5-(1-(1H-imidazol-1-yl)propyl)-1,3,4-thiadiazol-2-yl)-1H-pyrrole-2-carbonitrile Example 71

CYP17 Inhibition Assay in Rat Testicular Microsomes (Rat CYP17) or Yeast Microsome Overexpressing Human CYP17

A. Materials
1. NADPH (Sigma): A working stock was prepared by adding 25 µL of 6.5 mM NADPH in each tube. The final concentration of NADPH used in the assay was 325 µM.
2. Potassium Phosphate Buffer: One molar (1M) solutions of $K_2HPO_4$ and $KH_2PO_4$ were prepared. Eight mL of the 1 M $KH_2PO_4$ and 1.98 mL of the 1 M $K_2HPO_4$ were combined and the pH was adjusted to 7.4.
3. $^3H_3$-17α-hydroxypregnenolone (American Radiolabeled Chemicals, Inc., stock 1 µCi/µL): A 1:1 dilution of $^3H_3$-17α-hydroxypregnenolone in ethanol was prepared by combining 100 µL $^3H_3$-17α-hydroxypregnenolone+100 µL ethanol for one complete 96 well plate. For the reaction, 2 µL of the diluted $^3H_3$-17α-hydroxypregnenolone was added in each tube, i.e., 1 µCi/reaction.
4. Microsome Isolation Buffer: The microsome isolation buffer was prepared by combining 250 mM Sucrose, 5 mM EDTA, 10 mM Tris HCl, 4 mM DTT, and adjusting to pH 7.4.
5. TEG Buffer: The TEG buffer was prepared by combining 50 mM Tris HCl, 1 mM EDTA, and 20% Glycerol.
6. Rat Testicular Microsomes: Rat testis tissue was collected and disrupted with 30 strokes of a glass homogenizer on ice with 250 µL of microsome isolation buffer, followed by centrifugation at 10,000 g for 10 minutes at 4° C. The supernatant was collected and centrifuged at 100,000 g for 45 minutes at 4° C. The pellet was dissolved in TEG Buffer and the protein was quantified. The homogenized microsome samples were then frozen at −80° C.
7. Yeast Microsomes which overexpress the human CYP17 enzyme were obtained from Premas Biotech, India.

B. Procedure

Potassium phosphate buffer (470 µL) was prepared as described above and was added to each well of a deep well plate. The test compound was diluted using a TECAN liquid handler and 5 µL of diluted compound was transferred to each well (96 deep well/1 mL). A solution (25 µL) of 6.5 mM NADPH was added (final concentration of 325 M in the assay). $^3H_3$-17α-hydroxypregnenolone (2 µL of the working stock) was added to each tube. The plates were then pre-incubated for 15 minutes at 37° C. Following the pre-incubation, either 5 µL rat testicular microsomes (150-160 µg) or 5 µL of yeast microsomes expressing human CYP17 (1.7 pmol), was added. Incubation was at 37° C. for 60 minutes in the presence of oxygen. The plates were then placed in ice and chloroform (500 µL) was added, mixed well and incubated at 4° C. for 20 minutes. The plates were then centrifuged at 1000 rpm for 15 minutes at 4° C.

A portion (300 µL) of the aqueous solution was collected and mixed with a 5% aqueous suspension of activated charcoal (300 µL). The plates were then incubated at 4° C. for 30 minutes, after which the plates were centrifuged at 1000 rpm for 15 minutes at 4° C. From this, 125 µL of the aqueous solution was collected and plated into a 96 well plate. Microscint™ 40 [125 µL, Perkin-Elmer; containing a mixture of a polymer based on alkylphenolethoxylate (20-40%), diethanolamine-phosphoric acid ester ammonium salt (10-20%), sodium dioctyl sulphosuccinate (2.5-10%), triethyl phosphate (2.5-10%), 3,6-dimethyl-4-octyne-3,6-diol (≤2.5%), a polymer based on nonylphenolethoxylate (≤2.5%), diisopropyl naphthalene isomers (40-60%), 2,5-diphenyloxazole (≤2.5%), and 9,10-dimethylanthracene] was added and mixed well. After 30 minutes of incubation, the samples were analyzed with a MicroBeta® Trilux microplate liquid scintillation counter and luminometer (Perkin-Elmer).

Compounds of Formula (I) caused inhibition of rat microsomal CYP17 and recombinant human CYP17 enzyme activity as determined by these assays. Data are listed in Table 3.

Example 72

Cell-Based Human CYP17 Inhibition Assay

A. Materials
1. H295R Adrenocortical Carcinoma Cells and Growth Media: The media for the H295R Adrenocortical carcinoma cells [NCI-H295A, ATCC Number CRL-2128, American Type Culture Collection, Manassas, Va., US] (500 mL) was a DMEM:F12 Mix 1:1 with 5% (2 mL) BD Nu Serum; 1% (5 mL) ITS+Premix [BD Biosciences] and 1% Penstrep.
2. LNCap-CYP17 Cells and Growth Media: Full length hCYP17a1 gene (NCBI Reference Sequence: NM_000102.3) was cloned in pCDNA3.1(+) vector between HindIII and XhoI site. The pCDNA3.1(+) vector contains the Neomycin resistance gene and was used for selection of stable cell line. The hCYP17a1 containing pCDNA3.1(+) was transfected into LNCap cells to create the LNCap-CYP17 cell line. The media for the LNCaP-CYP17 cells was RPMI 1640, 10% FBS, 1% PenStrep, Geneticin 400 µg/mL.

B. Procedure

The H295R cells or LNCaP-hCYP17 cells were subcultured and 30,000 cells per well were seeded in a poly-d lysine plate and incubated overnight at 37° C. The next day the media was removed and 200 L of fresh media with $^3H_3$-17α-hydroxy-pregnenolone (1:1000) was added. 50 µL of serially diluted compounds from a 5× plate (5 times the final desired concentration) was added. The working concentration range for active, new compounds started from a high concentration of 10 M with 3-fold serial dilutions generating up to 10 concentrations. The serial dilution in the 100× plate (in DMSO) and the stamping of a 5× plate (in media) from the 100× plate were carried out using a TECAN liquid handling device.

The plates were incubated overnight (16 hours) at 37° C. After 16 hours, the media was removed (approximately 220 µL) and an equal amount of chloroform was added, mixed and incubated for 30 minutes at 4 degrees. The plate was centrifuged at 4000 rpm for 15 minutes at 4° C., following which the top aqueous layer was carefully removed and added into a new deep well plate. An equal volume of activated 5% charcoal was added, mixed and incubated for 30 minutes at 4° C. The plate was then centrifuged at 4000 rpm for 15 minutes at 4° C. and the top layer carefully separated, avoiding any charcoal contamination, and placed in a white, clear bottom plate (plate cat #3610, Corning Life Sciences). An equal volume of Microscint™ 40 was added and mixed well. Following the incubation for 30 minutes, readings for the radiotracer were taken using a Microbeta® trilux.

Compounds of Formula (I) caused inhibition of human CYP17 enzyme activity as determined by these cell assays. Data are listed in Table 3.

Example 73

Cell-based Functional Assay for Testosterone Production

H295R cells (ATCC Number CRL-2128) were subcultured, seeded (30,000 cells per well in a poly-d lysine plate) and left overnight at 37° C. The next day (after approximately 24 hours), the media were removed and 200 µL fresh media were added. Then, 50 µL of serially diluted compounds was added from a 5× plate. The serial dilution in the 100× plate (in DMSO) and the stamping of a 5× plate (in media) from the 100× plate were carried out using a TECAN liquid handling device. The plate was incubated at 37° C. for 72 hours. After incubation, the media was removed, diluted 5 to 10 times with calibration diluent RD5-48, and the assay performed as per manufacturer's protocol (Parameter Testosterone Assay, Cat. No. KGE010, R&D systems; http://www.rndsystems.com/pdf/KGE010.pdf).

Compounds of Formula (I) caused inhibition of testosterone production in H295R cells as determined by this assay. Data are listed in Table 3.

Example 74

In Vivo Inhibition of Testosterone Production

Male rats aged 8 to 10 weeks old are dosed orally with compounds at 10 or 30 mg/kg. Blood samples are drawn at 0.5, 3, 8, and 24 h, and are processed to plasma samples. Samples are analyzed for compound levels by LC-MS/MS method and for testosterone levels with an ELISA performed as per manufacturer's protocol (Parameter Testosterone Assay, Cat. No. KGE010, R&D systems; http://www.rndsystems.com/pdf/KGE010.pdf). The serum testosterone level is calculated from standards using GraphPad Prism software and % inhibition at a given time is calculated by comparing the testosterone level in vehicle control animals at the same time of day.

Compounds of Formula (I) decrease serum testosterone levels as determined by this assay protocol.

Example 75

In Vivo Reduction of Prostate and Seminal Vesicle Weights

Male rats aged 8 to 10 weeks old (5 animals per group) are dosed orally with compounds once or twice a day at 12-hour intervals for 14 days. On day 14 the animals are euthanized and organs are surgically removed for wet weight determination including the prostate, seminal vesicles and testes. Compounds of Formula (I) decrease prostate and seminal vesicle weights as determined by this assay protocol.

TABLE 3

| Ex. | CYP17 (rat testicular microsomes) | CYP17 (human, yeast microsomes) | CYP17 (human H295R adrenal cells) | CYP17 (human LNCap-CYP17 cells) | Testosterone (human H295R adrenal cells) |
|---|---|---|---|---|---|
| 1 | A | | B | | |
| 2 | B | | C | | |
| 3 | A | | A | | |
| 4 | A | | A | | |
| 5 | B | | B | C | |
| 6 | C | | C | | |
| 7 | A | A | A | B | |
| 8 | A | A | A | B | |
| 9 | A | | C | | |
| 10 | A | | C | | |
| 11 | B | | B | | |
| 12 | A | | A | | C |
| 13 | A | | C | | |
| 14 | B | | C | | |
| 15 | B | | B | | |
| 16 | A | | B | | |
| 17 | A | | B | | |
| 18 | A | | C | | |
| 19 | A | | B | | |
| 20 | A | C | A | | A |
| 21 | A | | B | | C |
| 22 | A | | B | | C |
| 23 | A | | A | | |
| 24 | A | B | A | | |
| 25 | A | | A | | |
| 26 | A | | A | | |
| 27 | A | A | A | B | |
| 28 | A | B | A | | B |
| 29 | A | | A | | |
| 30 | A | A | A | A | |
| 31 | A | | A | | |
| 32 | A | | A | | |
| 33 | A | | A | | |
| 34 | A | | A | | |
| 35 | A | C | B | C | |
| 36 | A | | A | | |
| 37 | A | B | A | C | |
| 38 | A | C | B | | |
| 39 | A | | A | | |
| 40 | A | | B | | |
| 41 | A | | B | | |
| 42 | A | | B | | |
| 43 | A | | B | | |
| 44 | A | | B | | |
| 45 | A | | A | | |
| 46 | A | | A | | |
| 47 | A | C | B | | |
| 48 | A | | A | | |

TABLE 3-continued

| Ex. | CYP17 (rat testicular microsomes) | CYP17 (human, yeast microsomes) | CYP17 (human H295R adrenal cells) | CYP17 (human LNCap-CYP17 cells) | Testosterone (human H295R adrenal cells) |
|---|---|---|---|---|---|
| 49 | A | | B | A | B |
| 50 | A | | A | A | |
| 51 | A | | | B | |
| 52 | A | | | B | |
| 53 | A | | | B | |
| 54 | A | | | C | |
| 55 | A | | | B | |
| 56 | A | C | | B | C |
| 57 | A | | | B | |
| 58 | B | | | B | |
| 59 | B | | | C | |
| 60 | B | C | | B | C |
| 61 | B | | | B | |
| 62 | B | | | B | |
| 63 | C | | | C | |
| 64 | C | | | C | |
| 65 | C | | | C | |
| 66 | B | | | A | |

Activities (nM): A: $IC_{50} < 50$; B: $IC_{50} = 50-200$; C: $IC_{50} = 201-10000$.

All publications cited in this specification and priority applications, including U.S. Provisional Patent Application No. 61/541,634 and International Patent Application No. PCT/US2012/57908, are incorporated herein by reference. While the invention has been described with reference to particular embodiments, it will be appreciated that modifications can be made without departing from the spirit of the invention. Such modifications are intended to fall within the scope of the appended claims.

What is claimed is:

1. A compound of formula (I) having the structure:

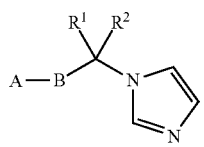

wherein:
A is optionally substituted phenyl, or pyridine, -2-pyridone, furan, or pyrazole, substituted on the ring carbon atoms with 0 to 2 groups independently selected from $CH_3$, $CH_3O$, $CF_3$, F, Cl, and CN; and substituted on the nitrogen atom in 2-pyridone and pyrazole with H or $C_1$ to $C_4$ alkyl;

B is selected from the group consisting of

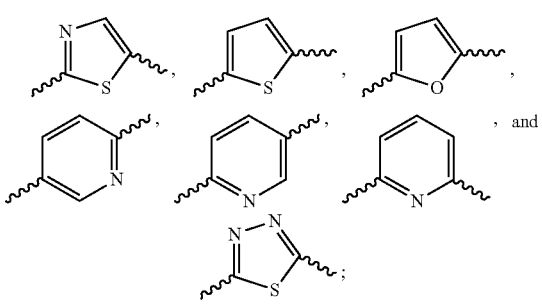

$R^1$ is H or optionally substituted $C_1$ to $C_6$ alkyl; and
$R^2$ is optionally substituted $C_1$ to $C_6$ alkyl;
or a pharmaceutically acceptable salt thereof.

2. The compound according to claim 1, wherein A is of the structure:

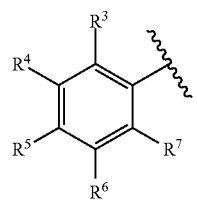

wherein:
$R^3$, $R^4$, $R^5$, $R^6$ and $R^7$ are, independently, selected from the group consisting of H, halogen, OH, CN, optionally substituted $C_1$ to $C_6$ alkyl, $C_1$ to $C_6$ alkoxy, amino, ($C_1$ to $C_4$ alkyl)—NH—, ($C_1$ to $C_4$ alkyl)$_2$N—, HC $H_2$NC(O)—, ($C_1$ to $C_4$ alkyl)-NHC(O)—, ($C_1$ to $C_4$ alkyl)$_2$NC(O)—, HC(O)NH—, ($C_1$ to $C_4$ alkyl)-C(O)NH—, COOH, $C_1$ to $C_6$ alkylsulfonyl and —C(O)O($C_1$ to $C_4$ alkyl);
with the proviso that 3, 4 or 5 of $R^3$, $R^4$, $R^5$, $R^6$ and $R^7$ are hydrogen.

3. The compound according to claim 2, wherein $R^3$, $R^4$, $R^5$, $R^6$ and $R^7$ are independently selected from H, OH, F, Cl, CN, $C_1$ to $C_4$ alkyl, $C_1$ to $C_4$ alkoxy, amino, methylamino, dimethylamino, $H_2NC(O)$—, $CH_3NHC(O)$—, $(CH_3)_2NC(O)$—, HC(O)NH—, $CH_3C(O)NH$—, COOH, methyl-sulfonyl and —C(O)O($C_1$ to $C_4$ alkyl);
with the proviso that 3, 4 or 5 of $R^3$, $R^4$, $R^5$, $R^6$ and $R^7$ are hydrogen.

4. The compound according to claim 3, wherein $R^1$ is H, or $C_1$ to $C_4$ alkyl; and $R^2$ is $C_1$ to $C_4$ alkyl.

5. The compound according to claim 3, wherein $R^1$ is H, or $C_1$ to $C_4$ alkyl; $R^2$ is $C_1$ to $C_4$ alkyl; and B is

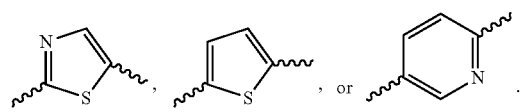

6. The compound according to claim 1, wherein A is:

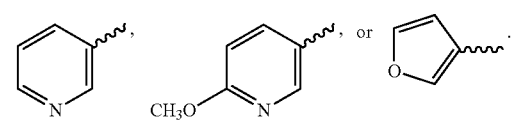

7. The compound according to claim 1, wherein A is 2-pyridone or pyrazole and is substituted on the nitrogen atom with H or $C_1$ to $C_4$ alkyl.

8. The compound according to claim 1, wherein A is:

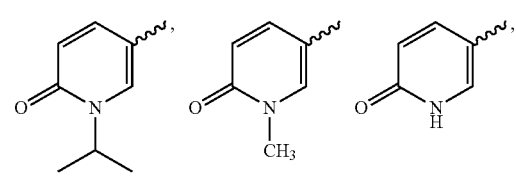

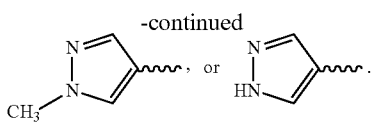

9. The compound according to claim 1, wherein:
R$^1$ is H or C$_1$ to C$_4$ alkyl;
R$^2$ is C$_1$ to C$_4$ alkyl; and
B is

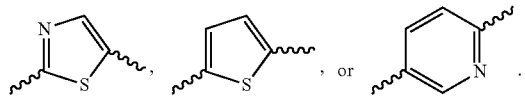

10. The compound according to claim 1, wherein B is

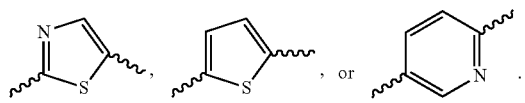

11. The compound according to claim 1, wherein R$^1$ is H, or C$_1$ to C$_4$ alkyl; and R$^2$ is C$_1$ to C$_4$ alkyl.

12. The compound according to claim 1, which is:
2-(3-Fluoro-phenyl)-5-(1-imidazol-1-yl-propyl)-thiazole;
5-(1-Imidazol-1-yl-propyl)-2-(1-methyl-1H-pyrazol-4-yl)-thiazole;
1-{1-[5-(4-Methoxy-phenyl)-thiophen-2-yl]-propyl}-1H-imidazole;
4-[5-(1-Imidazol-1-yl-propyl)-thiophen-2-yl]-phenol;
4-[6-(1-Imidazol-1-yl-propyl)-pyridin-3-yl]-benzoic acid ethyl ester;
4-[6-(1-Imidazol-1-yl-propyl)-pyridin-3-yl]-benzoic acid;
2-(1-Imidazol-1-yl-propyl)-5-(3-methoxy-phenyl)-pyridine;
3-[6-(1-Imidazol-1-yl-propyl)-pyridin-3-yl]-phenol;
4-[6-(1-Imidazol-1-yl-propyl)-pyridin-3-yl]-N-methyl-benzamide;
4-[6-(1-Imidazol-1-yl-propyl)-pyridin-3-yl]-benzamide;
2-(1-Imidazol-1-yl-propyl)-5-(4-methoxymethoxymethyl-phenyl)-pyridine;
5-(4-Fluoro-phenyl)-2-(1-imidazol-1-yl-ethyl)-pyridine;
2-[1-(2,3-Dihydro-imidazol-1-yl)-ethyl]-5-furan-3-yl-pyridine;
4-[6-(1-Imidazol-1-yl-ethyl)-pyridin-3-yl]-phenylamine;
2-(1-Imidazol-1-yl-ethyl)-5-(4-methoxy-phenyl)-pyridine;
4-[6-(1-Imidazol-1-yl-ethyl)-pyridin-3-yl]-phenol;
4-[6-(1-Imidazol-1-yl-propyl)-pyridin-3-yl]-benzonitrile;
2-[6-(1-Imidazol-1-yl-propyl)-pyridin-3-yl]-benzonitrile;
2-(4-Fluoro-phenyl)-5-(1-imidazol-1-yl-propyl)-[1,3,4]thiadiazole;
5-[5-(1-Imidazol-1-yl-ethyl)-thiophen-2-yl]-1-methyl-1H-pyridin-2-one;
5-[5-(1-Imidazol-1-yl-ethyl)-thiophen-2-yl]-1-isopropyl-1H-pyridin-2-one;
4-(5-(1-(1H-imidazol-1-yl)ethyl)thiazol-2-yl)benzonitrile;
4-(5-(1-(1H-imidazol-1-yl)-3-methylbutyl)-thiophen-2-yl)phenol;
1-(2-(5-(4-methoxyphenyl)-thiophen-2-yl)-propan-2-yl)-1H-imidazole;
5-[5-(1-Imidazol-1-yl-ethyl)-thiophen-2-yl]-2-methoxy-pyridine;
4-[5-(1-Imidazol-1-yl-1-methyl-ethyl)-thiophen-2-yl]-phenol;
1-{1-[5-(4-Methoxy-phenyl)-furan-2-yl]-propyl}-1H-imidazole;
2-(2,4-Difluoro-phenyl)-5-(1-imidazol-1-yl-ethyl)-thiazole;
5-(4-Fluoro-phenyl)-2-(1-imidazol-1-yl-propyl)-pyridine;
4-[5-(1-Imidazol-1-yl-propyl)-furan-2-yl]-phenol;
{4-[5-(1-Imidazol-1-yl-propyl)-thiazol-2-yl]-phenyl}-carbamic acid tert-butyl ester;
2-(2,4-Difluoro-phenyl)-5-(1-imidazol-1-yl-propyl)-thiazole;
2-(4-Fluoro-phenyl)-5-(1-imidazol-1-yl-propyl)-thiazole;
5-(4-Fluoro-phenyl)-2-(1-imidazol-1-yl-ethyl)-pyridine;
5-(1-Imidazol-1-yl-propyl)-2-(4-methoxy-phenyl)-thiazole;
1-{1-[5-(4-Methoxy-phenyl)-thiophen-2-yl]-ethyl}-1H-imidazole;
2-[6-(1-Imidazol-1-yl-propyl)-pyridin-3-yl]-phenol;
2-(1-Imidazol-1-yl-propyl)-6-(4-methoxy-phenyl)-pyridine;
1-{1-[5-(4-Methoxy-phenyl)-thiophen-2-yl]-3-methyl-butyl}-1H-imidazole;
5-(2-Fluoro-phenyl)-2-(1-imidazol-1-yl-ethyl)-pyridine;
{4-[6-(1-Imidazol-1-yl-propyl)-pyridin-3-yl]-phenyl}-methanol;
2-(1-Imidazol-1-yl-ethyl)-6-(4-methoxy-phenyl)-pyridine;
N-{4-[6-(1-Imidazol-1-yl-propyl)-pyridin-3-yl]-phenyl}-acetamide;
5-(1-Imidazol-1-yl-propyl)-2-(1H-pyrazol-4-yl)-thiazole;
5-(3-Fluoro-phenyl)-2-(1-imidazol-1-yl-propyl)-pyridine;
2-(2-Ethyl-4-fluoro-phenyl)-5-(1-imidazol-1-yl-propyl)-thiazole;
2-(1-Imidazol-1-yl-propyl)-5-(4-methoxy-phenyl)-pyridine;
5-(2-Fluoro-phenyl)-2-(1-imidazol-1-yl-propyl)-pyridine;
4-[5-(1-Imidazol-1-yl-ethyl)-thiophen-2-yl]-phenol;
4-[6-(1-Imidazol-1-yl-propyl)-pyridin-3-yl]-phenol;
5-[5-(1-Imidazol-1-yl-propyl)-thiazol-2-yl]-2-methoxy-pyridine;
4-[6-(1-Imidazol-1-yl-1-methyl-ethyl)-pyridin-3-yl]-phenol;
3-[6-(1-Imidazol-1-yl-propyl)-pyridin-3-yl]-benzonitrile;
2-(4-Fluoro-phenyl)-5-(1-imidazol-1-yl-ethyl)-pyridine;
4-[5-(1-Imidazol-1-yl-ethyl)-thiazol-2-yl]-benzoic acid ethyl ester;
2-(1-Imidazol-1-yl-propyl)-5-(2-methoxy-phenyl)-pyridine;
5-(3-Fluoro-phenyl)-2-(1-imidazol-1-yl-propyl)-pyridine;
5-[5-(1-Imidazol-1-yl-ethyl)-thiazol-2-yl]-2-methoxy-pyridine;
5-[5-(1-Imidazol-1-yl-propyl)-thiazol-2-yl]-1H-pyridin-2-one;
4-[5-(1-Imidazol-1-yl-propyl)-thiazol-2-yl]-phenol;
2-(1-Imidazol-1-yl-1-methyl-ethyl)-5-(4-methoxy-phenyl)-pyridine;
2-(1-Imidazol-1-yl-3-methyl-butyl)-5-(4-methoxy-phenyl)-pyridine;
5-[5-(1-Imidazol-1-yl-ethyl)-thiazol-2-yl]-1H-pyridin-2-one;

N-{4-[6-(1-Imidazol-1-yl-ethyl)-pyridin-3-yl]-phenyl}-acetamide;

4-[5-(1-Imidazol-1-yl-ethyl)-thiazol-2-yl]-benzoic acid;

4-(5-(1-(1H-imidazol-1-yl)ethyl)thiazol-2-yl)-1H-pyrrole-2-carbonitrile;

4-(5-(1-(1H-imidazol-1-yl)propyl)thiazol-2-yl)-1H-pyrrole-2-carbonitrile;

4-(5-(1-(1H-imidazol-1-yl)ethyl)-1,3,4-thiadiazol-2-yl)-1H-pyrrole-2-carbonitrile;

4-(5-(1-(1H-imidazol-1-yl)propyl)-1,3,4-thiadiazol-2-yl)-1H-pyrrole-2-carbonitrile; or 2-(1-(1H-imidazol-1-yl)ethyl)-3-(4-methoxyphenyl)pyridine.

13. A pharmaceutical composition comprising a compound according to claim 1 and a pharmaceutically acceptable carrier.

14. A kit comprising a compound according to claim 1.

15. A method for regulating CYP17, said method comprising administering a therapeutically effective amount of a compound of claim 1 to a patient in need thereof.

16. The method according to claim 15, wherein said regulation comprises inhibition of CYP17 activity.

17. A method of treating prostate cancer in a patient, said method comprising administering a compound of claim 1 to said patient.

18. A method of reducing testosterone production in a patient, comprising administering a compound of claim 1 to said patient.

* * * * *